United States Patent
Mitchell et al.

(10) Patent No.: US 9,862,716 B2
(45) Date of Patent: Jan. 9, 2018

(54) TRKA KINASE INHIBITORS, COMPOSITIONS AND METHODS THEREOF

(71) Applicant: Merck Sharp & Dohme Corp., Rahway, NJ (US)

(72) Inventors: Helen Mitchell, Richboro, PA (US); Mark E. Fraley, North Wales, PA (US); Andrew J. Cooke, West Point, PA (US); Craig A. Stump, West Point, PA (US); Yi-Heng Chen, Whippany, NJ (US); Xu-Fang Zhang, Dresher, PA (US); Casey C. McComas, Phoenixville, PA (US); Kathy Schirripa, Quakertown, PA (US); Melody McWherter, Boyertown, NJ (US); Swati P. Mercer, Philadelphia, PA (US); Keith P. Moore, Doylestown, PA (US); Ping Liu, Westfield, NJ (US); Harold B. Wood, Westfield, NJ (US); Chun Sing Li, Shanghai (CN); Qinghua Mao, Shanghai (CN); Douglas C. Beshore, Lower Gwynedd, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/129,206

(22) PCT Filed: Mar. 23, 2015

(86) PCT No.: PCT/US2015/022004
§ 371 (c)(1),
(2) Date: Sep. 26, 2016

(87) PCT Pub. No.: WO2015/148373
PCT Pub. Date: Oct. 1, 2015

(65) Prior Publication Data
US 2017/0114056 A1   Apr. 27, 2017

(30) Foreign Application Priority Data

Mar. 26, 2014  (WO) ............... PCT/CN2014/074143

(51) Int. Cl.
C07D 471/04   (2006.01)
C07D 513/04   (2006.01)

(52) U.S. Cl.
CPC ......... *C07D 471/04* (2013.01); *C07D 513/04* (2013.01)

(58) Field of Classification Search
CPC ........................... C07D 471/04; C07D 513/04
See application file for complete search history.

(56) References Cited

U.S. PATENT DOCUMENTS

| 9,289,419 B2 * | 3/2016 | Sasmal ............... A61K 31/437 546/121 |
| 2005/0009876 A1 | 1/2005 | Bhagwat et al. |
| 2005/0143384 A1 | 6/2005 | Sartori et al. |
| 2010/0029619 A1 | 2/2010 | Uchikawa et al. |
| 2010/0120862 A1 | 5/2010 | Tafesse |
| 2010/0292207 A1 | 11/2010 | Lombardi Borgia et al. |

FOREIGN PATENT DOCUMENTS

| CN | 10224153 | 10/2011 |
| EP | 1181318 | 5/2000 |
| EP | 1388341 | 8/2002 |
| WO | WO200178698 A2 | 10/2001 |
| WO | WO2004058184 A2 | 7/2004 |
| WO | WO2004096122 | 11/2004 |
| WO | WO2004098518 A2 | 11/2004 |
| WO | WO2005019266 A2 | 3/2005 |
| WO | WO2005030128 | 4/2005 |
| WO | WO2005061540 | 7/2005 |
| WO | WO2005110994 | 11/2005 |
| WO | WO2006137106 | 6/2006 |
| WO | WO2007013673 | 7/2006 |

(Continued)

OTHER PUBLICATIONS

Su et al. "A bulky biaryl . . . " Angew. Chem. Int. Ed. v. 51, pp. 4710-4713 (2012).*
Adriaenssens, et al., Nerve Growth Factor is a Potential Therapeutic Target in Breast Cancer, Cancer Research, 2008, 346-351, 68-2.
Asaumi et al., Expression of Neurotrophins and Their Receptors (TRK) During Fracture Healing, Bone, 2000, pp. 625-633, 26.
Bardelli et al., Mutational Analysis of the Tryosine Kinome in Colorectal Cancers, Science, May 9, 2003, pp. 949, 300.
Brodeur et al., Neuroblastoma: Biological Insights into a Clincal Enigma, Nat. Rev Cancer, 2003, pp. 203-216, 3.

(Continued)

*Primary Examiner* — Timothy R Rozof
(74) *Attorney, Agent, or Firm* — Sylvia A. Ayler; John C. Todaro

(57) ABSTRACT

The present invention is directed to a bicyclic heteroaryl benzamide compounds of formula (I) which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

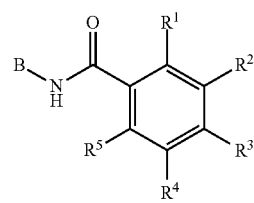

(I)

16 Claims, No Drawings

(56) References Cited

FOREIGN PATENT DOCUMENTS

| WO | WO2006087538 | 8/2006 |
|---|---|---|
| WO | WO2006115452 | 11/2006 |
| WO | WO2006123113 | 11/2006 |
| WO | WO2006131952 | 12/2006 |
| WO | WO2007025540 A2 | 3/2007 |
| WO | WO2007042321 | 4/2007 |
| WO | WO2007069773 A1 | 6/2007 |
| WO | 2008003770 A1 | 1/2008 |
| WO | WO2008052734 | 5/2008 |
| WO | WO2008124610 A1 | 10/2008 |
| WO | WO2009003999 A2 | 1/2009 |
| WO | WO2009046802 A1 | 4/2009 |
| WO | WO2009003998 | 8/2009 |
| WO | WO2010033941 A1 | 3/2010 |
| WO | WO2010077680 A2 | 7/2010 |
| WO | WO2010111653 | 9/2010 |
| WO | WO2012003387 A1 | 1/2012 |
| WO | WO2012028579 A1 | 3/2012 |
| WO | WO2012100223 A1 | 7/2012 |
| WO | WO2012107434 A1 | 8/2012 |
| WO | WO2012158413 | 11/2012 |
| WO | WO2012159565 A1 | 11/2012 |
| WO | WO2012161879 A1 | 11/2012 |

OTHER PUBLICATIONS

Dang et al., Expression of Nerve Growth Factor Receptors is Correlated with Progression and Prognosis of Human Pancreatic Cancer, J. of Gastroenterology and Hepatology, 2006, pp. 850-858, 21 (5).
Davidson, et al., Expression and Activation of the Nerve Growth Factor Receptor TrkA in Serous Ovarian Carcinoma, Clinical Cancer Research, 2003, 2248-2259, 9.
Delafoy et al., Role of Nerve Growth Factor in the Trinitrobenzene Sulfonic Acid-Induced Colonic Hypersensitivity, Pain, 2003, pp. 489-497, 105.
Di Mola, Nerve Growth Factor and Trk Hihg Affinity Receptor (TRkA) Gene Expression in Inflammatory Bowel Disease, Gut, 2000, pp. 670-678, 46(5).
Dionne et al., Cell cycle-independent death of prostate adenocarcinoma is Induced by the trk Tyrosine Kinase Inhibitor CEP-751 (KT6587), Clinical Cancer Research, 1998, pp. 1887-1898, 4(8).
Dou et al., Increased nerve growth factor and its receptors in atopic dermatitis:, Archives of Dermatological Research, 2006, pp. 31-37 (1), 298.
Du, et al., Effect of trimerization motifs on quaternary structure antigenicity, and immunogenicity of a noncleavable HIV-1 gp140 envelope glycoprotein, Virology, 2009, pp. 33-44, vol. 395.
Eguchi et. al., Fusion of ETV6 to Neurotrophin-3 Receptor TRKC in Acute Myeloid Leukemia With . . . , Blood, 1999, 1355-1363, 93-4.
Euhus, et al., ETV6-NTRK3 Trk-ing the primary event in human secretory breast cancer, Cancer Cell, 2002, 347-348, 2.
Freund-Michel et al., The Nerve Growth Factor and Its Receptors in Airway Inflammatory Diseases, Pharmacology & Thereapeutics, 2008, pp. 52-76, 117 (1).
Greco, et al., Reaarangements of NTRK1 gene in papillary thyroid carcinoma, Molecular and Cellular Endocrinology, 2010, 44-49, 321.
Gruber-Olipitz, et al., Synthesis, Chaperoning, and Metabolism of Proteins . . . , Journal of Proteome Research, 2008, 1932-1944, 7.
Hu et al., Decrease in Bladder Overactivity With REN1820 in Rats, J. of Urology, 2005, pp. 1016-1021, 173(3).
Iannone, Increased Expression of Nerve Growth Factoer (NGF) and high Affinity NGF Receptor (p140 TrkA) in Human Osteoarthritic Chondrocytes, Rheumatology, 2002, pp. 1413-1418, 4.
Jaggar et al., Inflammation of the Rat Urinary Bladder is associated with a Referred Thermal Hyperalgesia Which is Nerve Growth Factor Dependent, Br. J. Anaesth., 1999, pp. 442-448, 83.

Jin, et al., TrkC plays an essential role in breat tumor growth and metastasis, Carcinogenesis, 2010, 1939-1947, 31-11.
Kruttgen et al., The Dark Side of the NGF Family: Neurotrophin in Neoplasia, Brain Pathology, 2006, pp. 304-310, 16.
Lamb et al., Nerve Growth Factor and Gastric Hyperalgesia in the Rat, Neurogastroenterol Motil., 2003, pp. 355-361, 15.
Li, Yi-Gong, Correlation of expressions of GFAP, NT-3, Trk and NCAM with neurotropic molecular mechanism and clinical factors in adenoid cystic carcinoma of salivary gland, Chinese Journal of Cancer Prevention and Treatment, 2009, 428-430, 16-6.
Ma et al., The Progressive Tactile Hyperalgesia Induced by Peripheral Inflammation is Nerve Growth Factor Dependent, Neuroreport, 1997, pp. 807-810, 8.
Marchetti et al., Frequent Mutations in the Neuroptrophic Trrosine Receptor Kinase Gene Family in Large Cell Neuroendocrine Carcinioma of the Lung, Rapid Communication, 2008, pp. 609-616, 29 (5).
McMahon et al., The Biological Effects of Endogenous Nerve Growth Factor on Adult Sensory Neurons Revealed by a trkA-IgG Fusion Molecule, Nature Medicine, 1995, pp. 774-780, 1.
N-(Imidazo[1,2-a]pyridin-3-yl)benzamide. Oxchem. 2013: [retrieved on Sep. 3, 2015].Retrieved from the Internet. <URL: http://www.ox-chem.com/ox/Product/Pro_Item. aspx?Num=AX8235552>. entire document.
Nakagawara, et al., Trk Receptor Tyrosine Kinases: a bridge between cancer and neural development, Cancer Letters, 2001, 107-114, 169.
Papatsoris, et al., Manipulation of the nerve growth factor network in prostate cancer, Expert Opinion on Investigational Drugs, 2007, 303-309, 16-3.
Raychaudhuri et al., K252a, a High-Affinity Nerve Growth Factor Receptor Blocker,, J. of Investigative Dermatology, 2004, pp. 812-819, 122 (3).
Ricci, et al., Neurotrophins and Neurotrophin Receptors in Human Lung Cancer, Am. J. Respir. Cell Mol. Biol., 2001, 439-446, 25.
Shelton et al., Nerve growth factor mediates hyperalgesia and cachexia, Pain, 2005, pp. 8-16, 116.
Sohrabji et al., Estrogen—BDNF interactions: Implications, Frontiers in Neuroendocrinology, 2006, pp. 404-414, 27 (4).
Tripathy et al., TrkA kinase inhibitors from a library of modified and isosteric, Bioganic & Medicinal Chemistry Letters, 2008, pp. 3551-3555, 18.
Truzzi, et al., Neurotrophin in healthy and diseased skin, Dermato-Endocrinology, 2011, 32-36, 3-1.
Undevia et al., Phase I Clinical Trial of CEP-2563 Dihydrochloride, A Receptor Tyrosine Kinase Inhibitor, in Patients with Refractory Solid Tumors, Investigational New Drugs, 2004, pp. 449-458, 22.
Vaishnavi, et al., Oncogenic and drug-sensitive NTRK1 rearrangements in lung cancer, Nature Medicine, 2013, 1469-1472, 19-11.
Wadhwa, S.; et al., Expression of Neurotrophins receptors Trk A and Trk B in adult human astrocytoma and glioblastoma, Journal of Biosciences, 2003, 181-188, 28-2.
Wang et al., Trk Kinase Inhibitors as New Treatments for Cancer and Pain, Expert Opinion, 2009, pp. 305-319, 19 (3).
Woolf, Nerve Growth Factor Contributes to the Generation of Inflammatory Sensory Hypersenstivity, Neuroscience, 1994, pp. 327-331, 62.
Yilmaz, et al., Therapeutic targeting of Trk supresses tumor proliferation and enhances cisplatin activity in HNSCC, Cancer Biology and Therapy, 2010, 644-653, 10-6.
Zahn et al., Effect of Blockade of Nerve Growth Factor and Tumor Necrosis Factor on Pain Behaviors After Plantar Incision, J. Pain, 2004, pp. 157-163, 5.
Zhang et al., Investigation of lectin modified insulin liposomes as carriers for oral administration, International Journal of Pharmaceutics, 2005, pp. 247-259, 294.
Zhu et al., Nerve Growth Factor Expression Correlation with Perineural Invasion and Pain in Human Pancreatic Cancer, J. of Clinicl Oncology, 1999, pp. 2419-2428, 17.

* cited by examiner

TRKA KINASE INHIBITORS, COMPOSITIONS AND METHODS THEREOF

CROSS REFERENCE TO RELATED APPLICATIONS

This application is the National Stage of International Application No. PCT/US2015/022004074143 filed on Mar. 23, 2015, which claims the benefit under 35 U.S.C. 119 (b) and 37 CFR 1.55, Application No. PCT/CN2014/074143, filed Mar. 26, 2014.

The invention is directed to a class of bicyclic heteroaryl benzamide compounds, their salts, pharmaceutical compositions comprising them and their use in therapy of the human body. In particular, the invention is directed to a class of substituted bicyclic heteroaryl benzamide compounds, which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

Trk's are high affinity binding protein kinase receptors that are activated by Neurotrophins (NT), a group of soluble growth factors including Nerve Growth Factor (NGF), Brain-Derived Neurotrophic Factor (BDNF) and Neurotrophin 3-5 (NT 3-5). The Trk's consist of three family members TrkA, TrkB and TrkC that bind to and mediate the signal transduction derived from the Neurotrophins. NGF activates TrkA, BDNF and NT-4/5 activate TrkB and NT3 activates TrkC.

Inhibitors of the Trk/neutrophin pathway have been demonstrated to be highly effective in numerous pre-clinical animal models of pain. Antagonistic NGF and TrkA antibodies have been shown to be efficacious in inflammatory and neuropathic pain animal models and in human clinical trials. See Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; and Jaggar, S. I. et al. (199) *Br. J. Anaesth.* 83, 442-448. Through gene disruption studies in mice the TrkA-NGF interaction was found to be required for the survival of certain peripheral neuron populations involved in mediating pain signaling in the case of pancreatic cancer—an increase in the expression of TrkA was shown to correlate with an increase level of pain signaling (Zhu et al., *Journal of Clinical oncology,* 17: 2419-2428 (1999)). Increased expression of NGF and TrkA was also observed in human osteoarthritis chondrocytes (Iannone et al, *Rheumatology* 41: 1413-1418 (2002)). In particular, anti-TrkA antibodies and anti-NGF antibodies have been demonstrated to be effective analgesics in in vivo models of inflammatory and neuropathic pain. See WO2006/131952, WO2005/061540, EP1181318 and WO01/78698, WO2004/058184 and WO2005/019266, respectively. See also WO2004/096122 and WO2006/137106 which describe the use of an anti-TrkA antibody in combination with an opioid analgesic for the treatment or prevention of pain.

Trk inhibitors that can induce apoptosis of proliferating osteoblast may be useful in treating diseases related to an imbalance of the regulation of bone remodeling, such as osteoporosis, rheumatoid arthritis and bone metastases. The expression of TrKA and TrkC receptors in the bone forming area in mouse models of bone fracture and localization of NGF in almost all bone forming cells have been observed (K. Asaumi, et al., Bone (2000) 26(6) 625-633). See also Exper Opin. Ther. Patents (2009) 19(3)), WO2006/115452 and WO2006/087538, WO6123113, WO10033941, WO10077680, WO2005110994, *Investigational New Drugs* (2004), 22, 449-458 and R. Tripathy, et al., *Bioorg. Med. Chem. Lett.,* 2008, 18, 3551-3555. The association between overexpression, activation, amplification and/or mutation of Trks and several cancers as seen with studies conduct on neuroblastoma (Brodeur, G. M., Nat. Rev. Cancer 2003, 3, 203-216), ovarian cancer (Kruettgen et al., *Brain Pathology* 2006, 16: 304-310), prostate cancer (Dionne et al., Clin. Cancer Res. 1998, 4(8): 1887-1898), pancreatic cancer (Dang et al., *J of Gastroenterology and Hepatology* 2006, 21(5): 850-858), large cell neuroendocrine tumors (Marchetti et al., *Human Mutation* 2008, 29(5), 609-616, and colorectal cancer (Bardelli, A., *Science* 2003, 300, 949) support the reasoning that therapeutic implications of an effective Trk inhibitor may extend far beyond pain therapy. See also WO2005/030128, WO2012158413, WO07013673, WO07025540, WO08052734, WO2012028579, WO2012159565, WO2012107434, WO2012003387, WO2010111653, WO2008124610, WO2004098518, EP1388341, WO2012028579, WO2008003770, WO2012161879, WO2012100223, WO2009046802, WO2009003999, WO2007042321, US2005143384, WO2009003998, WO2007069773, WO2005/030128, US2010120862.

Also promising is the utility of Trk inhibitors in the treatment of inflammatory lung diseases such as asthma (Freund-Michel, V; et al., *Pharmacology & Therapeutics* (2008), 117(1), 52-76), interstitial cystitis (Hu Vivian Y; et. al., *J of Urology* (2005, 173(3), 1016-21), inflammatory bowel disease including ulcerative colitis and Chron's disease (Di Mola, F. F., et al., *Gut* (2000), 46(5), 670-678 and inflammatory skin diseases such as atopic dermatitis (Dou, Y. C., et. Al., *Archives of Dermatological Research* (2006), 298(1), 31-37, eczema and psoriasis (Raychaudhuri, S. P. et. al., *J of Investigative Dermatology* (2004), 122(3), 812-819).

Modulation of the neutrophin/Trk pathway also has been shown to have an effect in the etiology of neurodegenerative diseases including multiple sclerosis, Parkinson's disease and Alzheimer's disease (Sohrabji, et. al., *Neuroendocrinology* (2006), 27(4), 404-414).

Thus, the compounds of the invention, which are Trk inhibitors, are believed to be useful in the treatment of multiple types of acute and chronic pain including but not limited to inflammatory pain, neuropathic pain, and pain associated with cancer, surgery and bone fracture. The compounds may also useful in the treatment of cancer, inflammation, neurodegenerative diseases and certain infectious diseases.

SUMMARY OF THE INVENTION

The present invention is directed to compounds of generic formula (I) below or pharmaceutically acceptable salts thereof that are useful as a Trk kinase mediator of NGF driven biological responses, an inhibitor of TrkA as well as other Trk kinases.

The invention is further directed to methods of treating a patient (preferably a human) for diseases or disorders in which the NGF receptor Trk kinases are involved, in particular TrkA. The invention further involves use of the compounds as NGF receptor TrkA inhibitor and/or antagonist for the preparation of a medicament for the treatment and/or prevention of diseases associated with inhibiting TrkA, which includes pain, cancer, restenosis, atherosclerosis, psoriasis, thrombosis, or a disease, disorder, or injury relating to dysmyelination or demyelination. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

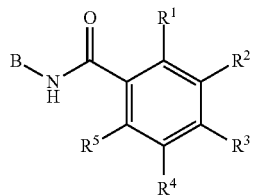

(I)

or a pharmaceutically acceptable salt thereof, wherein
B is selected from the group consisting of a bicyclic heteroaryl having at least one nitrogen heteroatom, said heteroaryl optionally substituted with 1 to 3 groups of $R^a$;
R is selected from the group consisting of hydrogen, OH, or $-C_{1-6}$alkyl;
$R^1$ and $R^5$ are independently selected from the group consisting of hydrogen, CN, OH, $C_{1-6}$alkyl, and halogen;
$R^2$ and $R^4$ are independently selected from the group consisting of hydrogen, halogen, $C_{1-4}$ haloalkyl, $C_{1-6}$ alkyl, $(CHR)_nC_{6-10}$ aryl and $(CHR)_nC_{5-10}$ heterocycle, said alkyl, aryl, and heterocycle optionally substituted with 1 to 3 groups of $R^a$;
$R^3$ is selected from the group consisting of hydrogen, $C_{1-6}$ alkyl, $C_{1-4}$ haloalkyl, $-OC_{1-4}$ haloalkyl, and halogen;
$R^a$ is selected from the group consisting of $-CN$, $NO_2$, $-C_{1-4}$ haloalkyl, $-OC_{1-6}$ alkyl, $-C_{1-6}$ alkenyl, $-C_{1-6}$ alkynyl, $-(CHR)_nC_{6-10}$ aryl, $-(CHR)_nC_{4-10}$ heterocycle, $-(CHR)_nC(O)(CHR)_nC_{4-10}$ heterocycle, $-O-(CH_2)_nC_{6-10}$ aryl, $-O-(CH_2)_nC_{4-10}$ heterocycle $-O-$, $-(CH_2)_nN(R^d)_2$, $-(CH_2)_nC(O)NH(CH_2)_nC_{4-10}$ heterocycle, $SO_2R^d$, $SO_2N(R^d)_2$, $-C(O)CF_3$, COR, $-(CH_2)_n$halo, $-(CH_2)_nNHC(O)R^d$, $-(CH_2)_nNHC(O)NHR^d$, $-(CH_2)_nNHC(O)OR^d$, $-(CHR)_nC(O)N(R^d)_2$, $-O-C_{1-6}$ alkyl, and $-OH$, said alkyl, aryl and heterocycle optionally substituted with 1 to 3 groups of $R^b$, wherein when two $R^d$ groups are attached to a nitrogen atom they may combine with that nitrogen to from a 4-8 membered heterocyle that is optionally substituted with 1 to 3 groups of $R^f$;
$R^b$ is selected from the group consisting of $-C_{1-6}$ alkyl, $-C_{1-6}$ alkyl OR, $-C_{1-4}$ haloalkyl, $-(CH_2)_nC_{3-6}$ cycloalkyl, $-(CH_2)_nN(R^d)_2$, $-(CH_2)_nOR^c$, $-O-$, halogen, $-CN$, $S(O)(NH)R^g$, $-SO_2R$, $-SO_2N(R^d)_2$, $-O-(CH_2)_nC_{4-10}$ heterocycle, $-(CH_2)_nC(O)N(R^d)_2$, $-(CH_2)_n$ NHC(O)$R^d$, $-C_{1-6}$ alkylN$(R^d)_2$, and halo, said cycloalkyl optionally substituted with 1 to 3 groups of $R^f$, and wherein when two $R^d$ groups are attached to a nitrogen atom they may combine with that nitrogen to from a 4-8 membered heterocyle that is optionally substituted with 1 to 3 groups of $R^f$;
$R^c$ is selected from the group consisting of hydrogen, $-C_{1-6}$ alkylOR$^g$, $-C_{1-4}$ haloalkyl and $-C_{1-6}$ alkyl;
$R^d$ is independently selected from the group consisting of hydrogen, $-C_{1-4}$ haloalkyl $-C_{1-6}$ alkyl, $-(CH_2)_n$NR$^j$C$_{4-10}$ heterocycle, $-(CH_2)_nC_{3-6}$cycloalkyl, and $-(CH_2)_nC_{4-10}$heterocycle said alkyl, cycloalkyl and heterocycle optionally substituted with 1 to 3 groups of Rf;
$R^f$ is selected from the group consisting of hydrogen, OR$^c$, CN, $-N(R^c)_2$, C(O)N(R$^g$)$_2$, C(O)C$_{1-6}$alkyl, $-SO_2R^g$, $-O-$, $-C_{1-6}$alkylSO$_2$R$^g$, $-C_{1-6}$alkylOR$^g$, $-C_{1-6}$alkylN(R$^g$)$_2$,
$R^g$ is selected from the group consisting of hydrogen, and $-C_{1-6}$alkyl; and n represents 0-6.

An embodiment of the invention of formula I is realized when B is a bicyclic heteroaryl selected from the group consisting of unsubstituted or substituted quinoxalinyl, indolyl, imidazopyridinyl, imidazothiazolyl, imidazopyrimidinyl, imidazopyridazinyl, andimidazothiadiazolyl.

Another embodiment of the invention of formula I is realized when B is pyrazolopyridinyl that is represented by structural formula (d) found below.

Another embodiment of the invention of formula I is realized when the five membered portion the bicycle of B is attached through a carbon atom to the benzamide.

Another embodiment of the invention of formula I is realized when B is unsubstituted or substituted imidazopyridinyl. Another embodiment of the invention of formula I is realized when B is unsubstituted or substituted imidazothiazolyl. Another embodiment of the invention of formula I is realized when B is unsubstituted or substituted imidazopyrimidinyl. Still another embodiment of the invention of formula I is realized when B is unsubstituted or substituted imidazopyridazinyl. Another embodiment of the invention of formula I is realized when B is unsubstituted or substituted imidazothiadiazolyl. Yet another embodiment of the invention of formula I is realized when B is unsubstituted or substituted quinoxalinyl. Another embodiment of the invention of formula I is realized when B is unsubstituted or substituted pyrazolopyridinyl that is represented by structural formula (d).

Another embodiment of the invention of formula I is realized when $R^a$ is selected from CN, $-C_{1-4}$haloalkyl, $-OC_{1-4}$haloalkyl, $-C_{1-6}$alkyl, $-(CHR)_nC_{6-10}$ aryl, $-(CHR)_nC_{5-10}$ heterocycle, $-C(O)(CHR)_nC_{5-10}$ heterocycle, $-C(O)CF_3$, C(O)R, C(O)N(R)$_2$, $-(CH_2)_nN(R)_2$, $SO_2R$, $SO_2N(R)_2$, $-(CH_2)_n$halogen, and $-OR$, said alkyl, aryl, and heterocycle optionally substituted with 1 to 3 groups of $R^b$. A subembodiment of this aspect of the invention is realized when $R^a$ is selected from CN, $-C_{1-4}$ haloalkyl, $-C_{1-6}$alkyl, $-(CHR)_nC_{6-10}$ aryl, $-(CHR)_nC_{5-10}$ heterocycle, $-C(O)(CHR)_nC_{5-10}$ heterocycle, halogen, and $-OR$ said alkyl, aryl, and heterocycle optionally substituted with 1 to 3 groups of $R^b$. Still a further aspect of the invention of formula I is realized when $R^a$ is selected from CN, and optionally substituted $-C_{1-6}$alkyl, CH$_2$azetidinyl, C(O)azetidinyl, phenyl, thiazolyl, pyridyl, isoxazolyl and oxazolyl, alkyl, azetidinyl, phenyl, thiazolyl, pyridyl, isoxazolyl and oxazolyl optionally substituted with 1 to 3 groups of $R^b$.

Another embodiment of the invention of formula I is realized when $R^b$ is selected from $-C_{1-6}$alkyl, OR$^c$, and halogen.

Still another embodiment of the invention of formula I is realized when $R^1$ and $R^5$ are both hydrogen. Another embodiment of the invention of formula I is realized when one of $R^1$ and $R^5$ is hydrogen and the other is halogen. Another embodiment of the invention of formula I is realized when one of $R^1$ and $R^5$ is hydrogen and the other is CN, OH, or $C_{1-6}$alkyl Yet another embodiment of the invention of formula I is realized when one of $R^1$ and $R^5$ hydrogen and the other is —$C_{1-6}$alkyl. Yet another embodiment of the invention of formula I is realized when one of $R^1$ and $R^5$ hydrogen and the other is OH.

Another embodiment of the invention of formula I is realized when at least one of $R^2$ and $R^4$ is $(CHR)_nC_{5-10}$ heterocycle optionally substituted with 1 to 3 groups of $R^a$.

Another embodiment of the invention of formula I is realized when one of $R^2$ and $R^4$ is hydrogen and the other is $(CHR)_nC_{5-10}$ heterocycle, said heterocycle optionally substituted with 1 to 3 groups of $R^a$. A subembodiment of this aspect of the invention is realized when the n in $(CHR)_nC_{5-10}$ heterocycle of $R^2$ and $R^4$ is zero. Another subembodiment of this aspect of the invention is realized when the optionally substituted heterocycle of $R^2$ and $R^4$ is a five or six membered ring containing one or more heteroatoms at least one of which is nitrogen. Still another subembodiment of this aspect of the invention is realized when the optionally substituted heterocycle of $R^2$ and $R^4$ is a five membered ring containing one or more heteroatoms at least one of which is nitrogen. Still another subembodiment of this aspect of the invention is realized when the optionally substituted heterocycle of $R^2$ and $R^4$ is a six membered ring containing one or more heteroatoms at least one of which is nitrogen. Another subembodiment of this aspect of the invention is realized when the heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Another subembodiment of this aspect of the invention is realized when the heterocycle of $R^2$ and $R^4$ is optionally substituted pyrazolyl. Another subembodiment of this aspect of the invention is realized when the heterocycle of $R^2$ and $R^4$ is substituted pyrazolyl. Still another subembodiment of this aspect of the invention is realized when the heterocycle of $R^2$ and $R^4$ is optionally substituted thiazolyl. Yet another subembodiment of this aspect of the invention is realized when the heterocycle of $R^2$ and $R^4$ is optionally substituted pyridyl. Yet another subembodiment of this aspect of the invention is realized when the heterocycle of $R^2$ and $R^4$ is optionally substituted oxadiazolyl. Yet another subembodiment of this aspect of the invention is realized when the heterocycle of $R^2$ and $R^4$ is optionally substituted oxazolyl. Yet another subembodiment of this aspect of the invention is realized when the heterocycle of $R^2$ and $R^4$ is optionally substituted pyrimidinyl. Yet another subembodiment of this aspect of the invention is realized when the heterocycle of $R^2$ and $R^4$ is optionally substituted triazolyl. Another subembodiment of this aspect of the invention is realized when the heterocycle of $R^2$ and $R^4$ is optionally substituted pyridazinyl. Another subembodiment of this aspect of the invention is realized when the heterocycle of $R^2$ and $R^4$ is optionally substituted pyrazinyl. Another subembodiment of this aspect of the invention is realized when the heterocycle of $R^2$ and $R^4$ is optionally substituted thiadiazolyl. Still another subembodiment of this aspect of the invention is realized when the heterocycle of $R^2$ and $R^4$ is optionally substituted with 1 to 3 groups of $R^a$ selected from CN, —$C_{1-4}$haloalkyl, —$C_{1-6}$alkyl, —$(CHR)_nC_{6-10}$ aryl, —$(CHR)_nC_{5-10}$ heterocycle, —$C(O)(CHR)_nC_{5-10}$ heterocycle, halogen, and —OR said alkyl, aryl, and heterocycle optionally substituted with 1 to 3 groups of $R^b$.

Another embodiment of the invention of formula I is realized when $R^2$ and $R^4$ both are hydrogen. Another embodiment of the invention of formula I is realized when one of $R^2$ and $R^4$ is hydrogen and the other is $CF_3$ or halogen.

Another embodiment of the invention of formula I is realized when $R^3$ is selected from the group consisting of hydrogen, $CF_3$, $OCF_3$, $CH_3$, chlorine, and fluorine. A subembodiment of this aspect of the invention is realized when $R^3$ is $CF_3$. Still another subembodiment of this aspect of the invention is realized when $R^3$ is $OCF_3$. Yet another subembodiment of this aspect of the invention is realized when $R^3$ is chlorine or fluorine.

Another embodiment of the invention of formula I is realized when B is represented by structural formulas (a), (b), (c), (d), (e), (f), and (g):

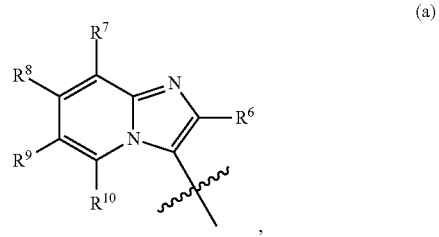

(a)

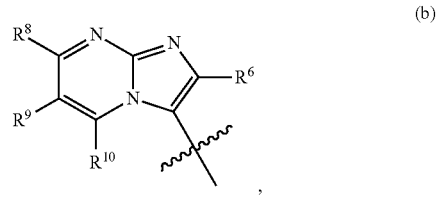

(b)

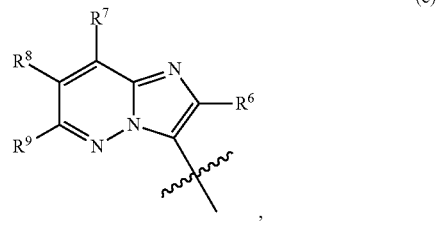

(c)

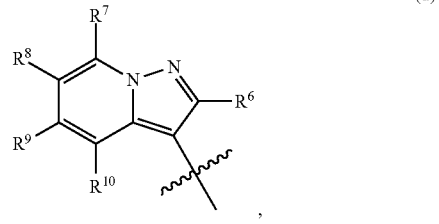

(d)

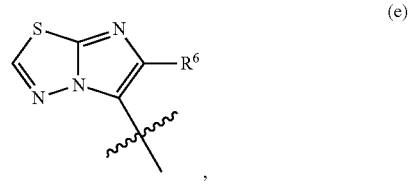

(e)

-continued (f)
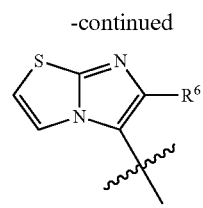

(g)
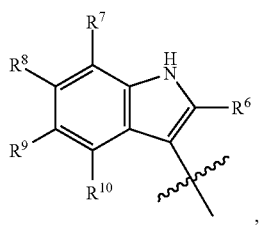

wherein:
R⁶ represents $(CH_2)_nC_{6-10}$aryl, or $(CH_2)_nC_{5-10}$heterocycle, said aryl, and heterocycle optionally substituted with 1 to 3 groups of $R^a$; and
$R^7$, $R^8$, $R^9$ and $R^{10}$ independently represent hydrogen, halogen, CN, $C_{1-6}$alkyl, $C(O)N(R)_2$, $C(O)(CH_2)_nC_{5-10}$heterocycle, $(CH_2)_nC_{6-10}$aryl, or $(CH_2)_nC_{5-10}$heterocycle, said alkyl, aryl, and heterocycle optionally substituted with 1 to 3 groups of $R^a$. A subembodiment of this aspect of the invention is realized when the $R^a$ substituents are selected from OR, halogen, $C_{1-6}$alkyl, and $N(R)_2$.

A subembodiment of the invention of formula I wherein B is represented by structural formulas (a), (b), (c), (d), (e), (f), or (g) is realized when $R^6$ is selected from the group consisting of unsubstituted or substituted phenyl, thiazolyl, pyrazolyl, pyridyl, isoxazoly, oxazolyl, and pyrimidinyl.

Another subembodiment of the invention of formula I wherein B is represented by structural formulas (a), (b), (c), (d), (e), (f), or (g) is realized when $R^8$ and $R^9$ are independently selected from hydrogen, halogen, CN, $CH_2OH$, $C(O)N(R)_2$, optionally substituted $C_{1-6}$alkyl, phenyl, pyrazolyl, isoxazolyl, oxazolyl, $(CH_2)_n$azetidinyl, and $C(O)NH$azetidinyl.

Another subembodiment of the invention of formula I wherein B is represented by structural formulas (a), (b), (c), (d), (e), (f), or (g) is realized when $R^7$ and $R^{10}$ are independently selected from hydrogen, $C_{1-6}$alkyl, and halogen, said alkyl optionally substituted with 1 to 3 groups of $R^a$. A subembodiment of this aspect of the invention is realized when the $R^a$ substituents are selected from OR, halogen, $C_{1-6}$alkyl, and $N(R)_2$.

Another embodiment of the invention of formula I is realized when B is imidazopyridinyl represented by structural formula (a).

Still another embodiment of the invention of formula I wherein B is imidazopyridinyl represented by structural formula (a) is realized when $R^6$ is unsubstituted or substituted phenyl, thiazolyl, pyrazolyl, pyridyl, isoxazoly, oxazolyl, and pyrimidinyl. A subembodiment of this aspect of the invention is realized when $R^6$ is unsubstituted phenyl. Another subembodiment of this aspect of the invention is realized when $R^6$ is substituted phenyl. Another subembodiment of this aspect of the invention is realized when $R^6$ is unsubstituted or substituted thiazolyl. Another subembodiment of this aspect of the invention is realized when $R^6$ is unsubstituted or substituted pyrazoly. Another subembodiment of this aspect of the invention is realized when $R^6$ is unsubstituted or substituted pyridyl. Another subembodiment of this aspect of the invention is realized when $R^6$ is unsubstituted or substituted prymidinyl. Another subembodiment of this aspect of the invention is realized when $R^6$ is unsubstituted or substituted isoxazolyl. Another subembodiment of this aspect of the invention is realized when $R^6$ is unsubstituted or substituted oxazolyl.

Another embodiment of the invention of formula I wherein B is imidazopyridinyl represented by structural formula (a) is realized when $R^8$ and $R^9$ are independently selected from hydrogen, halogen, CN, $CH_2OH$, $C(O)N(R)_2$, optionally substituted $C_{1-6}$alkyl, phenyl, pyrazolyl, isoxazolyl, oxazolyl, $(CH_2)_n$azetidinyl, and $C(O)NH$azetidinyl. A subembodiment of this aspect of the invention is realized when $R^8$ and $R^9$ are both hydrogen. Another subembodiment of this aspect of the invention is realized when one of $R^8$ and $R^9$ is hydrogen and the other is halogen, CN, $CH_2OH$, $C(O)N(R)_2$, optionally substituted $C_{1-6}$alkyl, phenyl, pyrazolyl, isoxazolyl, oxazolyl, $(CH_2)_n$azetidinyl, or $C(O)N$-Hazetidinyl.

Another embodiment of the invention of formula I wherein B is imidazopyridinyl represented by structural formula (a) is realized when $R^7$ and $R^{10}$ are independently selected from hydrogen, $C_{1-6}$alkyl, and halogen, said alkyl optionally substituted with 1 to 3 groups of $R^b$. A subembodiment of this invention is realized when both $R^7$ and $R^{10}$ are hydrogen.

Another embodiment of the invention of formula I wherein B is imidazopyridinyl represented by structural formula (a) is realized when $R^7$, $R^8$, $R^9$ and $R^{10}$ are all hydrogen.

Still another embodiment of the invention of formula I is represented by structural formula II, II
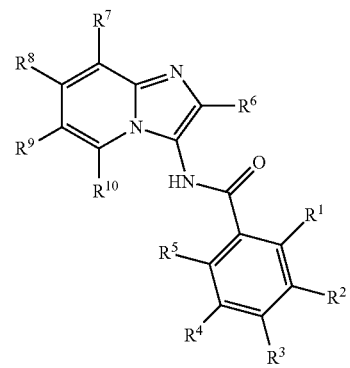

or a pharmaceutically acceptable salt thereof, wherein:
$R^1$ and $R^5$ are as originally described, $R^6$ is unsubstituted or substituted phenyl, thiazolyl, pyrazolyl, pyridyl, isoxazolyl, oxazolyl, or pyrimidinyl, $R^8$ and $R^9$ are independently selected from hydrogen, halogen, CN, $CH_2OH$, $C(O)N(R)_2$, optionally substituted $C_{1-6}$alkyl, phenyl, pyrazolyl, isoxazolyl, oxazolyl, $(CH_2)_n$azetidinyl, and $C(O)NH$azetidinyl, $R^7$ and $R^{10}$ are independently selected from hydrogen, $C_{1-6}$alkyl, and halogen, said alkyl optionally substituted with 1 to 3 groups selected from OR, halogen, $C_{1-6}$alkyl, and $N(R)_2$, $R^3$ is selected from the group consisting of hydrogen, $CF_3$, $OCF_3$, $CH_3$, chlorine, and fluorine, and one of $R^2$ and $R^4$ is hydrogen and the other is $(CHR)_nC_{5-10}$heterocycle, said heterocycle optionally substituted with 1 to 3 groups of $R^a$. A subembodiment of the invention of formula II is realized when $R^3$ is $CF_3$, one of $R^2$ and $R^4$ is hydrogen and the other is a (CHR)$_n$C$_{5-10}$heterocycle that is a five or six membered ring containing one or more heteroatoms at least one of which is nitrogen. Still another subembodiment of the invention of formula II is realized when the optionally substituted heterocycle of R$^2$ and R$^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of the invention of formula II is realized when the optionally substituted heterocycle of R$^2$ and R$^4$ is pyrazolyl, R$^6$ is optionally substituted phenyl and R$^3$ is CF$_3$.

Another embodiment of the invention of formula I is realized when B is optionally imidazopyrimidinyl represented by structural formula (b).

Still another embodiment of the invention of formula I wherein B is imidazopyrimidinyl represented by structural formula (b) is realized when R$^6$ is unsubstituted or substituted phenyl, thiazolyl, pyrazolyl, pyridyl, isoxazoly, oxazolyl, and pyrimidinyl. A subembodiment of this aspect of the invention is realized when R$^6$ is unsubstituted phenyl. Another subembodiment of this aspect of the invention is realized when R$^6$ is substituted phenyl. Another subembodiment of this aspect of the invention is realized when R$^6$ is unsubstituted or substituted thiazolyl. Another subembodiment of this aspect of the invention is realized when R$^6$ is unsubstituted or substituted pyrazoly. Another subembodiment of this aspect of the invention is realized when R$^6$ is unsubstituted or substituted pyridyl. Another subembodiment of this aspect of the invention is realized when R$^6$ is unsubstituted or substituted prymidinyl. Another subembodiment of this aspect of the invention is realized when R$^6$ is unsubstituted or substituted isoxazolyl. Another subembodiment of this aspect of the invention is realized when R$^6$ is unsubstituted or substituted oxazolyl.

Another embodiment of the invention of formula I wherein B is imidazopyrimidinyl represented by structural formula (b) is realized when R$^8$ and R$^9$ are independently selected from hydrogen, halogen, CN, CH$_2$OH, C(O)N(R)$_2$, optionally substituted C$_{1-6}$alkyl, phenyl, pyrazolyl, isoxazolyl, oxazolyl, (CH$_2$)$_n$azetidinyl, and C(O)NHazetidinyl. A subembodiment of this aspect of the invention is realized when R$^8$ and R$^9$ are both hydrogen. Another subembodiment of this aspect of the invention is realized when one of R$^8$ and R$^9$ is hydrogen and the other is halogen, CN, CH$_2$OH, C(O)N(R)$_2$, optionally substituted C$_{1-6}$alkyl, phenyl, pyrazolyl, isoxazolyl, oxazolyl, (CH$_2$)$_n$azetidinyl, or C(O)N-Hazetidinyl.

Another embodiment of the invention of formula I wherein B is imidazopyrimidinyl represented by structural formula (b) is realized when R$^7$ and R$^{10}$ are independently selected from hydrogen, C$_{1-6}$alkyl, and halogen, said alkyl optionally substituted with 1 to 3 groups of R$^b$. A subembodiment of this invention is realized when both R$^7$ and R$^{10}$ are hydrogen.

Another embodiment of the invention of formula I wherein B is imidazopyrimidinyl represented by structural formula (b) is realized when R$^7$, R$^8$, R$^9$ and R$^{10}$ are all hydrogen.

Another embodiment of the invention of formula I is represented by structural formula III when B is imidazopyrimidinyl.

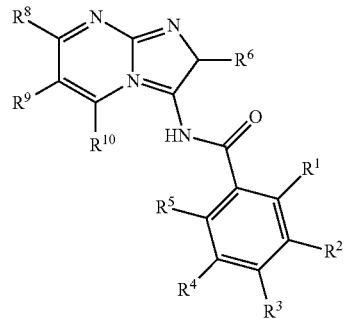

or a pharmaceutically acceptable salt thereof, wherein R$^1$ and R$^5$ are as originally described, R$^6$ is unsubstituted or substituted phenyl, thiazolyl, pyrazolyl, pyridyl, isoxazoly, oxazolyl, or pyrimidinyl, R$^8$ and R$^9$ are independently selected from hydrogen, halogen, CN, CH$_2$OH, C(O)N(R)$_2$, optionally substituted C$_{1-6}$alkyl, phenyl, pyrazolyl, isoxazolyl, oxazolyl, (CH$_2$)$_n$azetidinyl, and C(O)NHazetidinyl, R$^7$ and R$^{10}$ are independently selected from hydrogen, C$_{1-6}$alkyl, and halogen, said alkyl optionally substituted with 1 to 3 groups selected from OR, halogen, C$_{1-6}$alkyl, and N(R)$_2$, R$^3$ is selected from the group consisting of hydrogen, CF$_3$, OCF$_3$, CH$_3$, chlorine, and fluorine, and one of R$^2$ and R$^4$ is hydrogen and the other is (CHR)$_n$C$_{5-10}$ heterocycle, said heterocycle optionally substituted with 1 to 3 groups of R$^a$. Another subembodiment of this aspect of the invention of formula III is realized when R$^3$ is CF$_3$, one of R$^2$ and R$^4$ is hydrogen and the other is a (CHR)$_n$C$_{5-10}$ heterocycle that is a five or six membered ring containing one or more heteroatoms at least one of which is nitrogen. Still another subembodiment of this aspect of the invention of formula III is realized when the optionally substituted heterocycle of R$^2$ and R$^4$ is selected from the group consisting of pyrazolyl, pyridyl, thiazolyl, oxazolyl, pyrimidinyl, and triazolyl, said groups optionally substituted. Yet another subembodiment of this aspect of the invention of formula III is realized when the optionally substituted heterocycle of R$^2$ and R$^4$ is pyrazolyl, R$^6$ is optionally substituted phenyl and R$^3$ is CF$_3$.

Another embodiment of the invention of formula I is realized when B is imidazopyridazinyl represented by structural formula (c). A subembodiment of this aspect of the invention of formula I when B is imidazopyridazinyl is realized when R$^6$ is unsubstituted or substituted phenyl, thiazolyl, pyrazolyl, pyridyl, isoxazolyl, oxazolyl, or pyrimidinyl, R$^8$ and R$^9$ are independently selected from hydrogen, halogen, CN, CH$_2$OH, C(O)N(R)$_2$, optionally substituted C$_{1-6}$alkyl, phenyl, pyrazolyl, isoxazolyl, oxazolyl, (CH$_2$)$_n$ azetidinyl, and C(O)NHazetidinyl, R$^7$ is selected from hydrogen, C$_{1-6}$alkyl, and halogen, said alkyl optionally substituted with 1 to 3 groups of R$^b$, R$^3$ is selected from the group consisting of hydrogen, CF$_3$, OCF$_3$, CH$_3$, and fluorine, and one of R$^2$ and R$^4$ is hydrogen and the other is (CHR)$_n$C$_{5-10}$ heterocycle, said heterocycle optionally substituted with 1 to 3 groups of R$^a$. Another subembodiment of this aspect of the invention of formula I when B is imidazopyridazinyl is realized when R$^3$ is CF$_3$, one of R$^2$ and R$^4$ is hydrogen and the other is a (CHR)$_n$C$_{5-10}$ heterocycle that is a five or six membered ring containing one or more heteroatoms at least one of which is nitrogen. Still another subembodiment of this aspect of the invention of formula I when B is imidazopyridazinyl is realized when the optionally substituted heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of this aspect of the invention of formula I when B is imidazopyridazinyl is realized when the optionally substituted heterocycle of $R^2$ and $R^4$ is pyrazolyl, $R^6$ is optionally substituted phenyl and $R^3$ is $CF_3$.

Another embodiment of the invention of formula I is realized when B is pyrazolopyridinyl represented by structural formula (d). A subembodiment of this aspect of the invention of formula I when B is pyrazolopyridinyl of structural formula (d) is realized when $R^6$ is unsubstituted or substituted phenyl, thiazolyl, pyrazolyl, pyridyl, isoxazolyl, oxazolyl, or pyrimidinyl, $R^8$ and $R^9$ are independently selected from hydrogen, halogen, CN, $CH_2OH$, $C(O)N(R)_2$, optionally substituted $C_{1-6}$alkyl, phenyl, pyrazolyl, isoxazolyl, oxazolyl, $(CH_2)_n$azetidinyl, and C(O)NHazetidinyl, $R^{10}$ is selected from hydrogen, $C_{1-6}$alkyl, and halogen, said alkyl optionally substituted with 1 to 3 groups of $R^b$, $R^3$ is selected from the group consisting of hydrogen, $CF_3$, $OCF_3$, $CH_3$, and fluorine, and one of $R^2$ and $R^4$ is hydrogen and the other is $(CHR)_nC_{5-10}$ heterocycle, said heterocycle optionally substituted with 1 to 3 groups of $R^a$. Another subembodiment of this aspect of the invention of formula I when B is pyrazolopyridinyl of structural formula (d) is realized when $R^3$ is $CF_3$, one of $R^2$ and $R^4$ is hydrogen and the other is a $(CHR)_nC_{5-10}$ heterocycle that is a five or six membered ring containing one or more heteroatoms at least one of which is nitrogen. Still another subembodiment of this aspect of the invention of formula I when B is pyrazolopyridinyl of structural formula (d) is realized when the optionally substituted heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of this aspect of the invention of formula I when B is pyrazolopyridinyl of structural formula (d) is realized when the optionally substituted heterocycle of $R^2$ and $R^4$ is pyrazolyl, $R^6$ is optionally substituted phenyl and $R^3$ is $CF_3$.

Another embodiment of the invention of formula I is realized when B is imidazothiadiazolyl represented by structural formula (e). A subembodiment of this aspect of the invention of formula I when B is imidazothiadiazolyl is realized when $R^6$ is unsubstituted or substituted phenyl, thiazolyl, pyrazolyl, pyridyl, isoxazolyl, oxazolyl, or pyrimidinyl, $R^3$ is selected from the group consisting of hydrogen, $CF_3$, $OCF_3$, $CH_3$, and fluorine, and one of $R^2$ and $R^4$ is hydrogen and the other is $(CHR)_nC_{5-10}$ heterocycle, said heterocycle optionally substituted with 1 to 3 groups of $R^a$. Another subembodiment of this aspect of the invention of formula I when B is imidazothiadiazolyl is realized when $R^3$ is $CF_3$, one of $R^2$ and $R^4$ is hydrogen and the other is a $(CHR)_nC_{5-10}$ heterocycle that is a five or six membered ring containing one or more heteroatoms at least one of which is nitrogen. Still another subembodiment of this aspect of the invention of formula I when B is imidazothiadiazolyl is realized when the optionally substituted heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of this aspect of the invention of formula I when B is imidazothiadiazolyl is realized when the optionally substituted heterocycle of $R^2$ and $R^4$ is pyrazolyl, $R^6$ is optionally substituted phenyl and $R^3$ is $CF_3$.

Another embodiment of the invention of formula I is realized when B is imidazothiazolyl represented by structural formula (f). A subembodiment of this aspect of the invention is realized when $R^6$ is unsubstituted or substituted phenyl, thiazolyl, pyrazolyl, pyridyl, isoxazolyl, oxazoyl, or pyrimidinyl. Another subembodiment of this aspect of the invention of formula I when B is imidazothiazolyl is realized when $R^3$ is $CF_3$, one of $R^2$ and $R^4$ is hydrogen and the other is a $(CHR)_nC_{5-10}$ heterocycle that is a five or six membered ring containing one or more heteroatoms at least one of which is nitrogen. Still another subembodiment of this aspect of the invention of formula I when B is imidazothiazolyl is realized when the optionally substituted heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of this aspect of the invention of formula I when B is imidazothiazolyl is realized when the optionally substituted heterocycle of $R^2$ and $R^4$ is pyrazolyl, $R^6$ is optionally substituted phenyl and $R^3$ is $CF_3$.

Another embodiment of the invention of formula I is realized when B is indolyl represented by structural formula (g). A subembodiment of this aspect of the invention of formula I when B is indolyl is realized when $R^6$ is unsubstituted or substituted phenyl, thiazolyl, pyrazolyl, pyridyl, isoxazolyl, oxazolyl, or pyrimidinyl, $R^3$ is selected from the group consisting of hydrogen, $CF_3$, $OCF_3$, $CH_3$, and fluorine, and one of $R^2$ and $R^4$ is hydrogen and the other is $(CHR)_nC_{5-10}$ heterocycle, said heterocycle optionally substituted with 1 to 3 groups of $R^a$. Another subembodiment of this aspect of the invention of formula I when B is indolyl is realized when $R^3$ is $CF_3$, one of $R^2$ and $R^4$ is hydrogen and the other is a $(CHR)_nC_{5-10}$ heterocycle that is a five or six membered ring containing one or more heteroatoms at least one of which is nitrogen. Still another subembodiment of this aspect of the invention of formula I when B is indolyl is realized when the optionally substituted heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Yet another subembodiment of this aspect of the invention of formula I when B is indolyl is realized when the optionally substituted heterocycle of $R^2$ and $R^4$ is pyrazolyl, $R^6$ is optionally substituted phenyl and $R^3$ is $CF_3$.

Examples of compounds of this invention include those in Table 1:

TABLE 1

| Compound Number | Structure | Compound Name | LCMS (M + 1) |
|---|---|---|---|
| 1 | 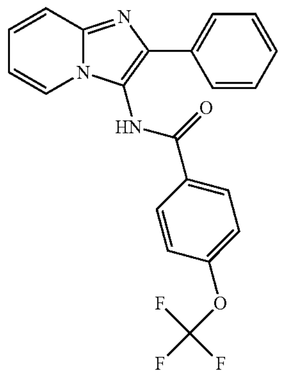 [SMILES: O=C(Nc1c(-c2ccccc2)nc2ccccn12)c1ccc(OC(F)(F)F)cc1] | N-(2-phenylimidazo[1,2-a]pyridin-3-yl)-4-(trifluoromethoxy)benzamide | 398.3 |
| 2 | 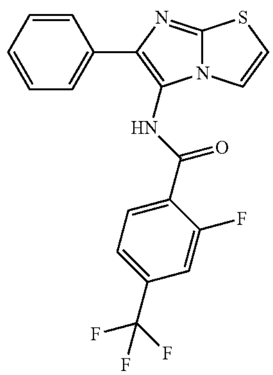 [SMILES: O=C(Nc1c(-c2ccccc2)nc2sccn12)c1ccc(C(F)(F)F)cc1F] | 2-fluoro-N-(6-phenylimidazo[2,1-b][1,3]thiazol-5-yl)-4-(trifluoromethyl)benzamide | 406.2 |
| 3 | 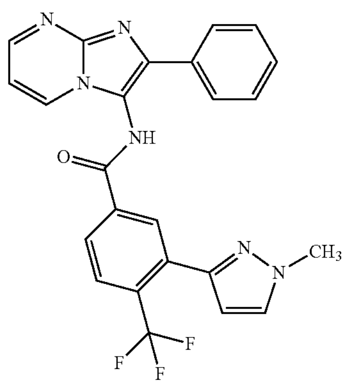 [SMILES: Cn1ccc(-c2cc(C(=O)Nc3c(-c4ccccc4)nc4ncccn34)ccc2C(F)(F)F)n1] | 3-(1-methyl-1H-pyrazol-3-yl)-N-(2-phenylimidazo[1,2-a]pyrimidin-3-yl)-4-(trifluoromethyl)benzamide | 463.1 |
| 4 | 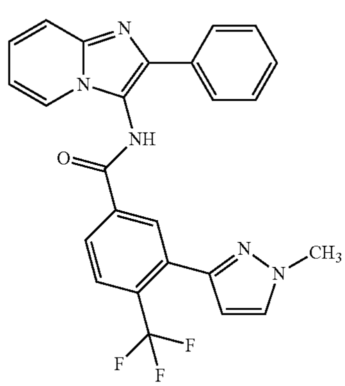 [SMILES: Cn1ccc(-c2cc(C(=O)Nc3c(-c4ccccc4)nc4ccccn34)ccc2C(F)(F)F)n1] | 3-(1-methyl-1H-pyrazol-3-yl)-N-(2-phenylimidazo[1,2-a]pyridin-3-yl)-4-(trifluoromethyl)benzamide | 462.2 |

TABLE 1-continued

| Compound Number | Structure | Compound Name | LCMS (M + 1) |
|---|---|---|---|
| 5 | 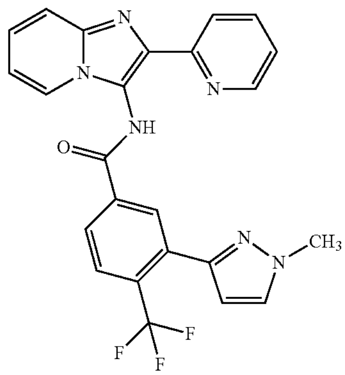 [SMILES: Cn1ccc(-c2cc(C(=O)Nc3c(-c4ccccn4)nc4ccccn34)ccc2C(F)(F)F)n1] | 3-(1-methyl-1H-pyrazol-3-yl)-N-(2-pyridin-2-ylimidazo[1,2-a]pyridin-3-yl)-4-(trifluoromethyl)benzamide | 463.0 |
| 6 | 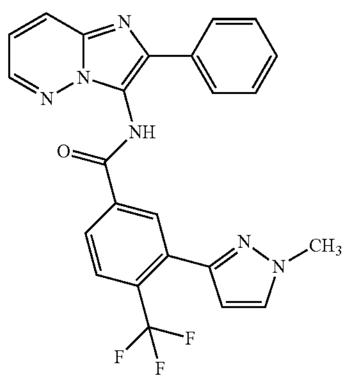 [SMILES: Cn1ccc(-c2cc(C(=O)Nc3c(-c4ccccc4)nc4cccnn34)ccc2C(F)(F)F)n1] | 3-(1-methyl-1H-pyrazol-3-yl)-N-(2-phenylimidazo[1,2-b]pyridazin-3-yl)-4-(trifluoromethyl)benzamide | 463.1 |
| 7 | 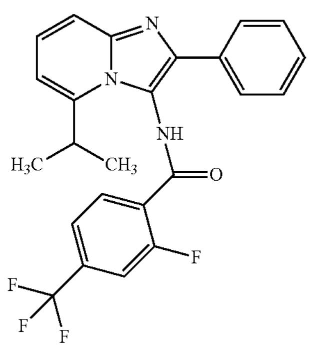 [SMILES: CC(C)c1cccc2nc(-c3ccccc3)c(NC(=O)c3ccc(C(F)(F)F)cc3F)n12] | 2-fluoro-N-[5-(1-methylethyl)-2-phenylimidazo[1,2-a]pyridin-3-yl]-4-(trifluoromethyl)benzamide | 442.1 |
| 8 | 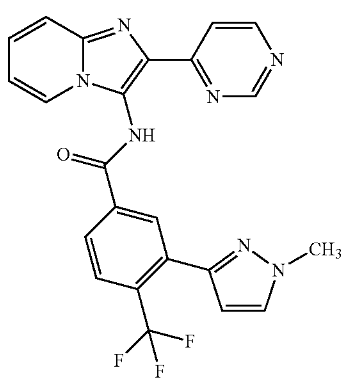 [SMILES: Cn1ccc(-c2cc(C(=O)Nc3c(-c4ccncn4)nc4ccccn34)ccc2C(F)(F)F)n1] | 3-(1-methyl-1H-pyrazol-3-yl)-N-(2-pyrimidin-4-ylimidazo[1,2-a]pyridin-3-yl)-4-(trifluoromethyl)benzamide | 464.0 |

TABLE 1-continued

| Compound Number | Structure | Compound Name | LCMS (M + 1) |
|---|---|---|---|
| 9 | 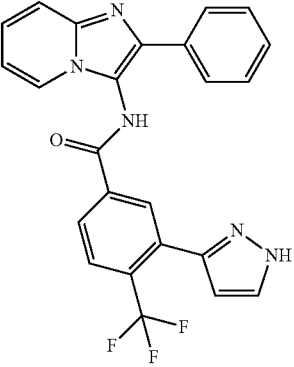 [SMILES: O=C(Nc1c(-c2ccccc2)nc2ccccn12)c1ccc(C(F)(F)F)c(-c2cc[nH]n2)c1] | N-(2-phenylimidazo[1,2-a]pyridin-3-yl)-3-(1H-pyrazol-3-yl)-4-(trifluoromethyl)benzamide | 448.0 |
| 10 | 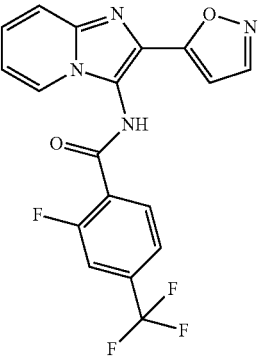 [SMILES: O=C(Nc1c(-c2ccno2)nc2ccccn12)c1ccc(C(F)(F)F)cc1F] | 2-fluoro-N-(2-isoxazol-5-ylimidazo[1,2-a]pyridin-3-yl)-4-(trifluoromethyl)benzamide | 391.2 |
| 11 | 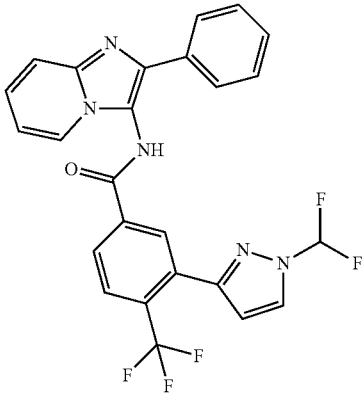 [SMILES: O=C(Nc1c(-c2ccccc2)nc2ccccn12)c1ccc(C(F)(F)F)c(-c2ccn(C(F)F)n2)c1] | 3-[1-(difluoromethyl)-1H-pyrazol-3-yl]-N-(2-phenylimidazo[1,2-a]pyridin-3-yl)-4-(trifluoromethyl)benzamide | 498.0 |
| 12 | 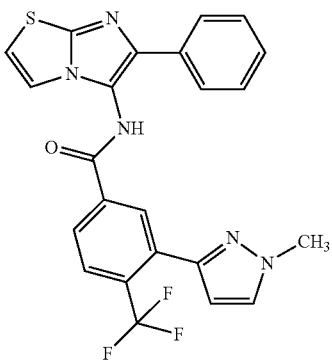 [SMILES: Cn1ccc(-c2cc(C(=O)Nc3c(-c4ccccc4)nc4sccn34)ccc2C(F)(F)F)n1] | 3-(1-methyl-1H-pyrazol-3-yl)-N-(6-phenylimidazo[2,1-b][1,3]thiazol-5-yl)-4-(trifluoromethyl)benzamide | 468.0 |

TABLE 1-continued

| Compound Number | Structure | Compound Name | LCMS (M + 1) |
|---|---|---|---|
| 13 | 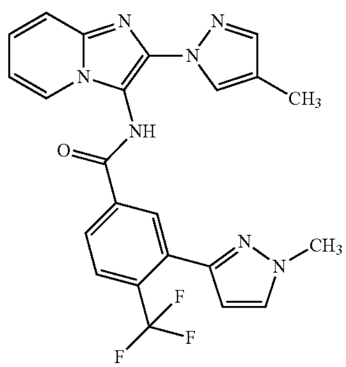 [SMILES: Cc1cnn(-c2nc3ccccn3c2NC(=O)c2ccc(C(F)(F)F)c(-c3ccn(C)n3)c2)c1] | 3-(1-methyl-1H-pyrazol-3-yl)-N-[2-(4-methyl-1H-pyrazol-1-yl)imidazo[1,2-a]pyridin-3-yl]-4-(trifluoromethyl)benzamide | 466.0 |
| 14 | 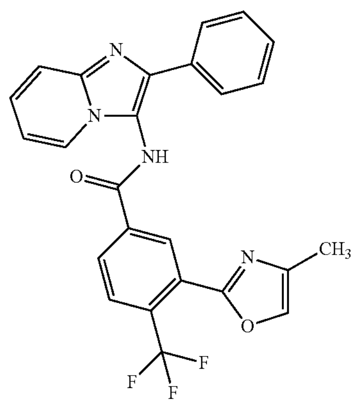 [SMILES: Cc1coc(-c2cc(C(=O)Nc3c(-c4ccccc4)nc4ccccn34)ccc2C(F)(F)F)n1] | 3-(4-methyl-1,3-oxazol-2-yl)-N-(2-phenylimidazo[1,2-a]pyridin-3-yl)-4-(trifluoromethyl)benzamide | 463.0 |
| 15 | 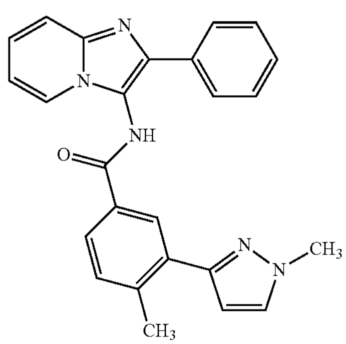 [SMILES: Cc1ccc(C(=O)Nc2c(-c3ccccc3)nc3ccccn23)cc1-c1ccn(C)n1] | 4-methyl-3-(1-methyl-1H-pyrazol-3-yl)-N-(2-phenylimidazo[1,2-a]pyridin-3-yl)benzamide | 408.0 |
| 16 | 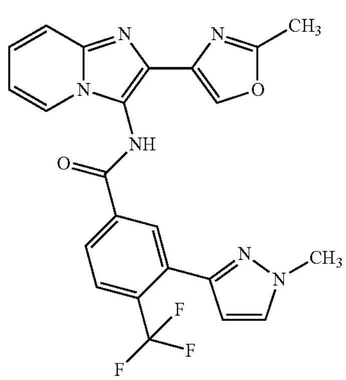 [SMILES: Cc1nc(-c2nc3ccccn3c2NC(=O)c2ccc(C(F)(F)F)c(-c3ccn(C)n3)c2)co1] | N-[2-(2-methyl-1,3-oxazol-4-yl)imidazo[1,2-a]pyridin-3-yl]-3-(1-methyl-1H-pyrazol-3-yl)-4-(trifluoromethyl)benzamide | 467.0 |

TABLE 1-continued

| Compound Number | Structure | Compound Name | LCMS (M + 1) |
|---|---|---|---|
| 17 | 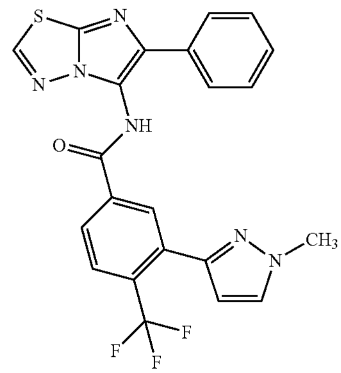 [SMILES: Cn1ccc(-c2cc(C(=O)Nc3c(-c4ccccc4)nc4scnn34)ccc2C(F)(F)F)n1] | 3-(1-methyl-1H-pyrazol-3-yl)-N-(6-phenylimidazo[2,1-b][1,3,4]thiadiazol-5-yl)-4-(trifluoromethyl)benzamide | 469.1 |
| 18 | 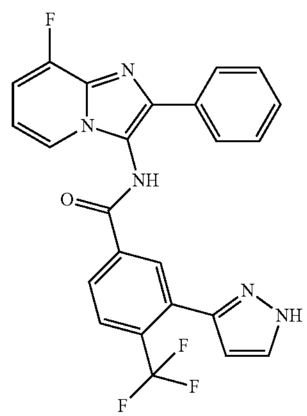 [SMILES: O=C(Nc1c(-c2ccccc2)nc2c(F)cccn12)c1ccc(C(F)(F)F)c(-c2cc[nH]n2)c1] | N-(8-fluoro-2-phenylimidazo[1,2-a]pyridin-3-yl)-3-(1H-pyrazol-3-yl)-4-(trifluoromethyl)benzamide | 466.1 |
| 19 | 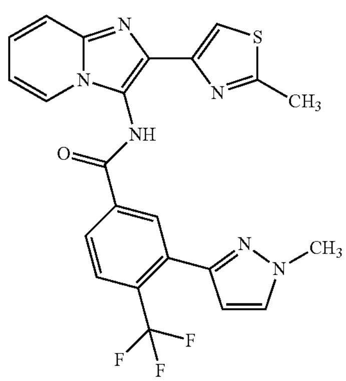 [SMILES: Cc1nc(-c2nc3ccccn3c2NC(=O)c2ccc(C(F)(F)F)c(-c3ccn(C)n3)c2)cs1] | 3-(1-methyl-1H-pyrazol-3-yl)-N-[2-(2-methyl-1,3-thiazol-4-yl)imidazo[1,2-a]pyridin-3-yl]-4-(trifluoromethyl)benzamide | 483.1 |
| 20 | 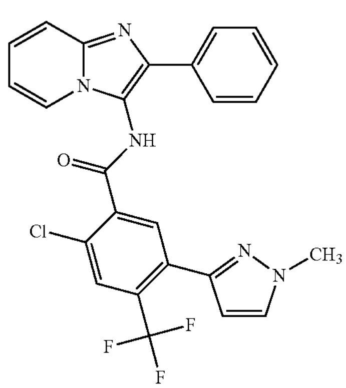 [SMILES: Cn1ccc(-c2cc(C(=O)Nc3c(-c4ccccc4)nc4ccccn34)c(Cl)cc2C(F)(F)F)n1] | 2-chloro-5-(1-methyl-1H-pyrazol-3-yl)-N-(2-phenylimidazo[1,2-a]pyridin-3-yl)-4-(trifluoromethyl)benzamide | 496.1 |

TABLE 1-continued

| Compound Number | Structure | Compound Name | LCMS (M + 1) |
|---|---|---|---|
| 21 | 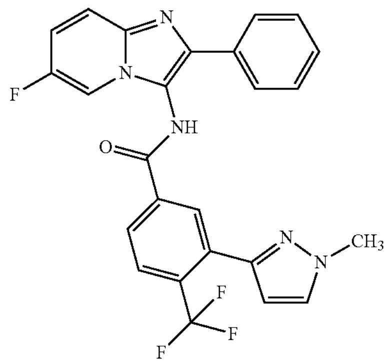 [SMILES: Cn1ccc(-c2cc(C(=O)Nc3c(-c4ccccc4)nc4ccc(F)cn34)ccc2C(F)(F)F)n1] | N-(6-fluoro-2-phenylimidazo[1,2-a]pyridin-3-yl)-3-(1-methyl-1H-pyrazol-3-yl)-4-(trifluoromethyl)benzamide | 480.1 |
| 22 | 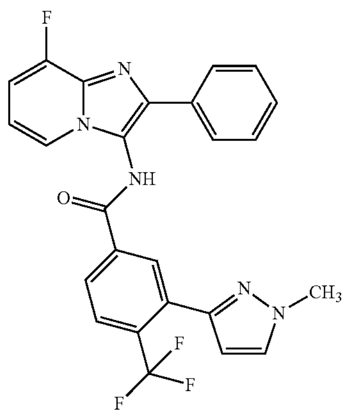 [SMILES: Cn1ccc(-c2cc(C(=O)Nc3c(-c4ccccc4)nc4c(F)cccn34)ccc2C(F)(F)F)n1] | N-(8-fluoro-2-phenylimidazo[1,2-a]pyridin-3-yl)-3-(1-methyl-1H-pyrazol-3-yl)-4-(trifluoromethyl)benzamide | 480.2 |
| 23 | 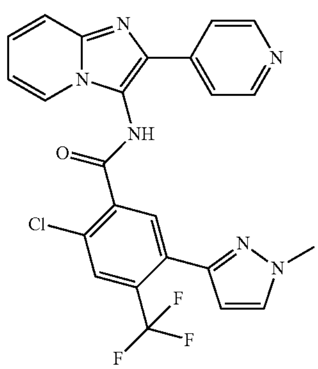 [SMILES: Cn1ccc(-c2cc(C(=O)Nc3c(-c4ccncc4)nc4ccccn34)c(Cl)cc2C(F)(F)F)n1] | 2-chloro-5-(1-methyl-1H-pyrazol-3-yl)-N-(2-pyridin-4-ylimidazo[1,2-a]pyridin-3-yl)-4-(trifluoromethyl)benzamide | 497.1 |
| 24 | 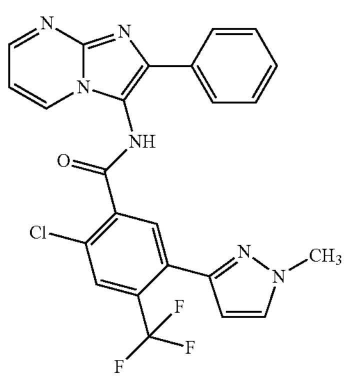 [SMILES: Cn1ccc(-c2cc(C(=O)Nc3c(-c4ccccc4)nc4ncccn34)c(Cl)cc2C(F)(F)F)n1] | 2-chloro-5-(1-methyl-1H-pyrazol-3-yl)-N-(2-phenylimidazo[1,2-a]pyrimidin-3-yl)-4-(trifluoromethyl)benzamide | 497.1 |

TABLE 1-continued

| Compound Number | Structure | Compound Name | LCMS (M + 1) |
|---|---|---|---|
| 25 | 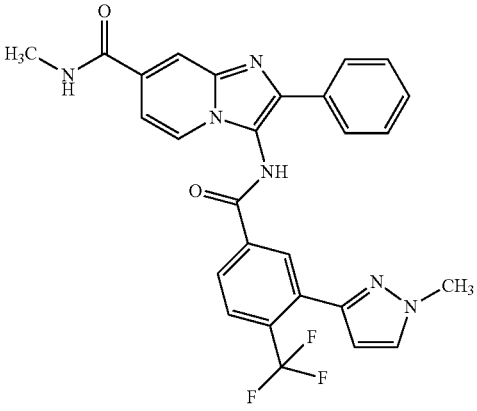 | N-methyl-3-({[3-(1-methyl-1H-pyrazol-3-yl)-4-(trifluoromethyl)phenyl]carbonyl}amino)-2-phenylimidazo[1,2-a]pyridine-7-carboxamide | 519.4 |
| 26 | 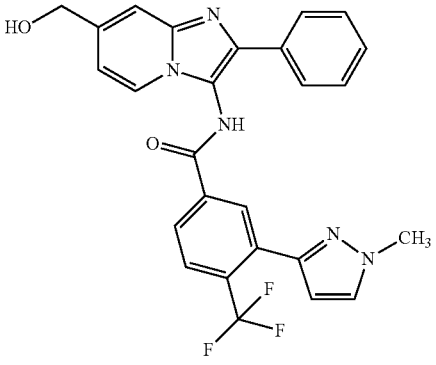 [SMILES: Cn1ccc(-c2cc(C(=O)Nc3c(-c4ccccc4)nc4cc(CO)ccn34)ccc2C(F)(F)F)n1] | N-[7-(hydroxymethyl)-2-phenylimidazo[1,2-a]pyridin-3-yl]-3-(1-methyl-1H-pyrazol-3-yl)-4-(trifluoromethyl)benzamide | 492.2 |
| 27 | 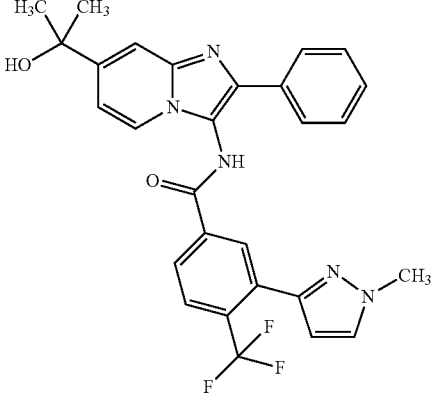 [SMILES: Cn1ccc(-c2cc(C(=O)Nc3c(-c4ccccc4)nc4cc(C(C)(C)O)ccn34)ccc2C(F)(F)F)n1] | N-[7-(1-hydroxy-1-methylethyl)-2-phenylimidazo[1,2-a]pyridin-3-yl]-3-(1-methyl-1H-pyrazol-3-yl)-4-(trifluoromethyl)benzamide | 520.2 |

TABLE 1-continued

| Compound Number | Structure | Compound Name | LCMS (M + 1) |
|---|---|---|---|
| 28 | 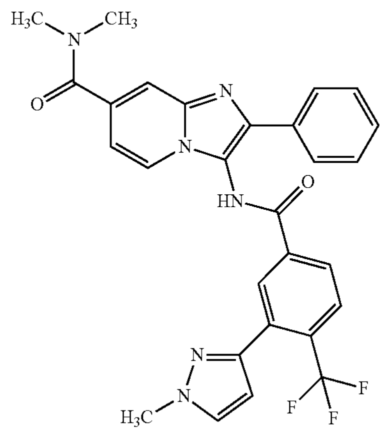 [SMILES: CN(C)C(=O)c1ccn2c(NC(=O)c3ccc(C(F)(F)F)c(-c4ccn(C)n4)c3)c(-c3ccccc3)nc2c1] | N,N-dimethyl-3-({[3-(1-methyl-1H-pyrazol-3-yl)-4-(trifluoromethyl)phenyl]carbonyl}amino)-2-phenylimidazo[1,2-a]pyridine-7-carboxamide | 533.4 |
| 29 | 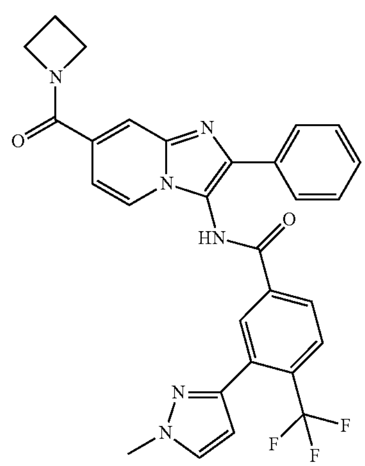 [SMILES: Cn1ccc(-c2cc(C(=O)Nc3c(-c4ccccc4)nc4cc(C(=O)N5CCC5)ccn34)ccc2C(F)(F)F)n1] | N-[7-(azetidin-1-ylcarbonyl)-2-phenylimidazo[1,2-a]pyridin-3-yl]-3-(1-methyl-1H-pyrazol-3-yl)-4-(trifluoromethyl)benzamide | 545.4 |
| 30 | 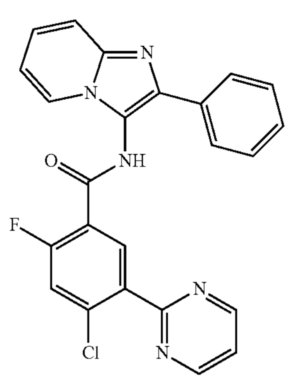 [SMILES: O=C(Nc1c(-c2ccccc2)nc2ccccn12)c1cc(-c2ncccn2)c(Cl)cc1F] | 4-chloro-2-fluoro-N-(2-phenylimidazo[1,2-a]pyridin-3-yl)-5-pyrimidin-2-ylbenzamide | 444.0 |

TABLE 1-continued

| Compound Number | Structure | Compound Name | LCMS (M + 1) |
|---|---|---|---|
| 31 | 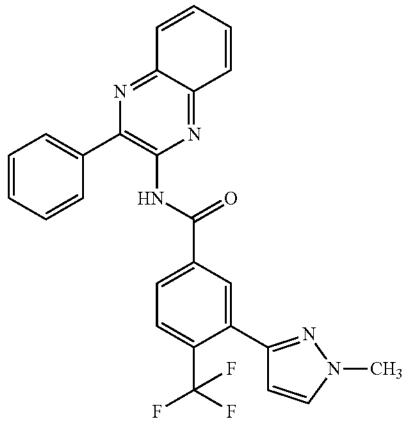 [SMILES: Cn1ccc(-c2cc(C(=O)Nc3nc4ccccc4nc3-c3ccccc3)ccc2C(F)(F)F)n1] | 3-(1-methyl-1H-pyrazol-3-yl)-N-(3-phenylquinoxalin-2-yl)-4-(trifluoromethyl)benzamide | 474.2 |
| 32 | 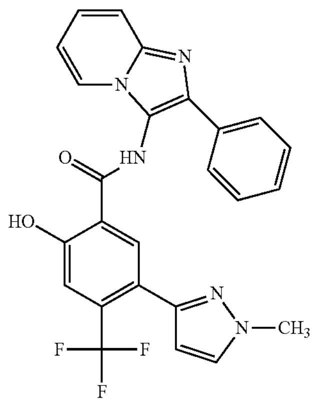 [SMILES: Cn1ccc(-c2cc(C(=O)Nc3c(-c4ccccc4)nc4ccccn34)c(O)cc2C(F)(F)F)n1] | 2-hydroxy-5-(1-methyl-1H-pyrazol-3-yl)-N-(2-phenylimidazo[1,2-a]pyridin-3-yl)-4-(trifluoromethyl)benzamide | 478.2 |
| 33 | 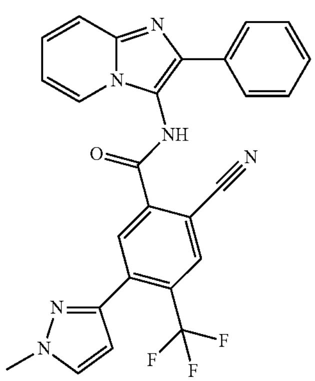 [SMILES: Cn1ccc(-c2cc(C(=O)Nc3c(-c4ccccc4)nc4ccccn34)c(C#N)cc2C(F)(F)F)n1] | 2-cyano-5-(1-methyl-1H-pyrazol-3-yl)-N-(2-phenylimidazo[1,2-a]pyridin-3-yl)-4-(trifluoromethyl)benzamide | 487.2 |
| 34 | 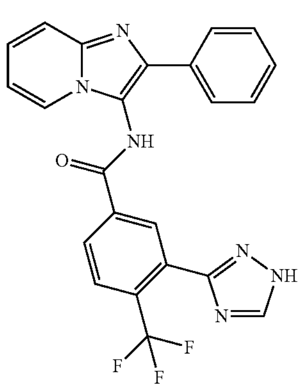 [SMILES: O=C(Nc1c(-c2ccccc2)nc2ccccn12)c1ccc(C(F)(F)F)c(-c2nc[nH]n2)c1] | N-(2-phenylimidazo[1,2-a]pyridin-3-yl)-3-(1H-1,2,4-triazol-3-yl)-4-(trifluoromethyl)benzamide | 449.2 |

TABLE 1-continued

| Compound Number | Structure | Compound Name | LCMS (M + 1) |
|---|---|---|---|
| 35 | 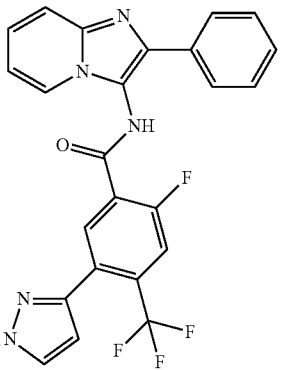 | 2-fluoro-5-(1-methyl-1H-pyrazol-3-yl)-N-(2-phenylimidazo[1,2-a]pyridin-3-yl)-4-(trifluoromethyl)benzamide | 480.2 |
| 36 | 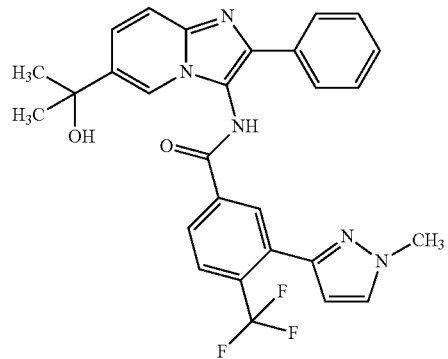 [SMILES: Cn1ccc(-c2cc(C(=O)Nc3c(-c4ccccc4)nc4ccc(C(C)(C)O)cn34)ccc2C(F)(F)F)n1] | N-[6-(1-hydroxy-1-methylethyl)-2-phenylimidazo[1,2-a]pyridin-3-yl]-3-(1-methyl-1H-pyrazol-3-yl)-4-(trifluoromethyl)benzamide | 520.2 |
| 37 | 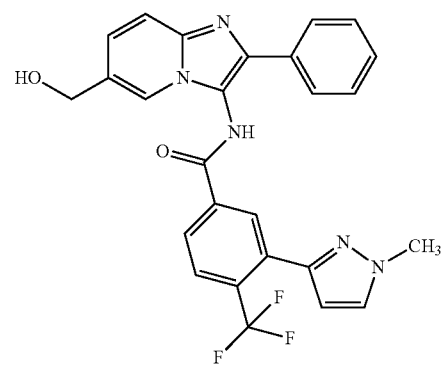 [SMILES: Cn1ccc(-c2cc(C(=O)Nc3c(-c4ccccc4)nc4ccc(CO)cn34)ccc2C(F)(F)F)n1] | N-[6-(hydroxymethyl)-2-phenylimidazo[1,2-a]pyridin-3-yl]-3-(1-methyl-1H-pyrazol-3-yl)-4-(trifluoromethyl)benzamide | 492.2 |
| 38 | 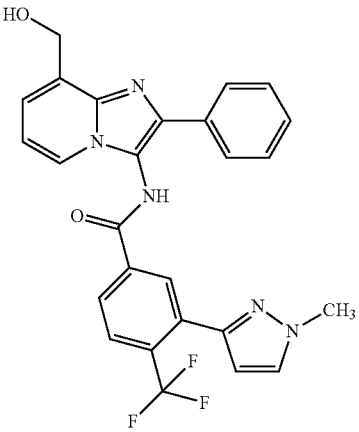 [SMILES: Cn1ccc(-c2cc(C(=O)Nc3c(-c4ccccc4)nc4c(CO)cccn34)ccc2C(F)(F)F)n1] | N-[8-(hydroxymethyl)-2-phenylimidazo[1,2-a]pyridin-3-yl]-3-(1-methyl-1H-pyrazol-3-yl)-4-(trifluoromethyl)benzamide | 492.2 |

TABLE 1-continued

| Compound Number | Structure | Compound Name | LCMS (M + 1) |
|---|---|---|---|
| 39 | 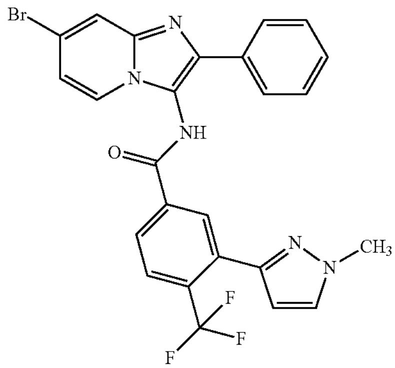 [SMILES: Cn1ccc(-c2cc(C(=O)Nc3c(-c4ccccc4)nc4cc(Br)ccn34)ccc2C(F)(F)F)n1] | N-(7-bromo-2-phenylimidazo[1,2-a]pyridin-3-yl)-3-(1-methyl-1H-pyrazol-3-yl)-4-(trifluoromethyl)benzamide | 541.8 |
| 40 | 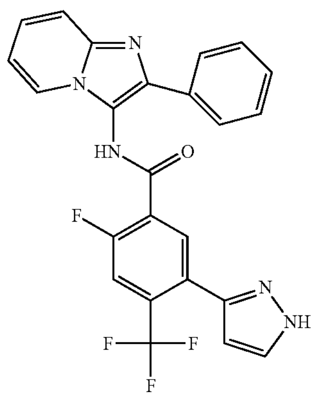 [SMILES: O=C(Nc1c(-c2ccccc2)nc2ccccn12)c1cc(-c2cc[nH]n2)c(C(F)(F)F)cc1F] | 2-fluoro-N-(2-phenylimidazo[1,2-a]pyridin-3-yl)-5-(1H-pyrazol-3-yl)-4-(trifluoromethyl)benzamide | 466.2 |
| 41 | 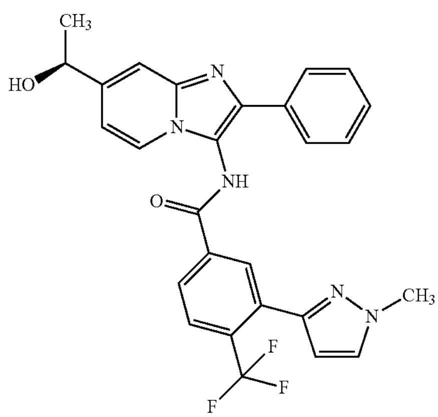 [SMILES: C[C@H](O)c1ccn2c(NC(=O)c3ccc(C(F)(F)F)c(-c4ccn(C)n4)c3)c(-c3ccccc3)nc2c1] | N-{7-[(1S)-1-hydroxyethyl]-2-phenylimidazo[1,2-a]pyridin-3-yl}-3-(1-methyl-1H-pyrazol-3-yl)-4-(trifluoromethyl)benzamide | 506.2 |
| 42 | 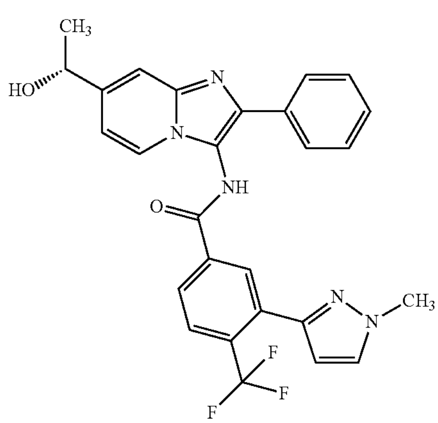 [SMILES: C[C@@H](O)c1ccn2c(NC(=O)c3ccc(C(F)(F)F)c(-c4ccn(C)n4)c3)c(-c3ccccc3)nc2c1] | N-{7-[(1R)-1-hydroxyethyl]-2-phenylimidazo[1,2-a]pyridin-3-yl}-3-(1-methyl-1H-pyrazol-3-yl)-4-(trifluoromethyl)benzamide | 506.2 |

TABLE 1-continued
| Compound Number | Structure | Compound Name | LCMS (M + 1) |
|---|---|---|---|
| 43 | 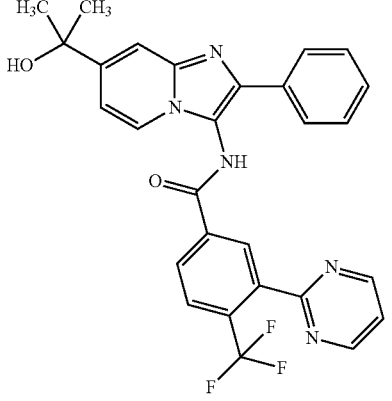 [SMILES: CC(C)(O)c1ccn2c(NC(=O)c3ccc(C(F)(F)F)c(-c4ncccn4)c3)c(-c3ccccc3)nc2c1] | N-[7-(1-hydroxy-1-methylethyl)-2-phenylimidazo[1,2-a]pyridin-3-yl]-3-pyrimidin-2-yl-4-(trifluoromethyl)benzamide | 518.2 |
| 44 | 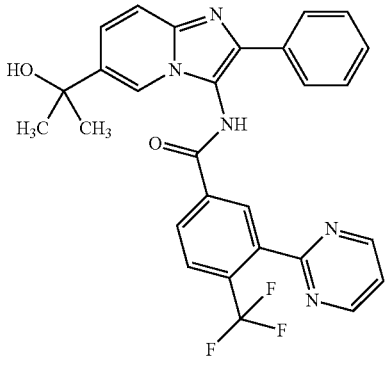 [SMILES: CC(C)(O)c1ccc2nc(-c3ccccc3)c(NC(=O)c3ccc(C(F)(F)F)c(-c4ncccn4)c3)n2c1] | N-[6-(1-hydroxy-1-methylethyl)-2-phenylimidazo[1,2-a]pyridin-3-yl]-3-pyrimidin-2-yl-4-(trifluoromethyl)benzamide | 518.2 |
| 45 | 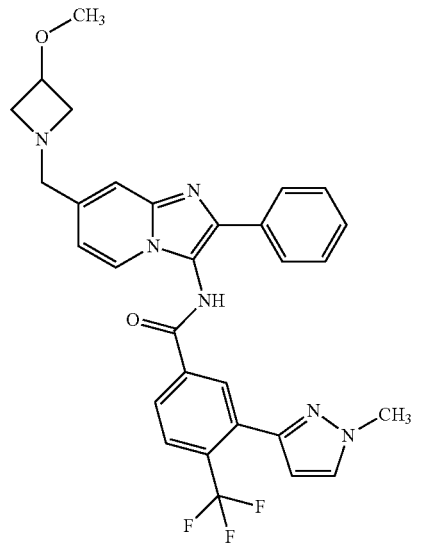 [SMILES: COC1CN(Cc2ccn3c(NC(=O)c4ccc(C(F)(F)F)c(-c5ccn(C)n5)c4)c(-c4ccccc4)nc3c2)C1] | N-{7-[(3-methoxyazetidin-1-yl)methyl]-2-phenylimidazo[1,2-a]pyridin-3-yl}-3-(1-methyl-1H-pyrazol-3-yl)-4-(trifluoromethyl)benzamide | 561.1 |

TABLE 1-continued

| Compound Number | Structure | Compound Name | LCMS (M + 1) |
|---|---|---|---|
| 46 | 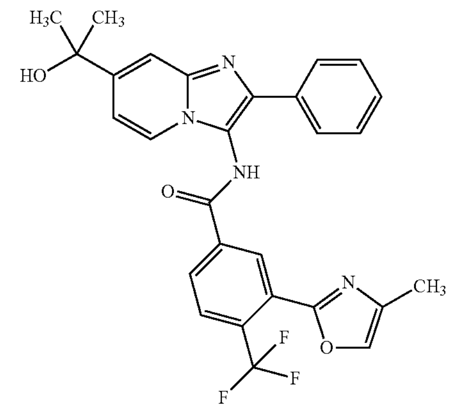 [SMILES: Cc1coc(-c2cc(C(=O)Nc3c(-c4ccccc4)nc4cc(C(C)(C)O)ccn34)ccc2C(F)(F)F)n1] | N-[7-(1-hydroxy-1-methylethyl)-2-phenylimidazo[1,2-a]pyridin-3-yl]-3-(4-methyl-1,3-oxazol-2-yl)-4-(trifluoromethyl)benzamide | 521.2 |
| 47 | 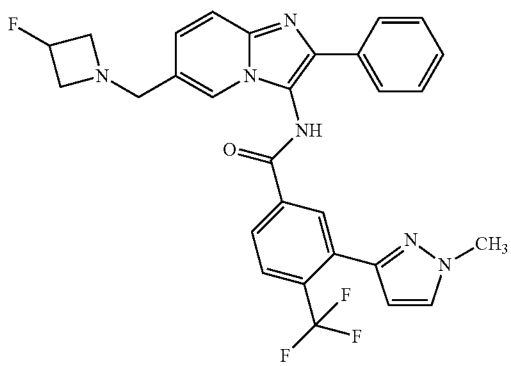 [SMILES: Cn1ccc(-c2cc(C(=O)Nc3c(-c4ccccc4)nc4ccc(CN5CC(F)C5)cn34)ccc2C(F)(F)F)n1] | N-{6-[(3-fluoroazetidin-1-yl)methyl]-2-phenylimidazo[1,2-a]pyridin-3-yl}-3-(1-methyl-1H-pyrazol-3-yl)-4-(trifluoromethyl)benzamide | 549.1 |
| 48 | 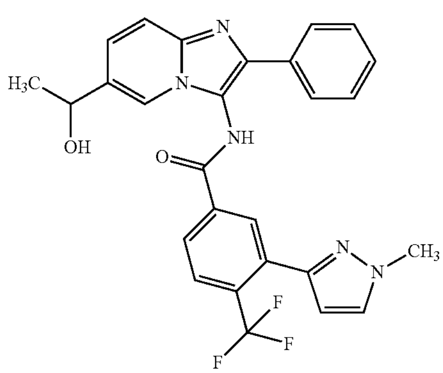 [SMILES: CC(O)c1ccc2nc(-c3ccccc3)c(NC(=O)c3ccc(C(F)(F)F)c(-c4ccn(C)n4)c3)n2c1] | (R or S)-N-[6-(1-hydroxyethyl)-2-phenylimidazo[1,2-a]pyridin-3-yl]-3-(1-methyl-1H-pyrazol-3-yl)-4-(trifluoromethyl)benzamide | 506.0 |
| 49 | 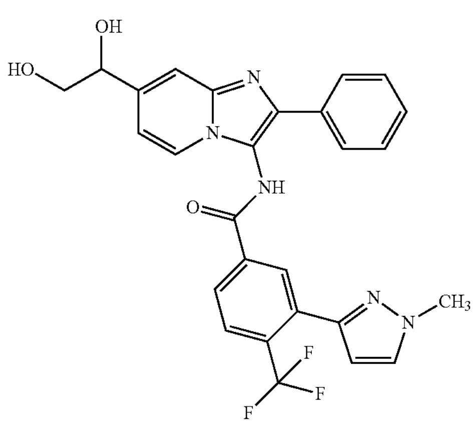 [SMILES: Cn1ccc(-c2cc(C(=O)Nc3c(-c4ccccc4)nc4cc(C(O)CO)ccn34)ccc2C(F)(F)F)n1] | (R or S)-N-[7-(1,2-dihydroxyethyl)-2-phenylimidazo[1,2-a]pyridin-3-yl]-3-(1-methyl-1H-pyrazol-3-yl)-4-(trifluoromethyl)benzamide | 522.0 |

TABLE 1-continued

| Compound Number | Structure | Compound Name | LCMS (M + 1) |
|---|---|---|---|
| 50 | 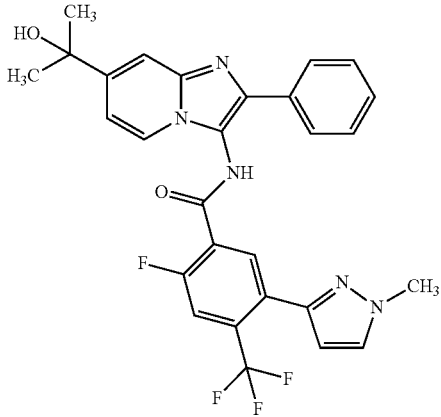 [SMILES: Cn1ccc(-c2cc(C(=O)Nc3c(-c4ccccc4)nc4cc(C(C)(C)O)ccn34)c(F)cc2C(F)(F)F)n1] | 2-fluoro-N-[7-(1-hydroxy-1-methylethyl)-2-phenylimidazo[1,2-a]pyridin-3-yl]-5-(1-methyl-1H-pyrazol-3-yl)-4-(trifluoromethyl)benzamide | 538.1 |
| 51 | 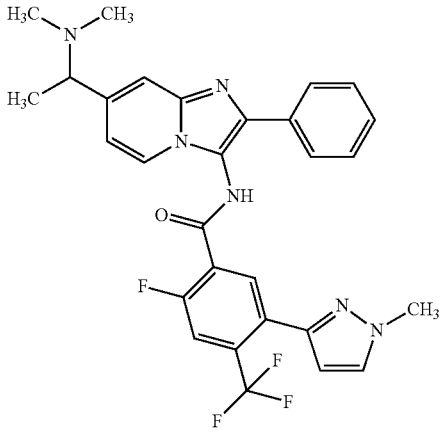 [SMILES: CC(c1ccn2c(NC(=O)c3cc(-c4ccn(C)n4)c(C(F)(F)F)cc3F)c(-c3ccccc3)nc2c1)N(C)C] | (R or S)-N-{7-[1-(dimethylamino)ethyl]-2-phenylimidazo[1,2-a]pyridin-3-yl}-2-fluoro-5-(1-methyl-1H-pyrazol-3-yl)-4-(trifluoromethyl)benzamide | 551.2 |
| 52 | 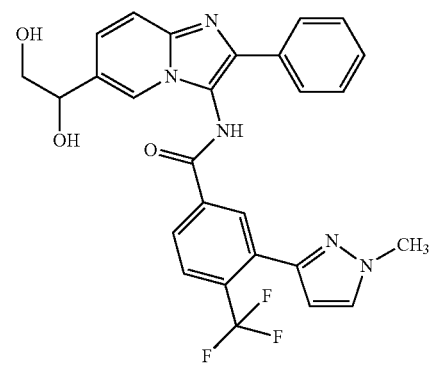 [SMILES: Cn1ccc(-c2cc(C(=O)Nc3c(-c4ccccc4)nc4ccc(C(O)CO)cn34)ccc2C(F)(F)F)n1] | (R or S)-N-[6-(1,2-dihydroxyethyl)-2-phenylimidazo[1,2-a]pyridin-3-yl]-3-(1-methyl-1H-pyrazol-3-yl)-4-(trifluoromethyl)benzamide | 522.2 |

TABLE 1-continued

| Compound Number | Structure | Compound Name | LCMS (M + 1) |
|---|---|---|---|
| 53 | 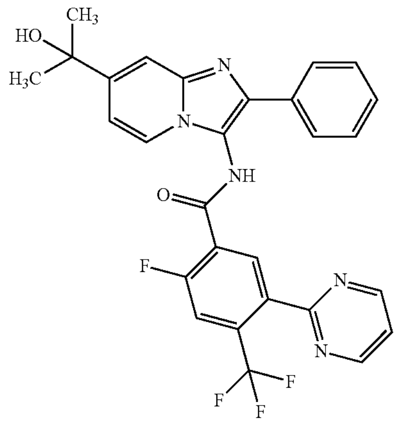 [SMILES: CC(C)(O)c1ccn2c(NC(=O)c3cc(-c4ncccn4)c(C(F)(F)F)cc3F)c(-c3ccccc3)nc2c1] | 2-fluoro-N-[7-(1-hydroxy-1-methylethyl)-2-phenylimidazo[1,2-a]pyridin-3-yl]-5-pyrimidin-2-yl-4-(trifluoromethyl)benzamide | 536.2 |
| 54 | 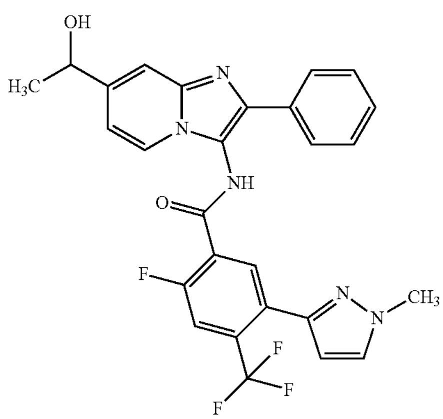 [SMILES: CC(O)c1ccn2c(NC(=O)c3cc(-c4ccn(C)n4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-(1-methyl-1H-pyrazol-3-yl)-4-(trifluoromethyl)benzamide | 524.2 |
| 55 | 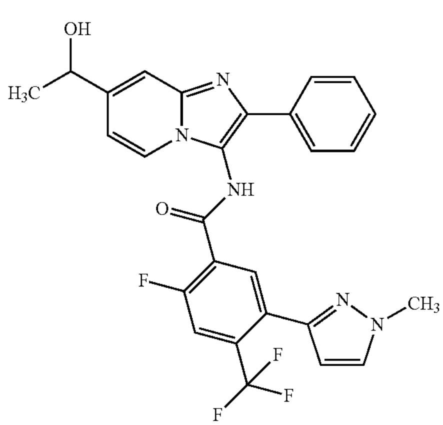 [SMILES: CC(O)c1ccn2c(NC(=O)c3cc(-c4ccn(C)n4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-(1-methyl-1H-pyrazol-3-yl)-4-(trifluoromethyl)benzamide | 524.2 |

TABLE 1-continued

| Compound Number | Structure | Compound Name | LCMS (M + 1) |
|---|---|---|---|
| 56 | 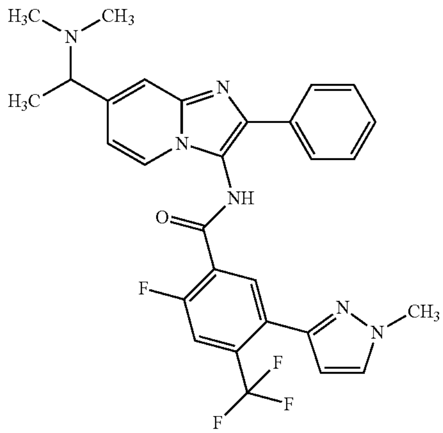 [SMILES: CC(c1ccn2c(NC(=O)c3cc(-c4ccn(C)n4)c(C(F)(F)F)cc3F)c(-c3ccccc3)nc2c1)N(C)C] | (R or S)-N-{7-[1-(dimethylamino)ethyl]-2-phenylimidazo[1,2-a]pyridin-3-yl}-3-(1-methyl-1H-pyrazol-3-yl)-4-(trifluoromethyl)benzamide | 533.2 |
| 57 | 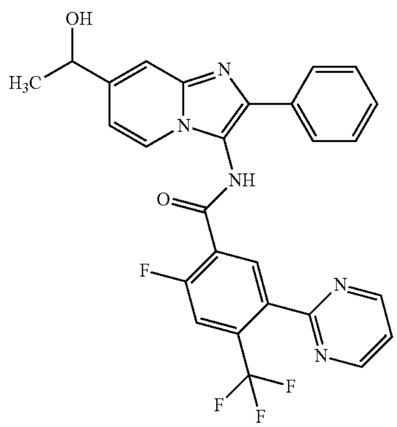 [SMILES: CC(O)c1ccn2c(NC(=O)c3cc(-c4ncccn4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-pyrimidin-2-yl-4-(trifluoromethyl)benzamide | 522.2 |
| 58 | 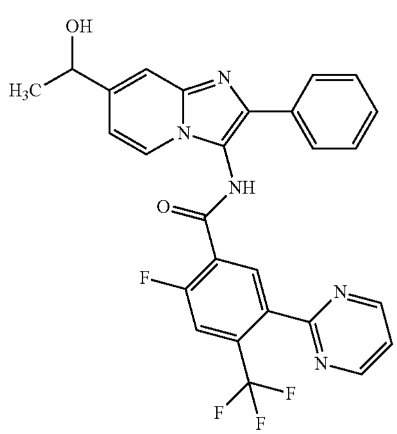 [SMILES: CC(O)c1ccn2c(NC(=O)c3cc(-c4ncccn4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-pyrimidin-2-yl-4-(trifluoromethyl)benzamide | 522.2 |

TABLE 1-continued

| Compound Number | Structure | Compound Name | LCMS (M + 1) |
|---|---|---|---|
| 59 | 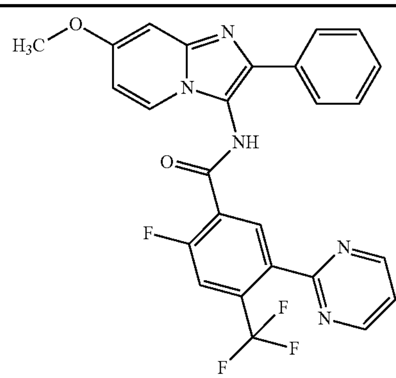 | 2-fluoro-N-(7-methoxy-2-phenylimidazo[1,2-a]pyridin-3-yl)-5-pyrimidin-2-yl-4-(trifluoromethyl)benzamide | 508.1 |
| 60 | 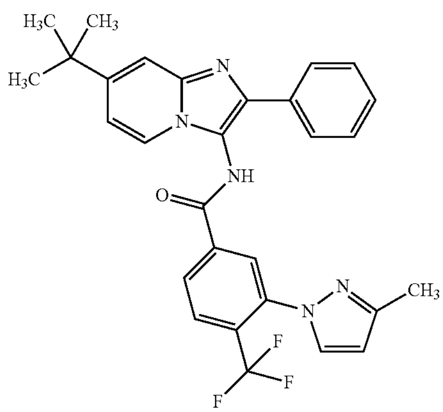 [SMILES: Cc1ccn(-c2cc(C(=O)Nc3c(-c4ccccc4)nc4cc(C(C)(C)C)ccn34)ccc2C(F)(F)F)n1] | N-[7-(1-hydroxy-1-methylethyl)-2-phenylimidazo[1,2-a]pyridin-3-yl]-3-(3-methyl-1H-pyrazol-1-yl)-4-(trifluoromethyl)benzamide | 520.4 |
| 61 | 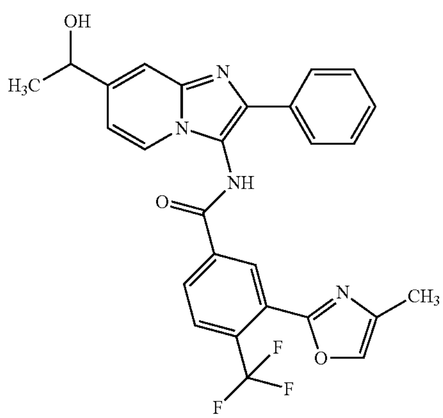 [SMILES: Cc1coc(-c2cc(C(=O)Nc3c(-c4ccccc4)nc4cc(C(C)O)ccn34)ccc2C(F)(F)F)n1] | (R or S)-N-[7-(1-hydroxyethyl)-2-phenylimidazo[1,2-a]pyridin-3-yl]-3-(4-methyl-1,3-oxazol-2-yl)-4-(trifluoromethyl)benzamide | 507.4 |
| 62 | 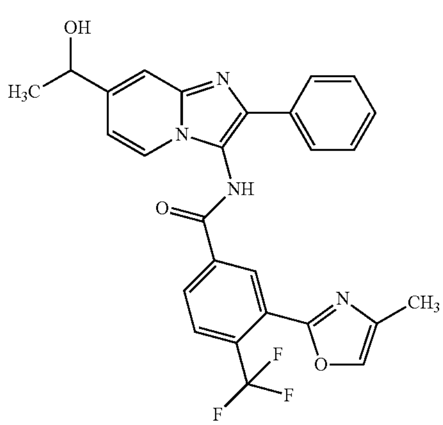 [SMILES: Cc1coc(-c2cc(C(=O)Nc3c(-c4ccccc4)nc4cc(C(C)O)ccn34)ccc2C(F)(F)F)n1] | (R or S)-N-[7-(1-hydroxyethyl)-2-phenylimidazo[1,2-a]pyridin-3-yl]-3-(4-methyl-1,3-oxazol-2-yl)-4-(trifluoromethyl)benzamide | 507.4 |

TABLE 1-continued

| Compound Number | Structure | Compound Name | LCMS (M + 1) |
|---|---|---|---|
| 63 | 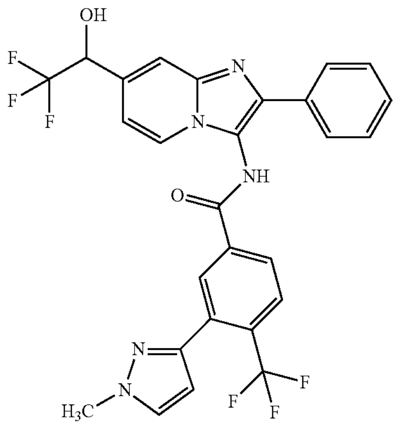 [SMILES: Cn1ccc(-c2cc(C(=O)Nc3c(-c4ccccc4)nc4cc(C(O)C(F)(F)F)ccn34)ccc2C(F)(F)F)n1] | (R or S)-3-(1-methyl-1H-pyrazol-3-yl)-N-[2-phenyl-7-(2,2,2-trifluoro-1-hydroxyethyl)imidazo[1,2-a]pyridin-3-yl]-4-(trifluoromethyl)benzamide | 560.3 |
| 64 | 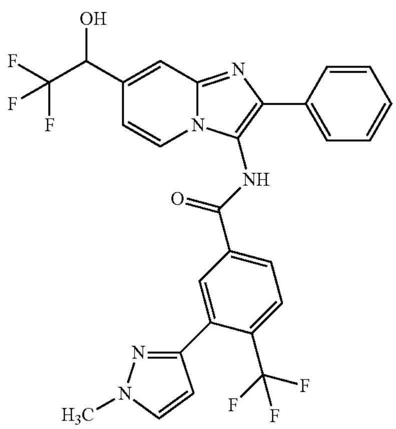 [SMILES: Cn1ccc(-c2cc(C(=O)Nc3c(-c4ccccc4)nc4cc(C(O)C(F)(F)F)ccn34)ccc2C(F)(F)F)n1] | (R or S)-3-(1-methyl-1H-pyrazol-3-yl)-N-[2-phenyl-7-(2,2,2-trifluoro-1-hydroxyethyl)imidazo[1,2-a]pyridin-3-yl]-4-(trifluoromethyl)benzamide | 560.3 |
| 65 | 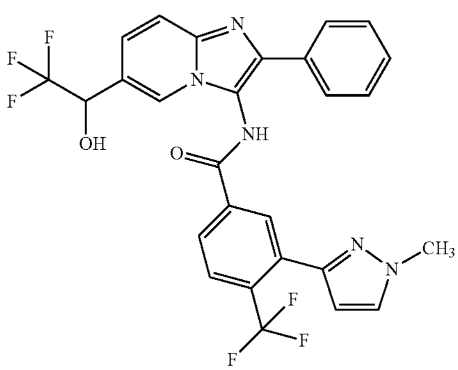 [SMILES: Cn1ccc(-c2cc(C(=O)Nc3c(-c4ccccc4)nc4ccc(C(O)C(F)(F)F)cn34)ccc2C(F)(F)F)n1] | (R or S)-3-(1-methyl-1H-pyrazol-3-yl)-N-[2-phenyl-6-(2,2,2-trifluoro-1-hydroxyethyl)imidazo[1,2-a]pyridin-3-yl]-4-(trifluoromethyl)benzamide | 560.3 |
| 66 | 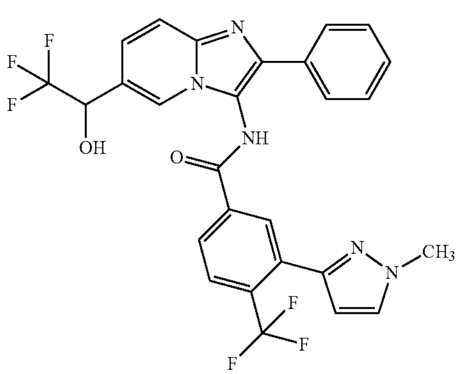 [SMILES: Cn1ccc(-c2cc(C(=O)Nc3c(-c4ccccc4)nc4ccc(C(O)C(F)(F)F)cn34)ccc2C(F)(F)F)n1] | (R or S)-3-(1-methyl-1H-pyrazol-3-yl)-N-[2-phenyl-6-(2,2,2-trifluoro-1-hydroxyethyl)imidazo[1,2-a]pyridin-3-yl]-4-(trifluoromethyl)benzamide | 560.3 |

TABLE 1-continued

| Compound Number | Structure | Compound Name | LCMS (M + 1) |
|---|---|---|---|
| 67 | 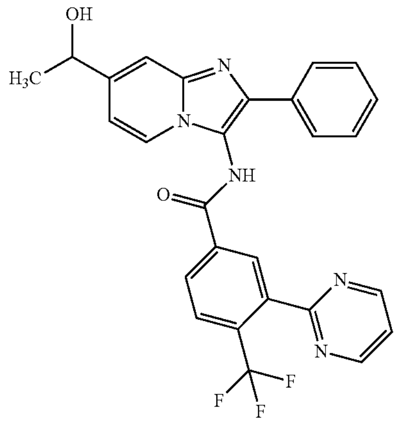 [SMILES: CC(O)c1ccn2c(NC(=O)c3ccc(C(F)(F)F)c(-c4ncccn4)c3)c(-c3ccccc3)nc2c1] | (R or S)-N-[7-(1-hydroxyethyl)-2-phenylimidazo[1,2-a]pyridin-3-yl]-3-pyrimidin-2-yl-4-(trifluoromethyl)benzamide | 504.4 |
| 68 | 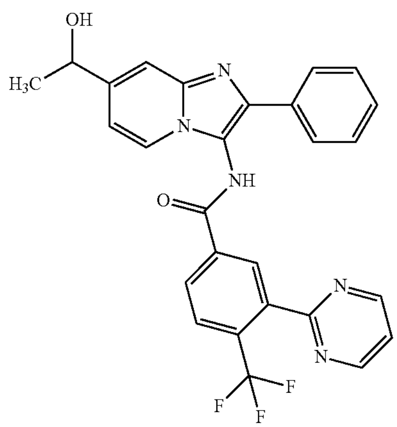 [SMILES: CC(O)c1ccn2c(NC(=O)c3ccc(C(F)(F)F)c(-c4ncccn4)c3)c(-c3ccccc3)nc2c1] | (R or S)-N-[7-(1-hydroxyethyl)-2-phenylimidazo[1,2-a]pyridin-3-yl]-3-pyrimidin-2-yl-4-(trifluoromethyl)benzamide | 504.4 |
| 69 | 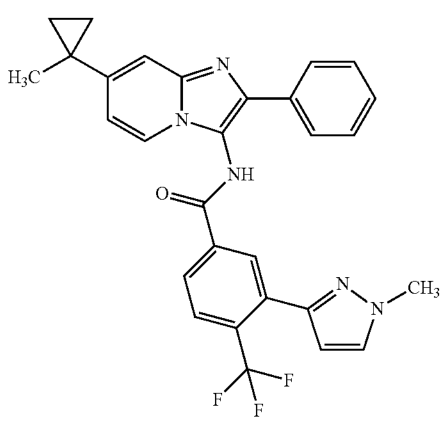 | N-[7-(1-hydroxycyclopropyl)-2-phenylimidazo[1,2-a]pyridin-3-yl]-3-(1-methyl-1H-pyrazol-3-yl)-4-(trifluoromethyl)benzamide | 518.2 |

TABLE 1-continued

| Compound Number | Structure | Compound Name | LCMS (M + 1) |
|---|---|---|---|
| 70 | 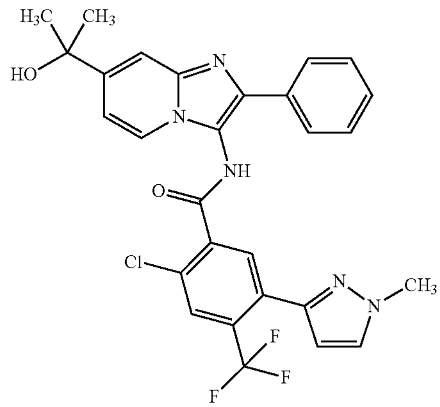 [SMILES: Cn1ccc(-c2cc(C(=O)Nc3c(-c4ccccc4)nc4cc(C(C)(C)O)ccn34)c(Cl)cc2C(F)(F)F)n1] | 2-chloro-N-[7-(1-hydroxy-1-methylethyl)-2-phenylimidazo[1,2-a]pyridin-3-yl]-5-(1-methyl-1H-pyrazol-3-yl)-4-(trifluoromethyl)benzamide | 554.3 |
| 71 | 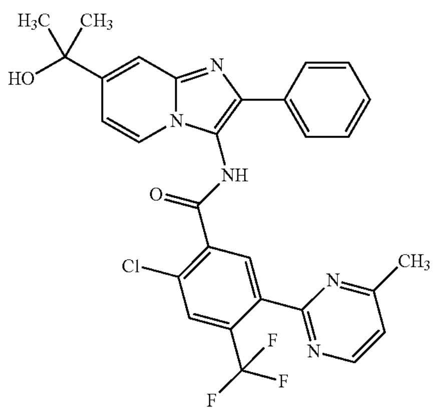 [SMILES: Cc1ccnc(-c2cc(C(=O)Nc3c(-c4ccccc4)nc4cc(C(C)(C)O)ccn34)c(Cl)cc2C(F)(F)F)n1] | 2-chloro-N-[7-(1-hydroxy-1-methylethyl)-2-phenylimidazo[1,2-a]pyridin-3-yl]-5-(4-methylpyrimidin-2-yl)-4-(trifluoromethyl)benzamide | 566.1 |
| 72 | 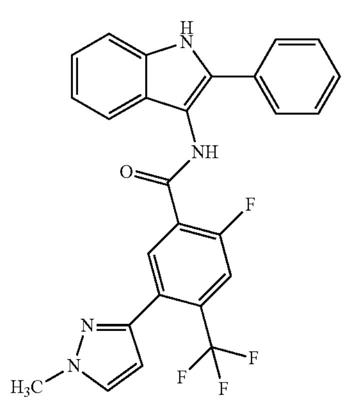 [SMILES: Cn1ccc(-c2cc(C(=O)Nc3c(-c4ccccc4)[nH]c4ccccc34)c(F)cc2C(F)(F)F)n1] | 2-fluoro-5-(1-methyl-1H-pyrazol-3-yl)-N-(2-phenyl-1H-indol-3-yl)-4-(trifluoromethyl)benzamide | 479.9 |

TABLE 1-continued

| Compound Number | Structure | Compound Name | LCMS (M + 1) |
|---|---|---|---|
| 73 | 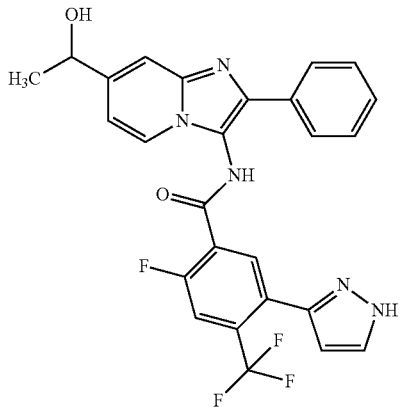 [SMILES: CC(O)c1ccn2c(NC(=O)c3cc(-c4cc[nH]n4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-(1H-pyrazol-3-yl)-4-(trifluoromethyl)benzamide | 510.2 |
| 74 | 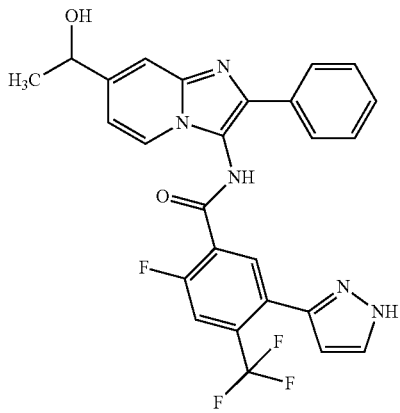 [SMILES: CC(O)c1ccn2c(NC(=O)c3cc(-c4cc[nH]n4)c(C(F)(F)F)cc3F)c(-c3ccccc3)nc2c1] | (R or S)-2-fluoro-N-[7-(1-hydroxyethyl)-2-phenylimidazo[1,2-a]pyridin-3-yl]-5-(1H-pyrazol-3-yl)-4-(trifluoromethyl)benzamide | 510.2 |
| 75 | 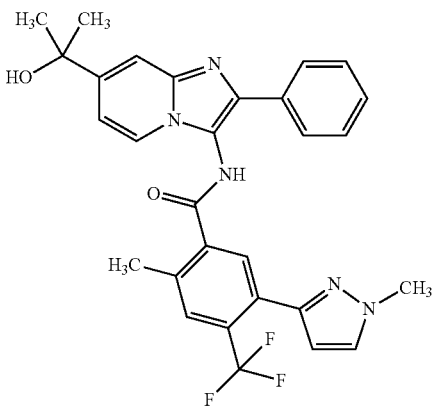 [SMILES: Cc1cc(C(F)(F)F)c(-c2ccn(C)n2)cc1C(=O)Nc1c(-c2ccccc2)nc2cc(C(C)(C)O)ccn12] | N-[7-(1-hydroxy-1-methylethyl)-2-phenylimidazo[1,2-a]pyridin-3-yl]-2-methyl-5-(1-methyl-1H-pyrazol-3-yl)-4-(trifluoromethyl)benzamide | 534.3 |

TABLE 1-continued

| Compound Number | Structure | Compound Name | LCMS (M + 1) |
|---|---|---|---|
| 76 | 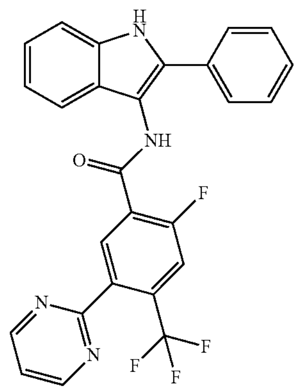 [SMILES: O=C(Nc1c(-c2ccccc2)[nH]c2ccccc12)c1cc(-c2ncccn2)c(C(F)(F)F)cc1F] | 2-fluoro-N-(2-phenyl-1H-indol-3-yl)-5-pyrimidin-2-yl-4-(trifluoromethyl)benzamide | 476.9 |
| 77 | 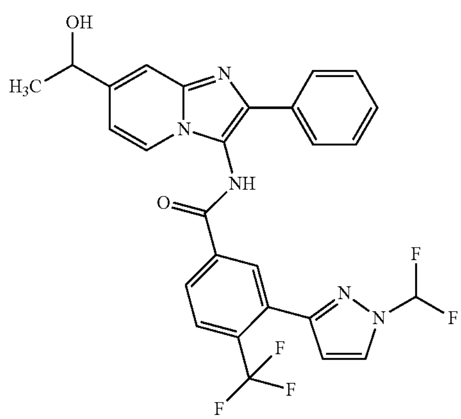 [SMILES: CC(O)c1ccn2c(NC(=O)c3ccc(C(F)(F)F)c(-c4ccn(C(F)F)n4)c3)c(-c3ccccc3)nc2c1] | (R or S)-3-[1-(difluoromethyl)-1H-pyrazol-3-yl]-N-[7-(1-hydroxyethyl)-2-phenylimidazo[1,2-a]pyridin-3-yl]-4-(trifluoromethyl)benzamide | 542.2 |
| 78 | 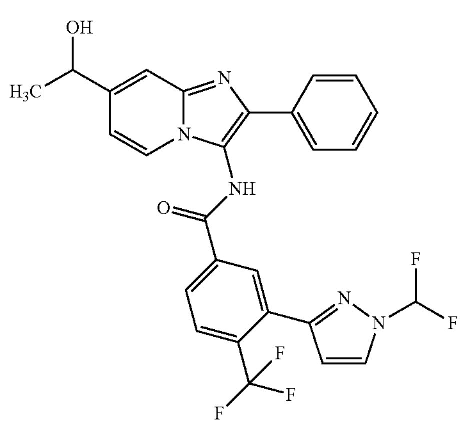 [SMILES: CC(O)c1ccn2c(NC(=O)c3ccc(C(F)(F)F)c(-c4ccn(C(F)F)n4)c3)c(-c3ccccc3)nc2c1] | (R or S)-3-[1-(difluoromethyl)-1H-pyrazol-3-yl]-N-[7-(1-hydroxyethyl)-2-phenylimidazo[1,2-a]pyridin-3-yl]-4-(trifluoromethyl)benzamide | 542.3 |

TABLE 1-continued

| Compound Number | Structure | Compound Name | LCMS (M + 1) |
|---|---|---|---|
| 79 | 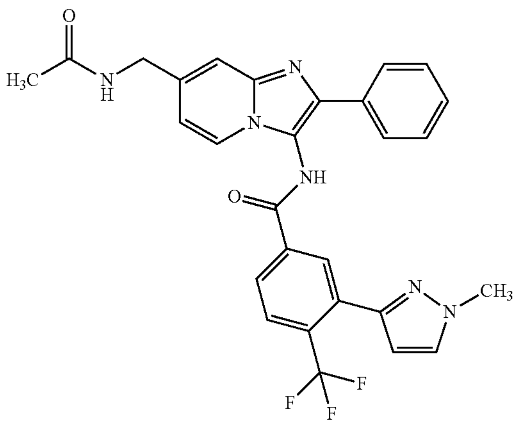 [SMILES: CC(=O)NCc1ccn2c(NC(=O)c3ccc(C(F)(F)F)c(-c4ccn(C)n4)c3)c(-c3ccccc3)nc2c1] | N-{7-[(acetylamino)methyl]-2-phenylimidazo[1,2-a]pyridin-3-yl}-3-(1-methyl-1H-pyrazol-3-yl)-4-(trifluoromethyl)benzamide | 533.2 |
| 80 | 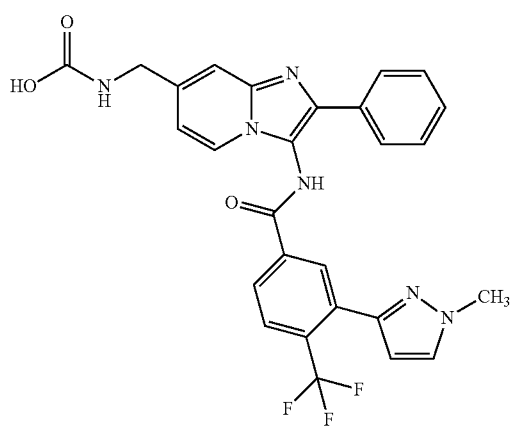 [SMILES: Cn1ccc(-c2cc(C(=O)Nc3c(-c4ccccc4)nc4cc(CNC(=O)O)ccn34)ccc2C(F)(F)F)n1] | N-(7-{[(hydroxyacetyl)amino]methyl}-2-phenylimidazo[1,2-a]pyridin-3-yl)-3-(1-methyl-1H-pyrazol-3-yl)-4-(trifluoromethyl)benzamide | 549.3 |
| 81 | 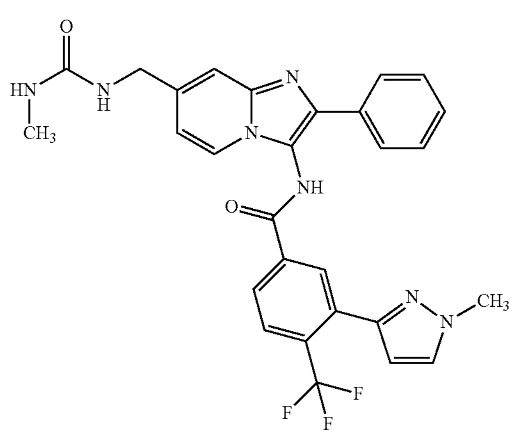 [SMILES: CNC(=O)NCc1ccn2c(NC(=O)c3ccc(C(F)(F)F)c(-c4ccn(C)n4)c3)c(-c3ccccc3)nc2c1] | N-(7-{[(methylcarbamoyl)amino]methyl}-2-phenylimidazo[1,2-a]pyridin-3-yl)-3-(1-methyl-1H-pyrazol-3-yl)-4-(trifluoromethyl)benzamide | 548.4 |

TABLE 1-continued

| Compound Number | Structure | Compound Name | LCMS (M + 1) |
|---|---|---|---|
| 82 | 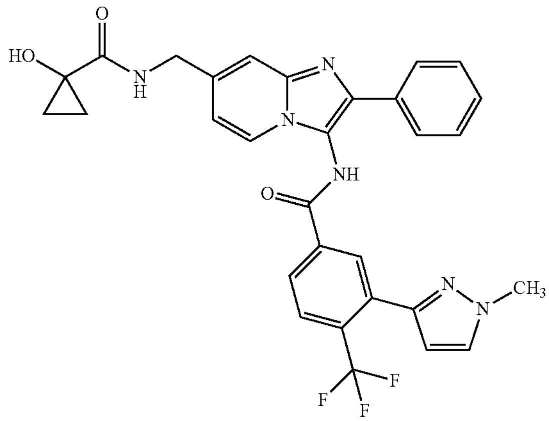 [SMILES: Cn1ccc(-c2cc(C(=O)Nc3c(-c4ccccc4)nc4cc(CNC(=O)C5(O)CC5)ccn34)ccc2C(F)(F)F)n1] | N-[7-({[(1-hydroxycyclopropyl)carbonyl]amino}methyl)-2-phenylimidazo[1,2-a]pyridin-3-yl]-3-(1-methyl-1H-pyrazol-3-yl)-4-(trifluoromethyl)benzamide | 575.3 |
| 83 | 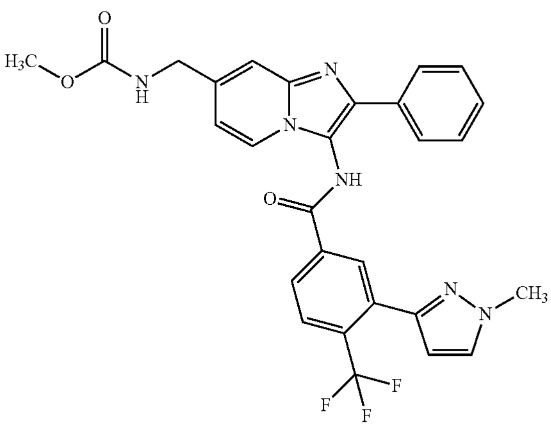 | methyl{[3-({[3-(1-methyl-1H-pyrazol-3-yl)-4-(trifluoromethyl)phenyl]carbonyl}amino)-2-phenylimidazo[1,2-a]pyridin-7-yl]methyl}carbamate | 549.2 |
| 84 | 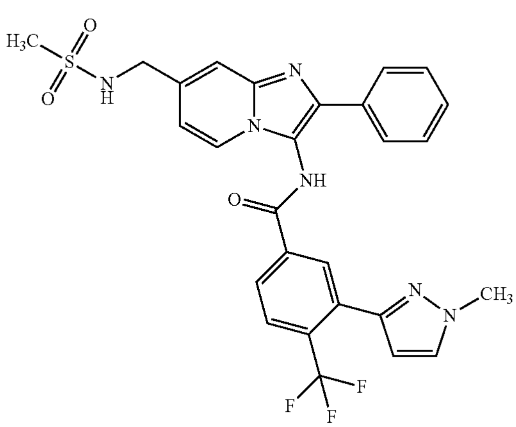 | 3-(1-methyl-1H-pyrazol-3-yl)-N-(7-{[(methylsulfonyl)amino]methyl}-2-phenylimidazo[1,2-a]pyridin-3-yl)-4-(trifluoromethyl)benzamide | 569.3 |

TABLE 1-continued

| Compound Number | Structure | Compound Name | LCMS (M + 1) |
|---|---|---|---|
| 85 | 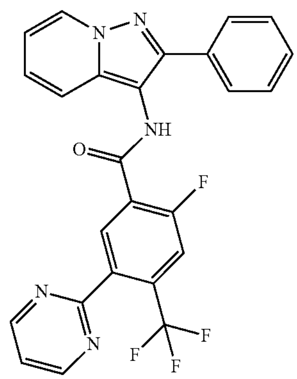 [SMILES: O=C(Nc1c(-c2ccccc2)nn2ccccc12)c1cc(-c2ncccn2)c(C(F)(F)F)cc1F] | 2-fluoro-N-(2-phenylpyrazolo[1,5-a]pyridin-3-yl)-5-pyrimidin-2-yl-4-(trifluoromethyl)benzamide | 477.9 |
| 86 | 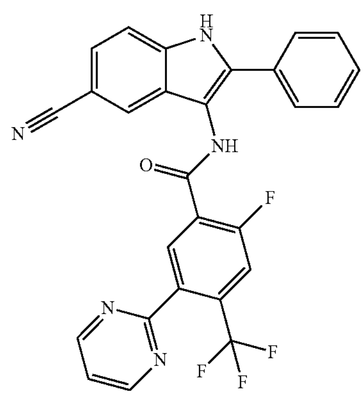 [SMILES: N#Cc1ccc2[nH]c(-c3ccccc3)c(NC(=O)c3cc(-c4ncccn4)c(C(F)(F)F)cc3F)c2c1] | N-(5-cyano-2-phenyl-1H-indol-3-yl)-2-fluoro-5-pyrimidin-2-yl-4-(trifluoromethyl)benzamide | 501.9 |
| 87 | 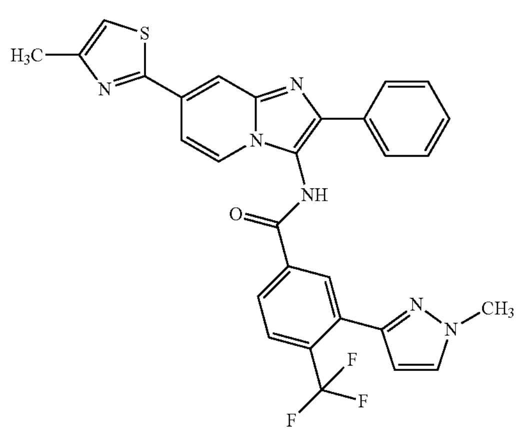 | 3-(1-methyl-1H-pyrazol-3-yl)-N-[7-(4-methyl-1,3-thiazol-2-yl)-2-phenylimidazo[1,2-a]pyridin-3-yl]-4-(trifluoromethyl)benzamide | 559.3 |

TABLE 1-continued

| Compound Number | Structure | Compound Name | LCMS (M + 1) |
|---|---|---|---|
| 88 | 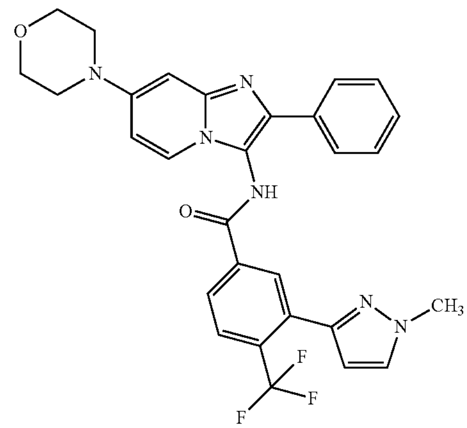 [SMILES: Cn1ccc(-c2cc(C(=O)Nc3c(-c4ccccc4)nc4cc(N5CCOCC5)ccn34)ccc2C(F)(F)F)n1] | 3-(1-methyl-1H-pyrazol-3-yl)-N-(7-morpholin-4-yl-2-phenylimidazo[1,2-a]pyridin-3-yl)-4-(trifluoromethyl)benzamide | 547.3 |
| 89 | 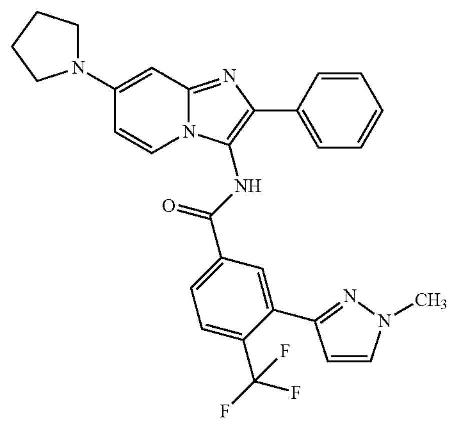 [SMILES: Cn1ccc(-c2cc(C(=O)Nc3c(-c4ccccc4)nc4cc(N5CCCC5)ccn34)ccc2C(F)(F)F)n1] | 3-(1-methyl-1H-pyrazol-3-yl)-N-(2-phenyl-7-pyrrolidin-1-ylimidazo[1,2-a]pyridin-3-yl)-4-(trifluoromethyl)benzamide | 531.3 |
| 90 | 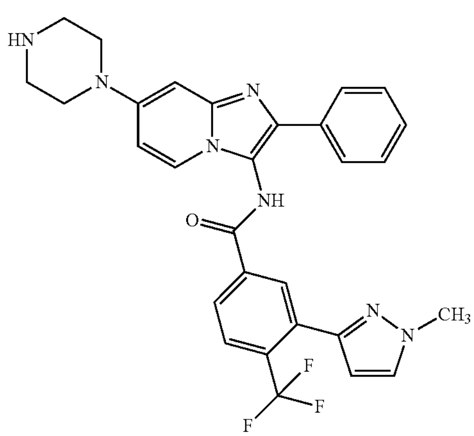 [SMILES: Cn1ccc(-c2cc(C(=O)Nc3c(-c4ccccc4)nc4cc(N5CCNCC5)ccn34)ccc2C(F)(F)F)n1] | 3-(1-methyl-1H-pyrazol-3-yl)-N-(2-phenyl-7-piperazin-1-ylimidazo[1,2-a]pyridin-3-yl)-4-(trifluoromethyl)benzamide | 546.3 |

TABLE 1-continued

| Compound Number | Structure | Compound Name | LCMS (M + 1) |
|---|---|---|---|
| 91 | 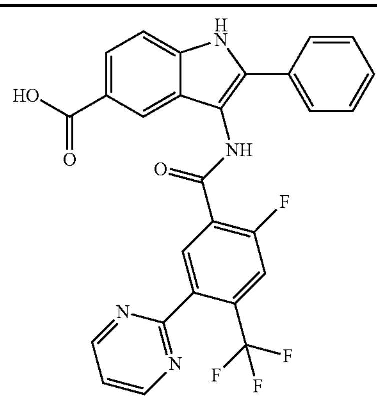 | 3-({[2-fluoro-5-pyrimidin-2-yl-4-(trifluoromethyl)phenyl]carbonyl}amino)-2-phenyl-1H-indole-5-carboxylic acid | 520.1 |
| 92 | 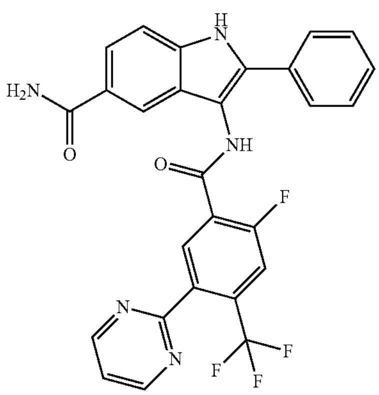 [SMILES: NC(=O)c1ccc2[nH]c(-c3ccccc3)c(NC(=O)c3cc(-c4ncccn4)c(C(F)(F)F)cc3F)c2c1] | 3-({[2-fluoro-5-pyrimidin-2-yl-4-(trifluoromethyl)phenyl]carbonyl}amino)-2-phenyl-1H-indole-5-carboxamide | 520.1 |
| 93 | 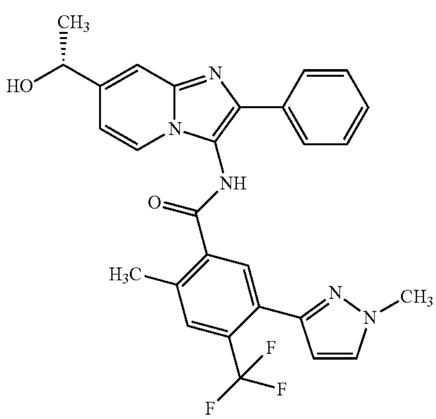 [SMILES: Cc1cc(C(F)(F)F)c(-c2ccn(C)n2)cc1C(=O)Nc1c(-c2ccccc2)nc2cc([C@@H](C)O)ccn12] | N-{7-[(1R)-1-hydroxyethyl]-2-phenylimidazo[1,2-a]pyridin-3-yl}-2-methyl-5-(1-methyl-1H-pyrazol-3-yl)-4-(trifluoromethyl)benzamide | 520.3 |
| 94 | 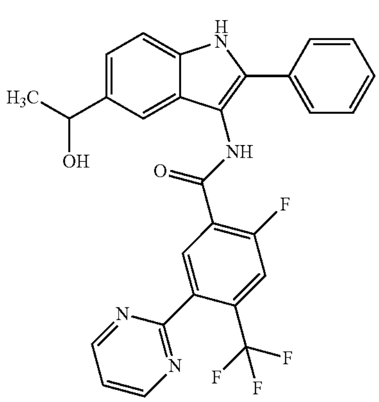 [SMILES: CC(O)c1ccc2[nH]c(-c3ccccc3)c(NC(=O)c3cc(-c4ncccn4)c(C(F)(F)F)cc3F)c2c1] | (R or S)-2-fluoro-N-[5-(1-hydroxyethyl)-2-phenyl-1H-indol-3-yl]-5-pyrimidin-2-yl-4-(trifluoromethyl)benzamide | 521.1 |

TABLE 1-continued

| Compound Number | Structure | Compound Name | LCMS (M + 1) |
|---|---|---|---|
| 95 | 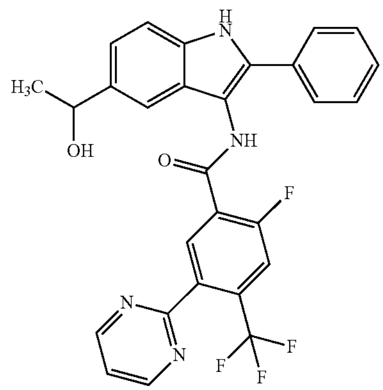 [SMILES: CC(O)c1ccc2[nH]c(-c3ccccc3)c(NC(=O)c3cc(-c4ncccn4)c(C(F)(F)F)cc3F)c2c1] | (R or S)-2-fluoro-N-[5-(1-hydroxyethyl)-2-phenyl-1H-indol-3-yl]-5-pyrimidin-2-yl-4-(trifluoromethyl)benzamide | 521.1 |
| 96 | 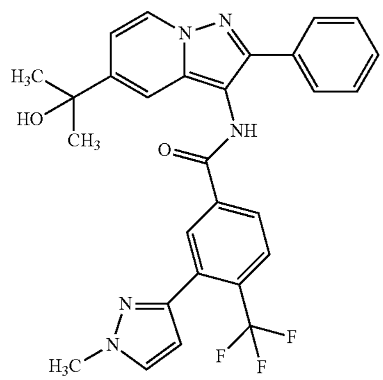 [SMILES: Cn1ccc(-c2cc(C(=O)Nc3c(-c4ccccc4)nn4ccc(C(C)(C)O)cc34)ccc2C(F)(F)F)n1] | N-[5-(1-hydroxy-1-methylethyl)-2-phenylpyrazolo[1,5-a]pyridin-3-yl]-3-(1-methyl-1H-pyrazol-3-yl)-4-(trifluoromethyl)benzamide | 520.1 |
| 97 | 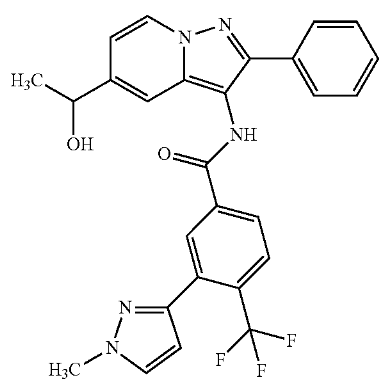 [SMILES: CC(O)c1ccn2nc(-c3ccccc3)c(NC(=O)c3ccc(C(F)(F)F)c(-c4ccn(C)n4)c3)c2c1] | (R or S)-N-[5-(1-hydroxyethyl)-2-phenylpyrazolo[1,5-a]pyridin-3-yl]-3-(1-methyl-1H-pyrazol-3-yl)-4-(trifluoromethyl)benzamide | 506.1 |
| 98 | 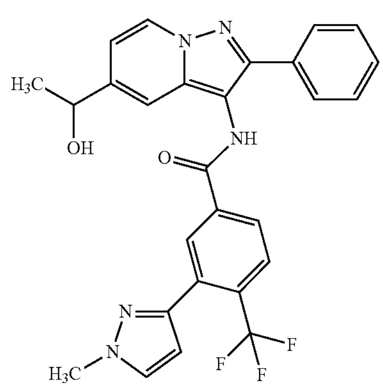 [SMILES: CC(O)c1ccn2nc(-c3ccccc3)c(NC(=O)c3ccc(C(F)(F)F)c(-c4ccn(C)n4)c3)c2c1] | (R or S)-N-[5-(1-hydroxyethyl)-2-phenylpyrazolo[1,5-a]pyridin-3-yl]-3-(1-methyl-1H-pyrazol-3-yl)-4-(trifluoromethyl)benzamide | 506.1 |

TABLE 1-continued
| Compound Number | Structure | Compound Name | LCMS (M + 1) |
|---|---|---|---|
| 99 | 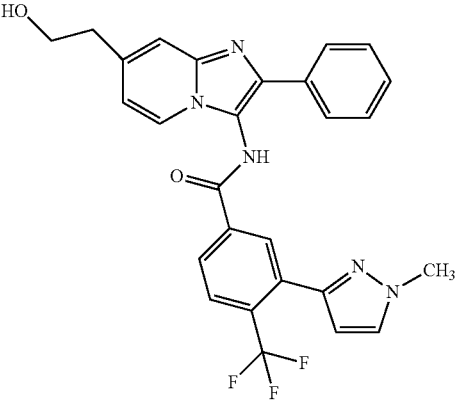 [SMILES: Cn1ccc(-c2cc(C(=O)Nc3c(-c4ccccc4)nc4cc(CCO)ccn34)ccc2C(F)(F)F)n1] | N-[7-(2-hydroxyethyl)-2-phenylimidazo[1,2-a]pyridin-3-yl]-3-(1-methyl-1H-pyrazol-3-yl)-4-(trifluoromethyl)benzamide | 506.2 |
| 100 | 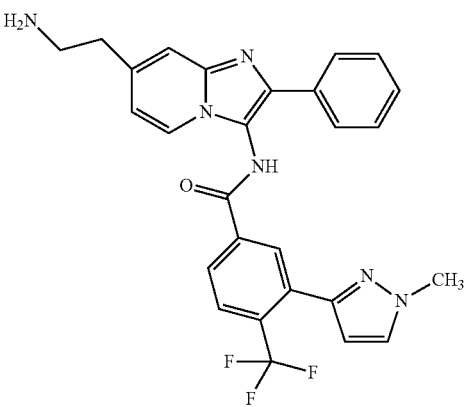 [SMILES: Cn1ccc(-c2cc(C(=O)Nc3c(-c4ccccc4)nc4cc(CCN)ccn34)ccc2C(F)(F)F)n1] | N-[7-(2-aminoethyl)-2-phenylimidazo[1,2-a]pyridin-3-yl]-3-(1-methyl-1H-pyrazol-3-yl)-4-(trifluoromethyl)benzamide | 505.2 |
| 101 | 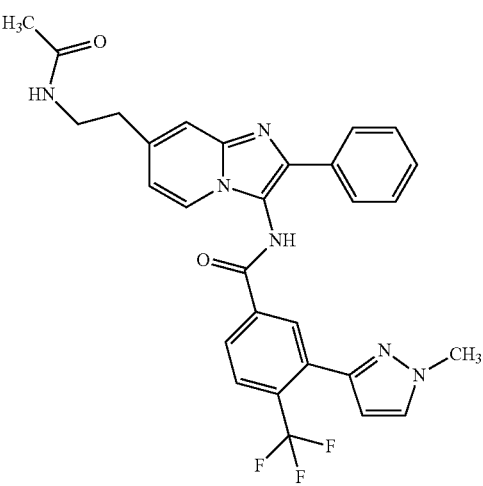 [SMILES: CC(=O)NCCc1ccn2c(NC(=O)c3ccc(C(F)(F)F)c(-c4ccn(C)n4)c3)c(-c3ccccc3)nc2c1] | N-{7-[2-(acetylamino)ethyl]-2-phenylimidazo[1,2-a]pyridin-3-yl}-3-(1-methyl-1H-pyrazol-3-yl)-4-(trifluoromethyl)benzamide | 547.2 |

TABLE 1-continued

| Compound Number | Structure | Compound Name | LCMS (M + 1) |
|---|---|---|---|
| 102 | 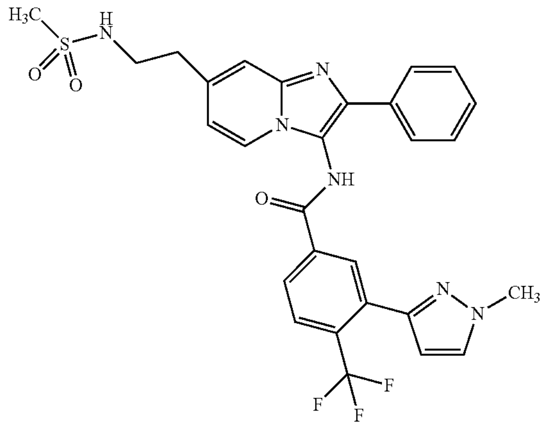 [SMILES: Cn1ccc(-c2cc(C(=O)Nc3c(-c4ccccc4)nc4cc(CCNS(C)(=O)=O)ccn34)ccc2C(F)(F)F)n1] | 3-(1-methyl-1H-pyrazol-3-yl)-N-(7-{2-[(methylsulfonyl)amino]ethyl}-2-phenylimidazo[1,2-a]pyridin-3-yl)-4-(trifluoromethyl)benzamide | 583.1 |
| 103 | 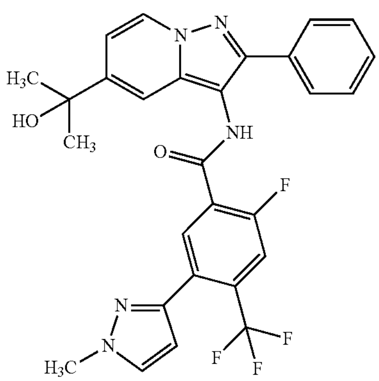 [SMILES: Cn1ccc(-c2cc(C(=O)Nc3c(-c4ccccc4)nn4ccc(C(C)(C)O)cc34)c(F)cc2C(F)(F)F)n1] | 2-fluoro-N-[5-(1-hydroxy-1-methylethyl)-2-phenylpyrazolo[1,5-a]pyridin-3-yl]-5-(1-methyl-1H-pyrazol-3-yl)-4-(trifluoromethyl)benzamide | 538.1 |
| 104 | 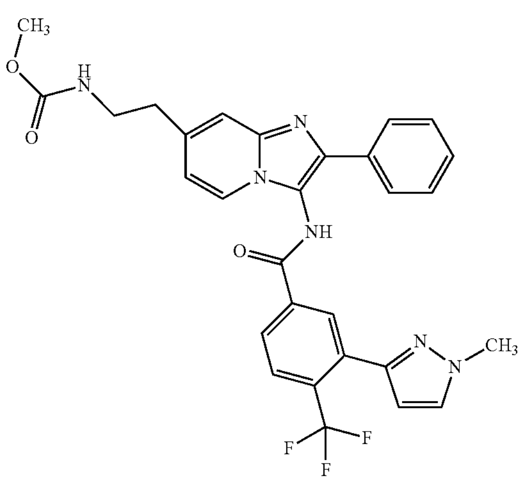 [SMILES: COC(=O)NCCc1ccn2c(NC(=O)c3ccc(C(F)(F)F)c(-c4ccn(C)n4)c3)c(-c3ccccc3)nc2c1] | methyl{2-[3-({[3-(1-methyl-1H-pyrazol-3-yl)-4-(trifluoromethyl)phenyl]carbonyl}amino)-2-phenylimidazo[1,2-a]pyridin-7-yl]ethyl}carbamate | 563.2 |

TABLE 1-continued

| Compound Number | Structure | Compound Name | LCMS (M + 1) |
|---|---|---|---|
| 105 | 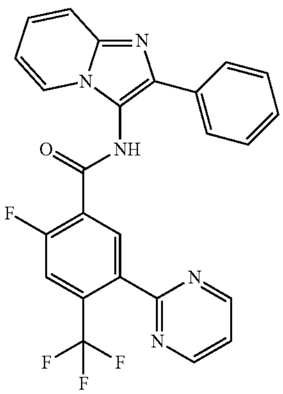 [SMILES: O=C(Nc1c(-c2ccccc2)nc2ccccn12)c1cc(-c2ncccn2)c(C(F)(F)F)cc1F] | 2-fluoro-N-(2-phenylimidazo[1,2-a]pyridin-3-yl)-5-pyrimidin-2-yl-4-(trifluoromethyl)benzamide | 478.3 |
| 106 | 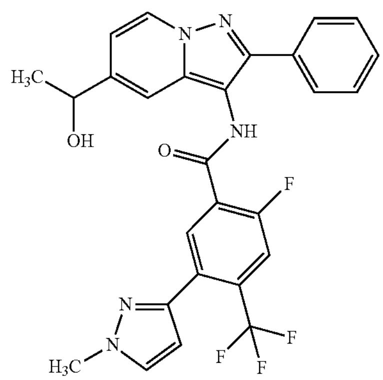 [SMILES: CC(O)c1ccn2nc(-c3ccccc3)c(NC(=O)c3cc(-c4ccn(C)n4)c(C(F)(F)F)cc3F)c2c1] | (R or S)-2-fluoro-N-[5-(1-hydroxyethyl)-2-phenylpyrazolo[1,5-a]pyridin-3-yl]-5-(1-methyl-1H-pyrazol-3-yl)-4-(trifluoromethyl)benzamide | 524.2 |
| 107 | 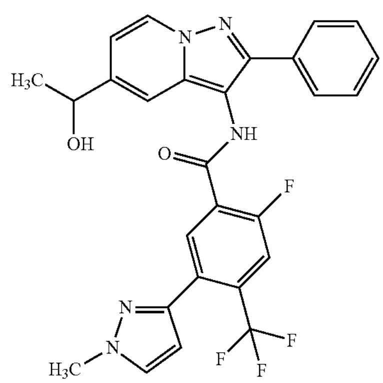 [SMILES: CC(O)c1ccn2nc(-c3ccccc3)c(NC(=O)c3cc(-c4ccn(C)n4)c(C(F)(F)F)cc3F)c2c1] | (R or S)-2-fluoro-N-[5-(1-hydroxyethyl)-2-phenylpyrazolo[1,5-a]pyridin-3-yl]-5-(1-methyl-1H-pyrazol-3-yl)-4-(trifluoromethyl)benzamide | 524.2 |
| 108 | 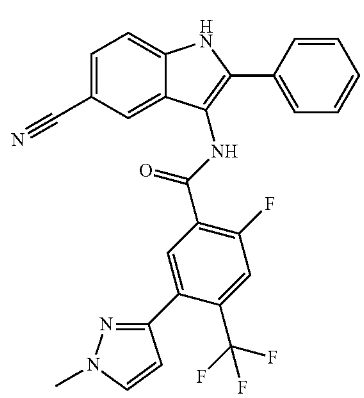 [SMILES: Cn1ccc(-c2cc(C(=O)Nc3c(-c4ccccc4)[nH]c4ccc(C#N)cc34)c(F)cc2C(F)(F)F)n1] | N-(5-cyano-2-phenyl-1H-indol-3-yl)-2-fluoro-5-(1-methyl-1H-pyrazol-3-yl)-4-(trifluoromethyl)benzamide | 504.1 |

TABLE 1-continued

| Compound Number | Structure | Compound Name | LCMS (M + 1) |
|---|---|---|---|
| 109 | 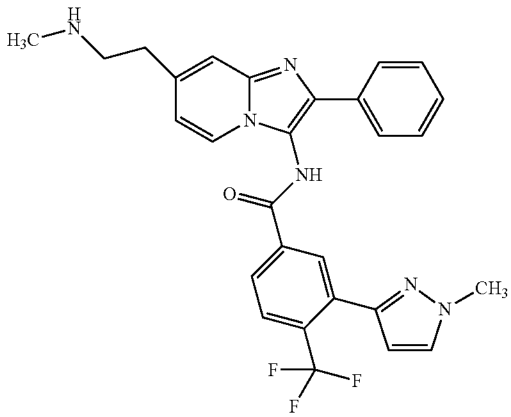 | N-{7-[2-(methylamino)ethyl]-2-phenylimidazo[1,2-a]pyridin-3-yl}-3-(1-methyl-1H-pyrazol-3-yl)-4-(trifluoromethyl)benzamide | 519.2 |
| 110 | 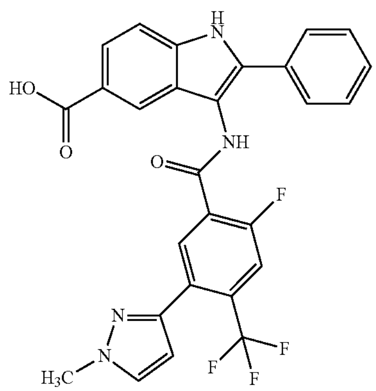 [SMILES: Cn1ccc(-c2cc(C(=O)Nc3c(-c4ccccc4)[nH]c4ccc(C(=O)O)cc34)c(F)cc2C(F)(F)F)n1] | 3-({[2-fluoro-5-(1-methyl-1H-pyrazol-3-yl)-4-(trifluoromethyl)phenyl]carbonyl}amino)-2-phenyl-1H-indole-5-carboxylic acid | 522.2 |
| 111 | 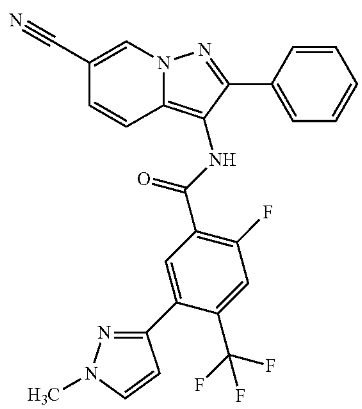 [SMILES: Cn1ccc(-c2cc(C(=O)Nc3c(-c4ccccc4)nn4cc(C#N)ccc34)c(F)cc2C(F)(F)F)n1] | N-(6-cyano-2-phenylpyrazolo[1,5-a]pyridin-3-yl)-2-fluoro-5-(1-methyl-1H-pyrazol-3-yl)-4-(trifluoromethyl)benzamide | 505.8 |
| 112 | 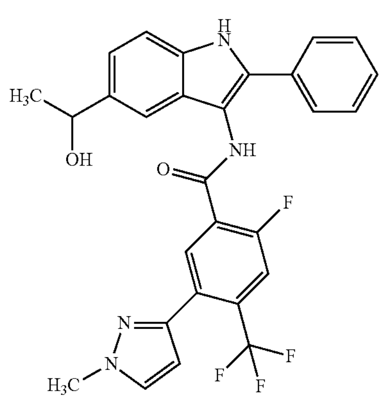 [SMILES: CC(O)c1ccc2[nH]c(-c3ccccc3)c(NC(=O)c3cc(-c4ccn(C)n4)c(C(F)(F)F)cc3F)c2c1] | (R or S)-2-fluoro-N-[5-(1-hydroxyethyl)-2-phenyl-1H-indol-3-yl]-5-(1-methyl-1H-pyrazol-3-yl)-4-(trifluoromethyl)benzamide | 521.1 |

TABLE 1-continued

| Compound Number | Structure | Compound Name | LCMS (M + 1) |
|---|---|---|---|
| 113 | 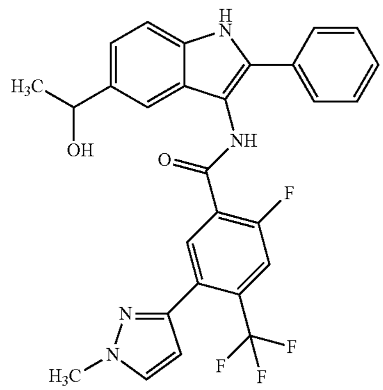 [SMILES: CC(O)c1ccc2[nH]c(-c3ccccc3)c(NC(=O)c3cc(-c4ccn(C)n4)c(C(F)(F)F)cc3F)c2c1] | (R or S)-2-fluoro-N-[5-(1-hydroxyethyl)-2-phenyl-1H-indol-3-yl]-5-(1-methyl-1H-pyrazol-3-yl)-4-(trifluoromethyl)benzamide | 521.1 |
| 114 | 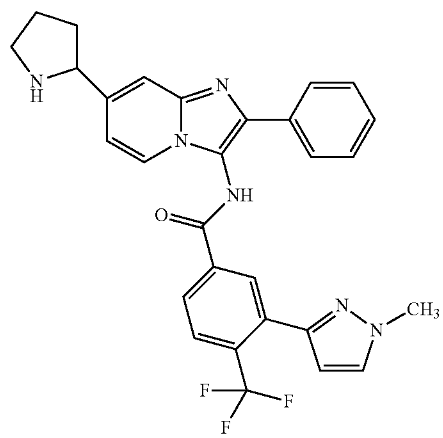 [SMILES: Cn1ccc(-c2cc(C(=O)Nc3c(-c4ccccc4)nc4cc(C5CCCN5)ccn34)ccc2C(F)(F)F)n1] | (R or S)-3-(1-methyl-1H-pyrazol-3-yl)-N-(2-phenyl-7-pyrrolidin-2-ylimidazo[1,2-a]pyridin-3-yl)-4-(trifluoromethyl)benzamide | 531.2 |
| 115 | | 2-fluoro-N-{7-[(1R)-1-hydroxyethyl]-2-phenylimidazo[1,2-a]pyridin-3-yl}-5-(1-methyl-1H-pyrazol-3-yl)-4-(1,1,2-trifluoroethyl)benzamide | 538.0 | or pharmaceutically acceptable salts thereof

The invention is also directed to methods of treating a patient (preferably a human) for diseases or disorders in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a therapeutically effective amount of a compound of the invention, or a pharmaceutically acceptable salt thereof.

The invention is also directed to the use of a compound of the invention for treating a disease or disorder in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a compound of the invention, or a pharmaceutically acceptable salt thereof.

The invention is also directed to medicaments or pharmaceutical compositions for the treatment of diseases or disorders in a patient (preferably a human) in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, which comprise a compound of the invention, or a pharmaceutically acceptable salt thereof, and a pharmaceutically acceptable carrier.

The invention is also directed to a method for the manufacture of a medicament or a pharmaceutical composition for treating diseases in which TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA comprising combining a compound of the invention or a pharmaceutically acceptable salt thereof, with a pharmaceutically acceptable carrier.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles as well as oxo substituted cycloalkyl groups.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

The term "heteroatom" means O, S or N, selected on an independent basis.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, triazolyl, N-oxides and —C=O derivatives thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, N-oxides thereof and —C=O derivatives thereof. Suitable heteroaryl groups are imidazopyridinyl, indazolyl, imidazothiazolyl, imidazopyrimidinyl, imidazopyridazinyl, imidazothiadiazolyl, quinoxalinyl, and imidazopyrrolyl.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

As used herein —O— includes oxo (e.g., an annular —CH— substituted with oxo is —C(O) or carbonyl.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae (I) can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term TrkA" refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members TrkA, TrkB and TrkC that bind to and mediate the signal transduction derived from the Neurotrophins. Inhibitors of the Trk/neutrophin pathway have been demonstrated to be highly effective in numerous pre-clinical animal models of pain. The compounds of the invention are modulators of the Trk receptors, particularly TrkA.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) disclosed herein as TrkA inhibitors in a patient or subject such as a mammal in need of such activity, comprising the administration of an effective amount of the compound. In addition to humans, a variety of other mammals can be treated according to the method of the present invention.

The compounds of the present invention may have utility in treating or ameliorating pain disorders (including pain associated with cancer, surgery, and bone fracture, acute pain, inflammatory pain and neuropathic pain). The compounds of formula I may also be useful for treating cancers including neuroblastoma, ovarian, pancreatic and colorectal cancer. Other conditions that may be treated by the compounds of the invention include inflammation and certain infectious diseases, interstitial cystitis, painful bladder syndrome, urinary incontinence, asthma, anorexia, atopic dermatitis, and psoriasis. Treatment of demyelination and dysmyelination, by promoting myelination, neuronal survival, and oligodendrocyte differentiation via blocking Sp35-TrkA interaction may also be possible with the compounds of the present invention.

The compounds of formula I may also be useful in the treatment of bone-related diseases (e.g., those involved in bone resorption). Examples of bone-related diseases include metastatic bone disease, treatment-induce bone loss, osteoporosis, rheumatoid arthritis, ankylosing spondylitis, Paget's disease, and periodontal disease. Another bone disorder or disease that can be treated with the compounds of the claimed invention is metastatic tumor-induced osteolysis. Cancers known to cause tumor induced osteolysis are hematological malignancies such as myeloma and lymphoma and solid tumors such as breast, prostate, lung, renal and thyroid.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally mammals such a human being, male or female, in whom Trk-A and/or Trk-B modulation is desired. Thus, an aspect of the present invention is a method of treating diseases with an inhibitor of Trk-A and/or Trk-B comprising administering to said mammal one or more compounds of formula I or a pharmaceutically acceptable salt thereof in an amount effective to treat or prevent said disorder. A particular aspect of the invention is directed to a method of treating pain, cancer, inflammation, neurodegenerative disease or Typanosoma cruzi infection by administering to said mammal a therapeutically effective amount of a compound of formula I or a pharmaceutically acceptable salt thereof. Still another aspect of the present invention is directed to a method of treating osteolytic disease in a mammal by administering a therapeutically effective amount of a compound of formula I or a pharmaceutically acceptable salt thereof. For purposes of this invention mammals include dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds include combinations with agents for the treatment of pain, for example steroids such as dexamethasone, cortisone, and fluticasone, non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; chemotherapeutic agents, opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

Another aspect of the present invention is directed to a pharmaceutical composition comprising a compound of formula I or a pharmaceutically acceptable salt thereof and a pharmaceutically acceptable diluent or carrier. Still another aspect of the present invention is directed to a compound of formula I or a pharmaceutically acceptable salt thereof, for use in the treatment of a condition treatable with an inhibitor of Trk-A and/or Trk-B, such as the disorders, conditions and/or diseases described herein. Still another aspect is directed to use of a compound of formula I or a pharmaceutically acceptable salt thereof in the treatment of pain, cancer, inflammation, neurodegenerative disease or typanosoma cruzi infection.

Dysregulation of Trk kinases either by mutation, overexpression, activation, and/or amplification have been shown to be associated with many cancers. Thus, an embodiment of the instant invention relates to a method of treating a patient diagnosed with a cancer having a dysregulation of TrkA, comprising administering to the patient a therapeutically effective amount of a compound of formula I. A sub-embodiment of this aspect of the invention is realized when the dysregulation of TrkA comprises overexpression of wild-type TrkA (autocrine activation). Another sub-embodiment of this aspect of the invention is realized when the dysregulation of TrkA comprises one or more chromosome translocations or inversions resulting in TrkA gene fusions. Another sub-embodiment of this aspect of the invention is realized when the dysregulation of TrkA comprises one or more deletion, insertions or mutations in the TrkA protein. Another sub-embodiment of this aspect of the invention is realized when the dysregulation of TrkA comprises a deletion of one or more residues from the TrkA protein, resulting in constitutive activity of TrkA kinase. Another sub-embodiment of this aspect of the invention is realized when the dysregulation of TrkA comprises a splice variation in which the expressed protein is an alternatively spliced variant of TrkA having one or more residues deleted resulting in constitutive activity of TrkA kinase.

The dysregulation of TrkA has been shown to be involved with cancers such as neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), glioblastoma (Wadhwa, S., et al., *Journal of Biosciences* 2003, 29 (2), pp. 181-188), medulloblastoma (Gruber-Olipitz, M., et al., *Journal of Proteome Research* 2008, 7 (5), pp. 1932-1944) secretory breast cancer (Euthus D. M., et al., *Cancer Cell* 2002, 2 (5), pp. 347-348), salivary gland cancer (Li, Y. -G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49); adult and/or acute myeloid leukemia (Eguchi, M., et al., *Blood* 1999, 93 (4), pp. 1355-1363); non-small cell lung cancer (Vaishnavi et al., 2013: *Nature Medicine* 19, 1469-1472); large cell neuroendocrine carcinoma (Marchetti et al., 2008: *Human Mutation* 29 (5): 609-616); prostate carcinoma (Papatsoris et al., 2007, *Expert Opinion on Inves. Drugs* 16 (3): 303-309); and pancreatic carcinoma (Zhang et al., 2005, *Oncology Reports* 14: 161-171). Non-selective inhibitors of TrkA, B and C were also found to be effective in hindering tumor growth and stopping tumor metastasis in preclinical models of cancer (Nakagawara, A. (2001) Cancer Letters 169:107-114; and Eric Adriaenssens, E., et al., Cancer Res (2008) 68: (2) pgs. 346-351.

Thus, in another embodiment of the invention a method of treating a patient diagnosed with a cancer having a dysregulation of TrkA, comprising administering to the patient a therapeutically effective amount of a compound of formula I or a pharmaceutically acceptable salt thereof is realized. In another embodiment of the invention a method of treating a patient diagnosed with a cancer selected from the group consisting of non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In another embodiment of the invention the compounds of formula I are useful for treating cancer in combination with one or more additional therapeutic agents. A subembodiment of this aspect of the invention is realized when the additional therapeutic agents are selected from the group consisting of receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab. Another subembodiment of this aspect of the invention is realized when the additional therapeutic agents are selected from signal transduction pathway inhibitors, including sorafenib, trametinib, vemurafenib, everolimus, rapamycin, perifosine, temsirolimus and obataclax.

Still another subembodiment of this aspect of the invention is realized when the additional therapeutic agents are selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Another subembodiment of this aspect of the invention is realized when the additional therapeutic agents are selected from angiogenesis-targeted therapies, including aflibercept and bevacizumab.

Another subembodiment of this aspect of the invention is realized when the additional therapeutic agents are selected from immune-targeted agents, including aldesleukin, ipilimumab, lambrolizumab, nivolumab, and sipuleucel-T.

Another subembodiment of this aspect of the invention is realized when the additional therapeutic agents are selected from agents active against the TrkA pathway, including NGF-targeted biopharmaceuticals such as NGF antibodies and pan Trk inhibitors.

Yet in another subembodiment of this aspect of the invention is realized when the additional therapeutic agent or therapy is radiotherapy, including radioiodide therapy, external-beam radiation and radium 223 therapy.

Another embodiment of the invention is realized by a method of treating cancer in a patient comprising administering to said patient a compound of formula I or a pharmaceutically acceptable salt thereof in combination with at least one of the additional therapies or therapeutic agents disclosed herein. The additional therapeutic agents may be administered with one or more compounds of formula I as part of the same or separate dosage forms, via the same or different routes of administration, and on the same or different administration schedules.

Another embodiment of the invention is realized by a composition comprising a compound of formula I or a pharmaceutically acceptable salt thereof in combination with at least one of the additional therapies or therapeutic agents disclosed herein and optionally at least one pharmaceutically acceptable carrier.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

During any of the synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmic, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The following abbreviations are used throughout the text:
Me: methyl
Et: ethyl
OBu: butyl
t-Bu: tert-butyl
Ar: aryl
Ph: phenyl
Bn: benzyl
Ac: acetyl
DMF•DMA: N,N-dimethylformamide dimethyl acetal
DMSO: dimethylsulfoxide
DMF: N,N-dimethylformamide
THF: tetrahydrofuran
TEA: triethylamine
aq: aqueous
HPLC: high performance liquid chromatography
MS: mass spectrometry
CDI: 1,1'-carbonyldiimidazole
DCE: 1,2-dichloroethane
HCl: hydrochloric acid
° C.: degrees Celsius
BINAP: 2,2'-bis(diphenylphosphino)-1,1'-binaphthalene
ATP: adenosine triphosphate
i-Pr: isopropyl
Py: pyridyl
OAc: acetate
TFA: trifluoroacetic acid
Boc: tert-butoxycarbonyl BOP: (benzotriazol-1-yloxy)tris(dimethylamino)phosphonium hexafluorophosphate
DIEA: N,N-diisopropylethylamine
HOBT: 1-hydroxybenzotriazole
EDC: N-(3-dimethylaminopropyl)-N'-ethylcarbodiimide hydrochloride
PyCLU: chlorodipyrrolidinocarbenium
n-BuLi: n-butyllithium
n-HexLi n-hexyllithium
HATU: O-(7-azabenzotriazol-1-yl)-N,N,N'N'-tetramethyluronium hexafluorophosphate
EDTA: ethylenediaminetetraacetic acid
HMDS: hexamethyldisilazane
min: minutes
h: hours
HPLC: high performance liquid chromatography
LCMS: liquid chromatography-mass spectrometry
SFC: supercritical fluid chromatography
TLC: thin layer chromatography
NMP: 1-methyl-2-pyrrolidinone
MTBE: methyl tert-butyl ether
DMA: N,N-dimethylacetamide
NBS: N-bromosuccinimide
CAN: ammonium cerium(IV) nitrate
dppf: 1,1'-bis(diphenylphosphino)ferrocene
dba: dibenzylideneacetone
DMAP: 4-(dimethylamino)pyridine
PMBCl: 4-methoxybenzyl chloride
DIBAL: diisobutylaluminum hydride
DAST: (diethylamino)sulfur trifluoride
DBU: 1,8-diazabicyclo[5.4.0]undec-7-ene
AIBN: 2-2'-azobisisobutyronitrile
mCPBA: 3-chloroperbenzoic acid
DABCO: diazabicyclo[2.2.2]octane
LDA: lithium diisopropylamide
HOAt: 1-hydroxy-7-azabenzotriazole
LAH: lithium aluminum hydride
AOP: 7-(azabenzotriazol-1-yloxy)tris(dimethylamino)phosphonium hexafluorophosphate
PyAOP: 7-(azabenzotriazol-1-yloxy)tripyrrolidinophosphonium hexafluorophosphate
DCM: dichloromethane
PE: petroleum ether
TMS: trimethylsilyl
Conc: concentrated
More Experimentals to be Added

REACTION SCHEMES

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates the general strategy for preparing the compounds of the present invention in which an carboxylic acid intermediate (1.1) may be activated (for example, via treatment with POCl$_3$, (COCl)$_2$, or SOCl$_2$ to generate the acid chloride) followed by coupling to an amine (1.2) to give the desired product amide 1.3. Various carboxylic acid intermediates, such as those described herein (vide infra), may be coupled to a variety of amines to give the compounds of the present invention. There are many known strategies for effecting such coupling chemistry, including use of coupling reagents, such as EDC with HOBT, PyBOP, HATU, AOP, PyAOP, CDI and the like.

SCHEME 1

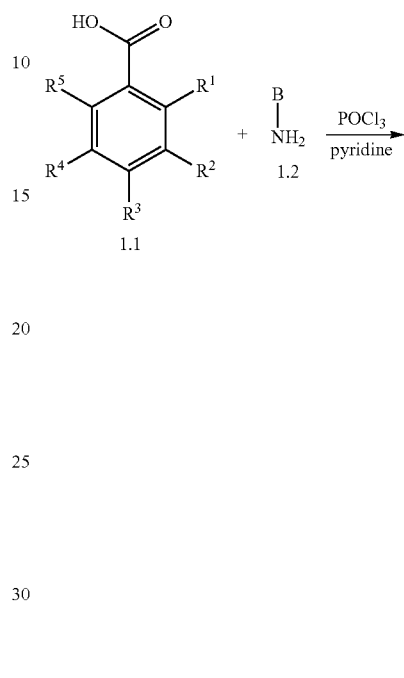

In some cases, various protecting group strategies familiar to one skilled in the art of organic synthesis may be employed to allow preparation of a particular compound of the present invention. This general approach may be successful for the preparation of a range of amide moieties, utilizing a variety of acids and amine intermediates.

Scheme 2 illustrates one of many possible methods that the target may be modified after coupling to form the amide. Treatment of ester 2.1 with a method in which a Grignard reagent (i.e. 2.2) may be added to ester 2.1 to generate tertiary alcohol 2.3.

SCHEME 2

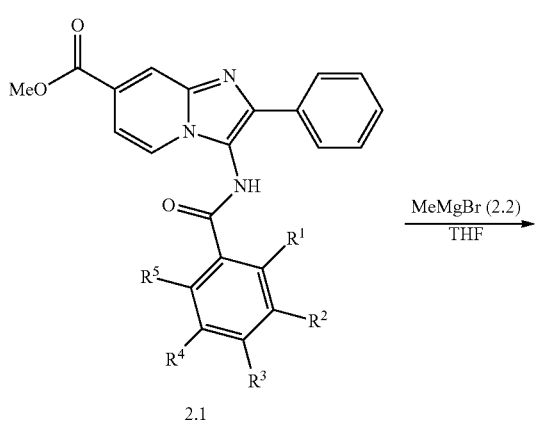

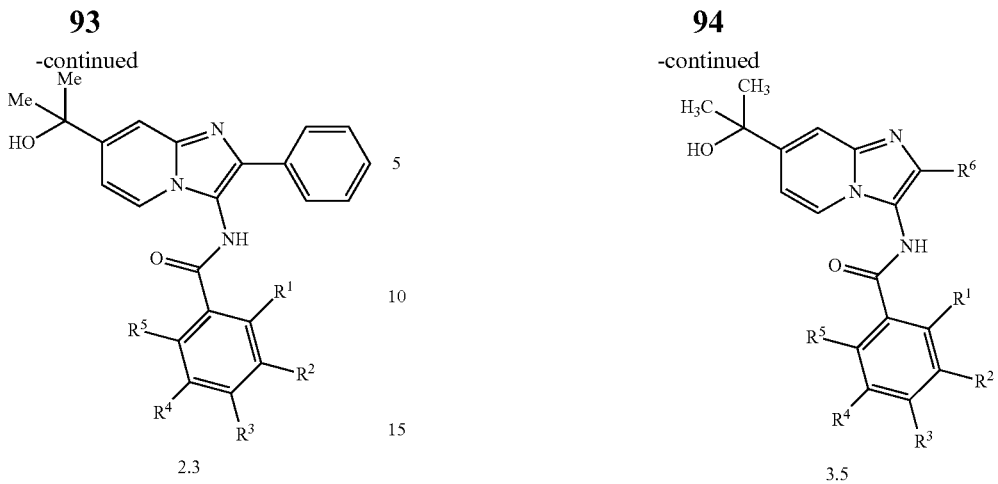

2.3

3.5

Scheme 3 describes a method in which bromide 3.1 undergoes palladium mediated cross-coupling with a vinylenol ether (i.e. 3.2) in the presence of a suitable catalyst and base system, followed by hydrolysis of the intermediate aryl enol by treatment with acidic methanol to afford aryl ketone 3.3. Exposure of ketone (3.3) to a Grignard reagent (3.4) in the presence of cerium trichloride affords the tertiary alcohol 3.5.

Scheme 4 describes a method in which aryl bromide 4.1 undergoes palladium mediated carbonylation under reductive conditions (triethylsilane and base) to afford aldehyde 4.2. Grignard reagent (i.e. 4.3) may be added to aldehyde 4.2 in the presence of cerium trichloroide to generate secondary alcohol 4.4.

SCHEME 3

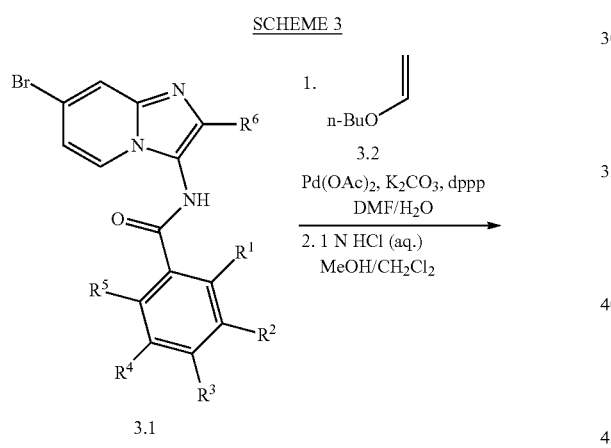

SCHEME 4

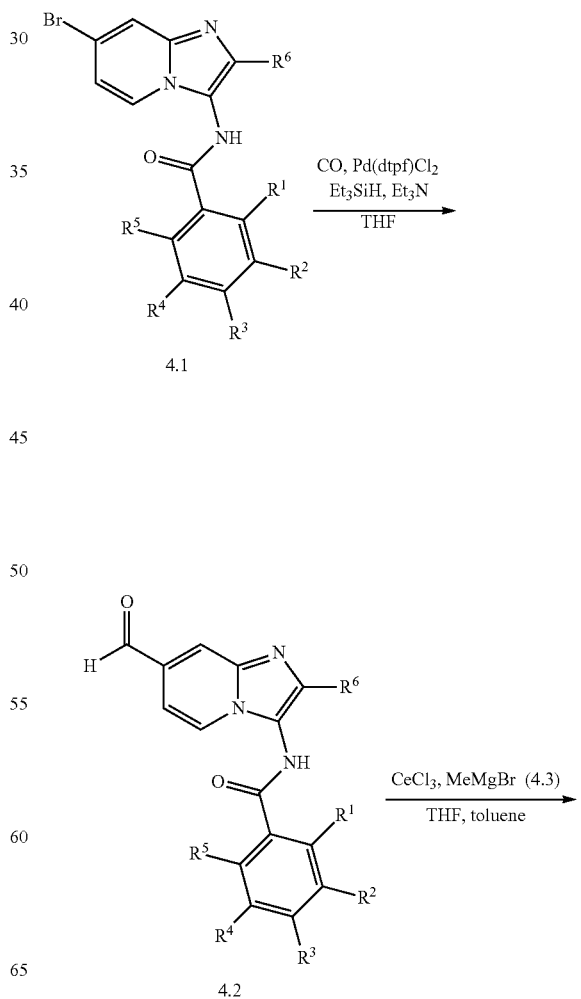

-continued

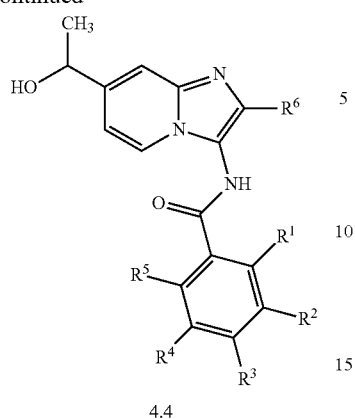

4.4

-continued

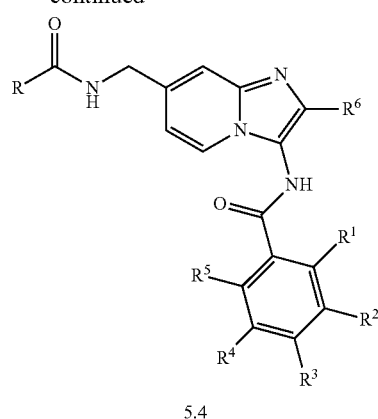

5.4

Scheme 5 describes a method in which a nitrile (i.e. 5.1) may be reduced with Raney Nickel in the presence of H₂ to generate the primary amine 5.2. Treatment of amine 5.2 with an acid (i.e. 5.3) in the presence of a coupling agent such as HATU and EDC affords amide 5.4.

Scheme 6 describes a method in which treatment of aldehyde 6.1 with an amine (i.e. 6.2) in the presence of a reducing agent such as sodium cyanoborohydride and acetic acid affords the amine 6.3.

SCHEME 5

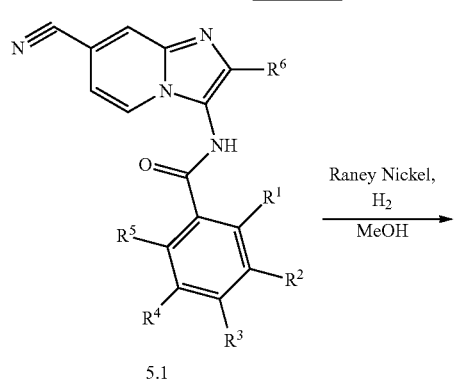

SCHEME 6

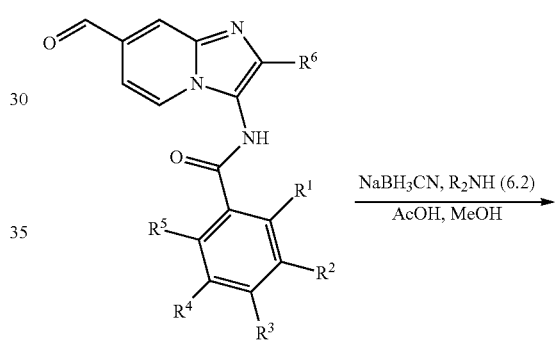

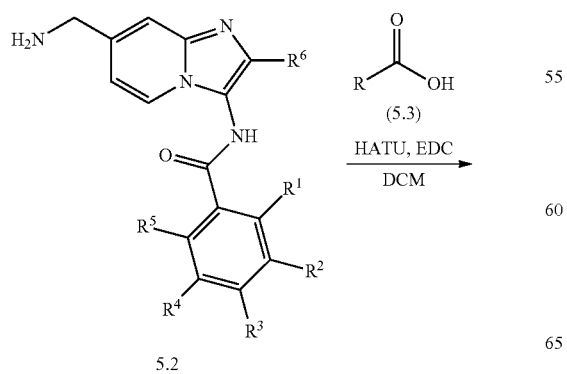

Scheme 7 describes a method in which treatment of nitrile 7.1 with hydrogen peroxide in the presence of a base such as lithium hydroxide in DMSO generates the amide 7.2.

SCHEME 7

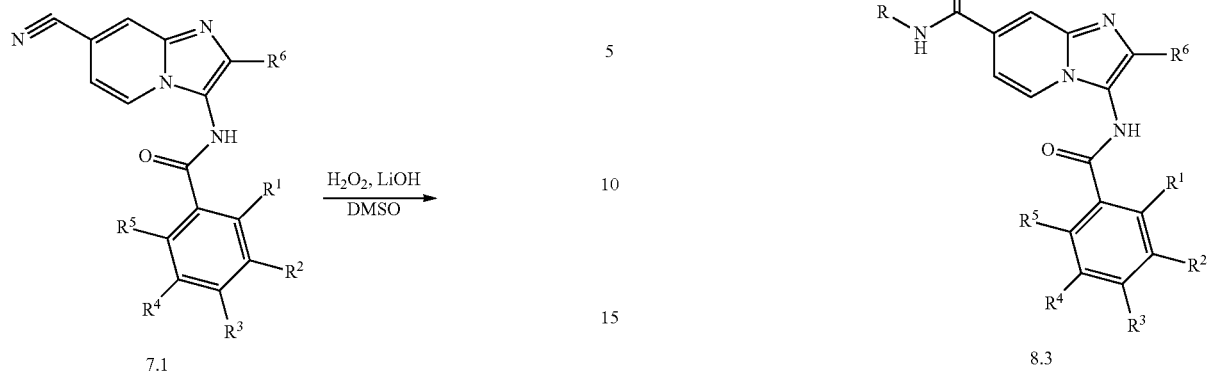

Alternative modifications are known to those in the art and may include, but are not limited to, ether, urea and sulfonamide, and heterocycle formation.

Intermediate amines and acids used in Scheme 1 may be obtained from commercial sources or synthesized using known methods. The following are examples for illustration only.

SCHEME 9

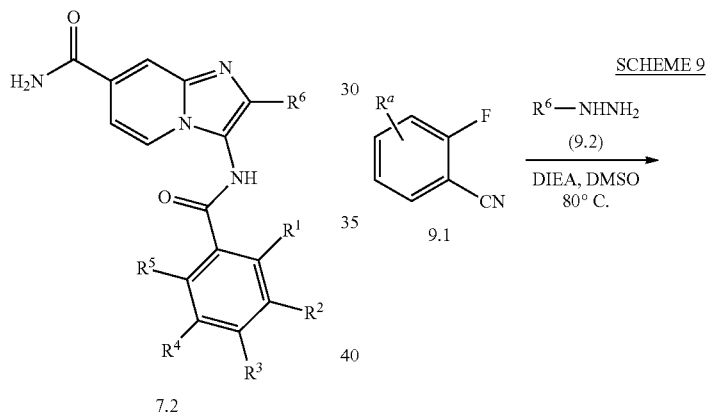

In Scheme 9, intermediate amine of the type 9.3 is described. Treatment of fluoro-nitrile 9.1 with phenyl hydrazine 9.2 in the presence of DIEA in DMSO affords indazole 9.3.

Scheme 8 describes a method in which treatment of acid 8.1 with an amine (8.2) in the presence of a coupling reagent such as HATU and EDC, and base, in DCM to afford the amide 8.3.

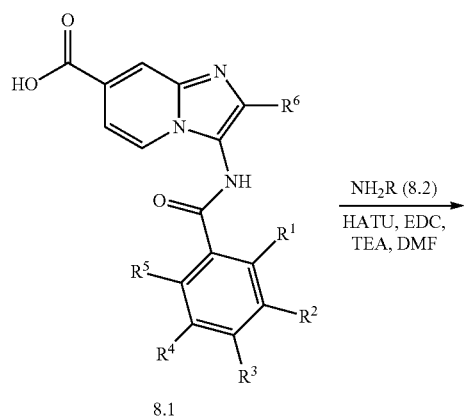

SCHEME 10

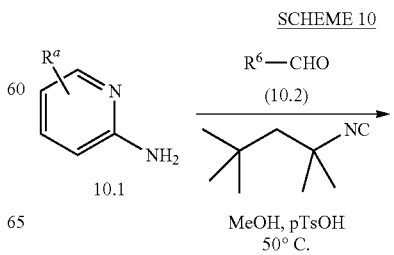

SCHEME 11

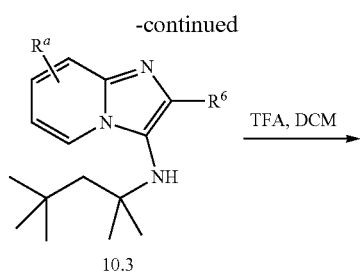

10.3

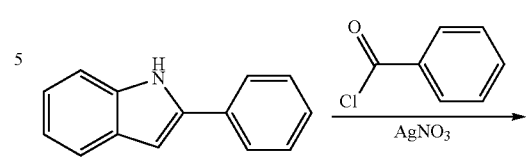

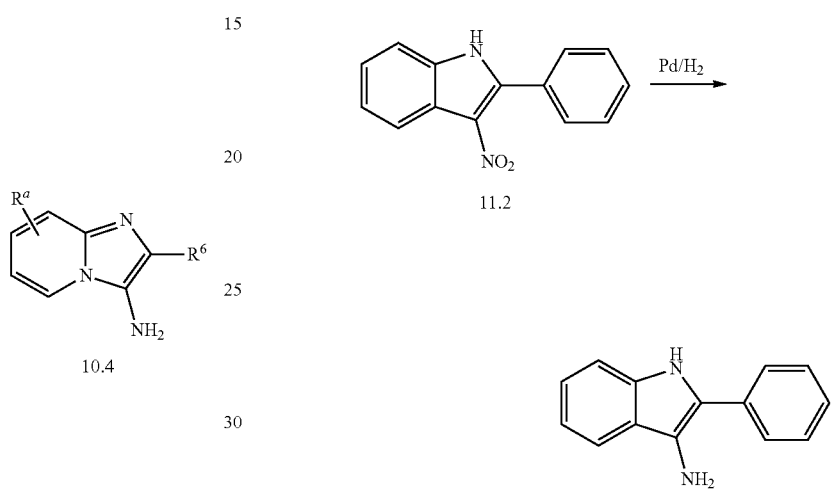

Reaction Scheme 10 illustrates the preparation of the intermediate acids of the type 10.4 which are used to prepare compounds of the invention Aminopyridine 10.1 is converted to imidazopyridine 10.3 by heating in the presence of aldehyde 10.2, tosic acid, and 2-isocyano-2,4,4-trimethyl-pentane in MeOH. Exposure of 10.3 to TFA in DCM effects removal of the 2,4,4-trimethylpentyl group to profile amine 10.4.

Reaction Scheme 11 illustrates the preparation of the intermediate amine of the type 11.3. Nitration of 2-phenyl-1H-indole 11.1 affords nitro indole 11.2 which is treated with Pd/H$_2$ to complete the synthesis of intermediate amine 11.3.

SCHEME 12

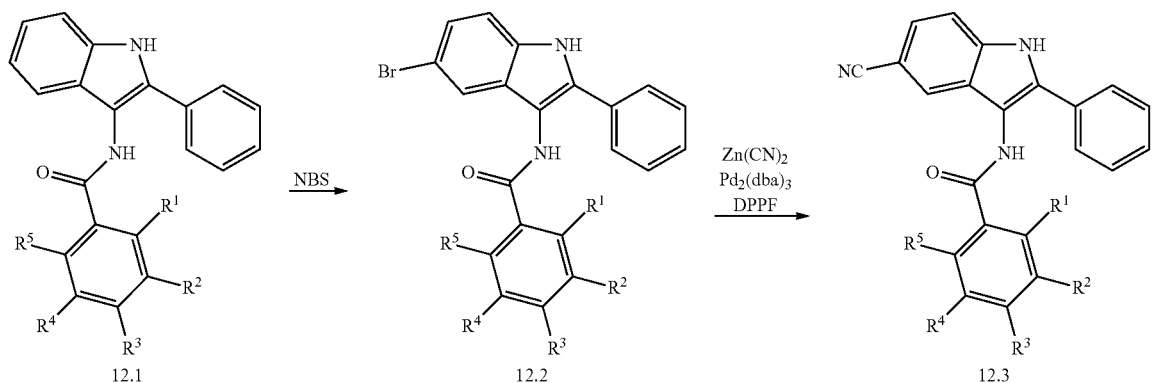

-continued

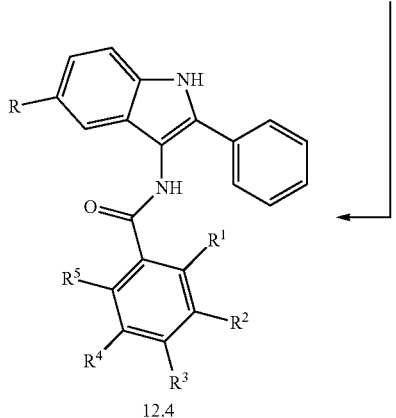

12.4

Reaction Scheme 12 illustrates the preparation of the examples of the type 12.4. Indole 12.1 is treated with NBS to afford bromide 12.2, which is then converted to nitrile 12.3 by exposure to zinc cyanide, $Pd_2(dba)_3$ and DPPF. Then the cyano group in 12.3 is converted to a variety of functionalities in 12.4, where R can be carboxylic acid, methylester, primary amide, methylketone, secondary alcohol and tertiary alcohol.

SCHEME 13

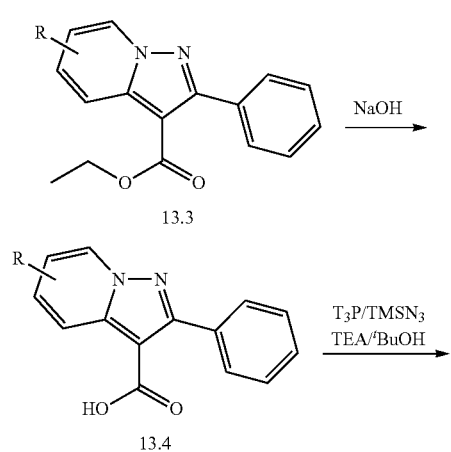

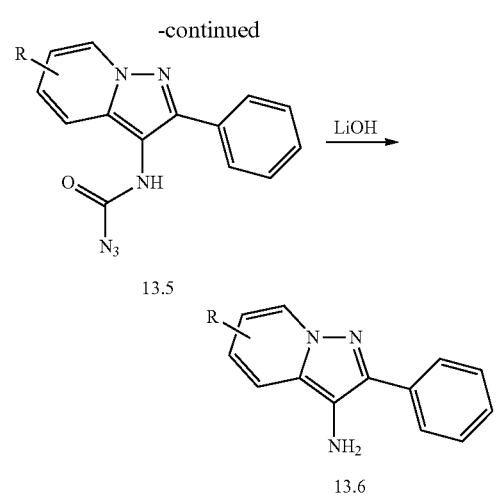

Reaction Scheme 13 illustrates the preparation of the intermediate amines of the type 13.6 which are used to prepare compounds of the invention. [2+3] Cyclization between reagents 13.1 and 13.2 provides pyrazolopyridine 13.3. After saponification of the ester in 13.3, a Curtius type rearrangement affords an intermediate 13.5 with is treated with LiOH to give amine 13.6.

SCHEME 14

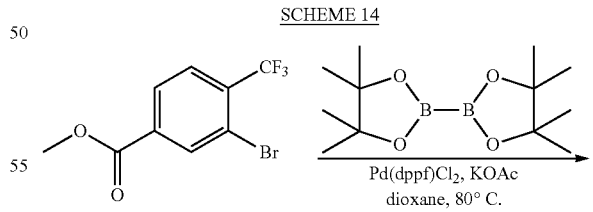
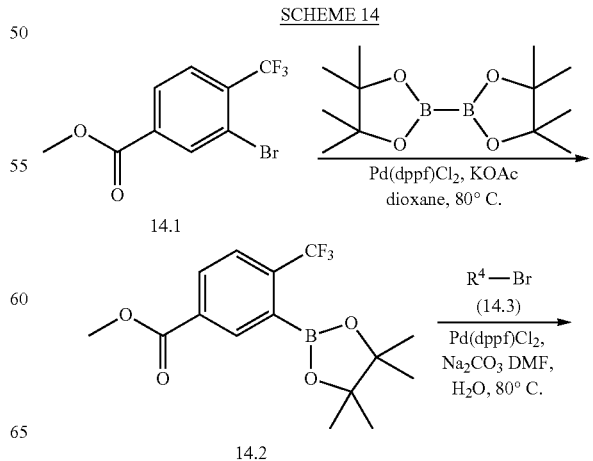

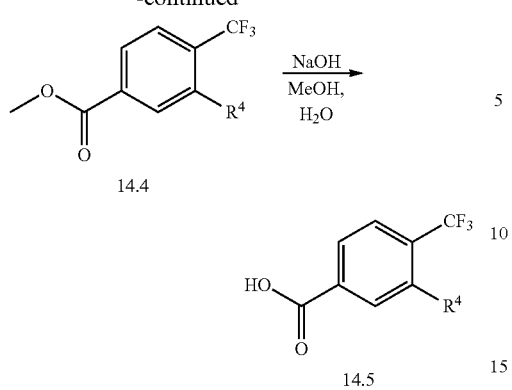

Reaction Scheme 14 illustrates the preparation of the intermediate acids of the type 14.5. Bromide 14.1 is converted to the boronate ester with bis-pin in the presence of a suitable catalyst and base system to afford 14.2. Palladium-catalyzed cross-coupling of the ester 14.2 with an aryl or heteroaryl bromide (14.3) furnishes ester 14.4. Saponification of the ester then affords acid 14.5.

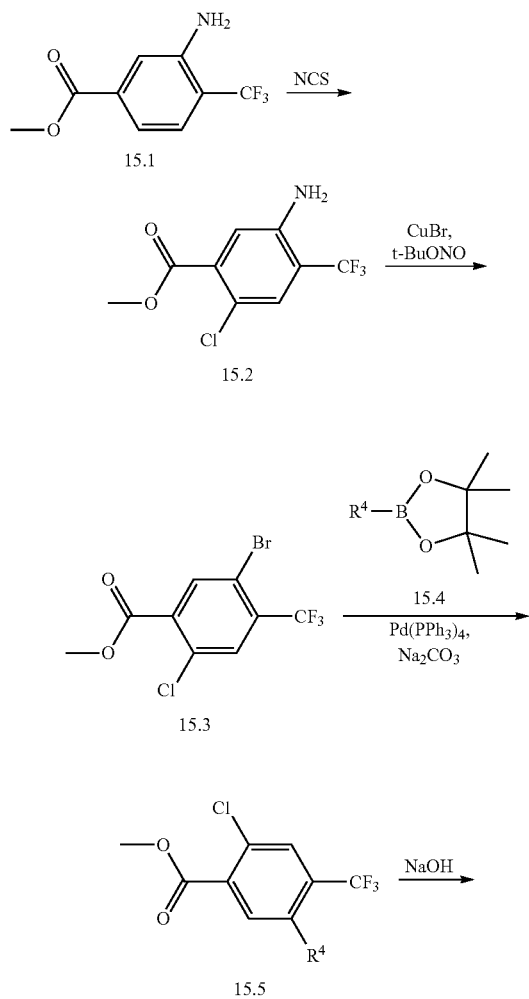

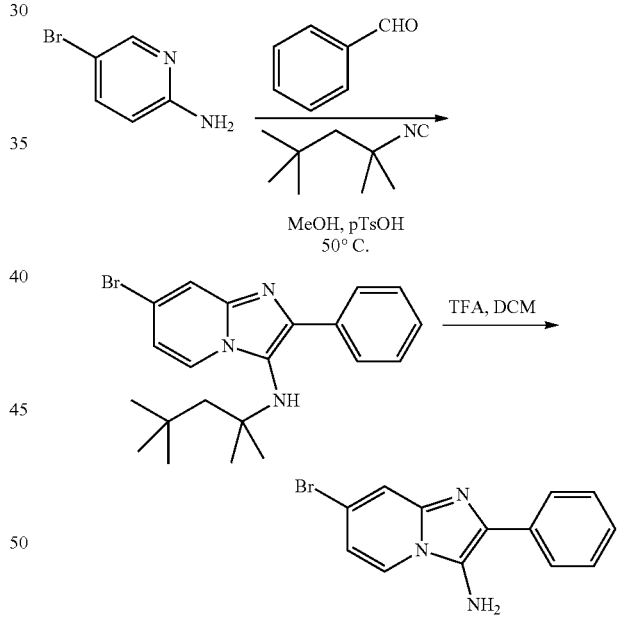

Reaction Scheme 15 illustrates the preparation of the intermediate acids of the type 15.9 which are used to prepare compounds of the invention. Amine 15.1 is treated with NCS to afford chloride 15.2, which is then converted to bromide 15.3 by exposure to t-butylnitrite and copper bromide. Cross-coupling of bromide 15.3 with an aryl or heteroboronic ester 15.4 (or other suitable intermediate) under Suzuki conditions provides ester 15.5. Saponification of the ester then affords acid 15.6.

Specific embodiments of the compounds of the invention, and methods of making them, are described in the Intermediates and Examples herein.

Reaction Scheme for Intermediate A1

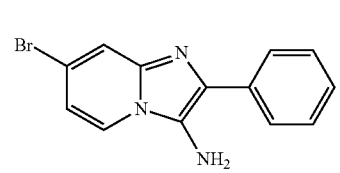

Intermediate A1

7-Bromo-2-phenylimidazo[1,2-a]pyridin-3-amine

Step A: 7-Bromo-2-phenyl-N-(2,4,4-trimethylpentan-2-yl)imidazo[1,2-a]pyridin-3-amine To a solution of 4-bromopyridin-2-amine (1.5 g, 8.7 mmol) and benzaldehyde (0.88 mL, 8.7 mmol) in MeOH (32 mL) was added tosic acid (0.33 g, 1.7 mmol) and 2-isocyano-2,4,4-trimethylpentane (1.5 mL, 8.7 mmol). The resulting mixture was heated at 50° C. for 12 h, then cooled and concentrated. The residue was purified by column chromatography (0 to 100% EtOAc in hexanes) to afford the title compound. MS: m/z=402.0 (M+1). $^1$H NMR (400 MHz, CDCl$_3$) δ 8.10-8.12 (d, J=7.2 Hz, 1H), 7.77-7.79 (m, 2H), 7.72 (s, 1H), 7.41-7.43 (m, 2H), 7.33-7.35 (m, 1H), 6.86-6.88 (m, 1H), 1.01 (s, 9H), 0.92 (s, 6H), 0.90 (s, 2H).

Step B: 7-Bromo-2-phenylimidazo[1,2-a]pyridin-3-amine

To a solution of 7-bromo-2-phenyl-N-(2,4,4-trimethylpentan-2-yl)imidazo[1,2-a]pyridin-3-amine (2.8 g, 7.1 mmol) in DCM (22 mL) was added TFA (22 mL, 280 mmol), and the resulting mixture was stirred for 10 min at ambient temperature. The mixture was carefully basified with saturated aqueous sodium bicarbonate solution, then concentrated. The residue was partitioned between water and a 4:1 mixture of chloroform and ethanol (3×). The combined organic layers were dried over magnesium sulfate and concentrated to afford the title compound. MS: m/z=290.0 (M+1). $^1$H NMR (400 MHz, CDCl$_3$) δ 7.88-7.92 (m, 2H), 7.72 (s, 1H), 7.44-7.48 (m, 3H), 7.33-7.34 (m, 1H), 6.91-6.92 (d, J=7.2 Hz, 1H).

Intermediate A2

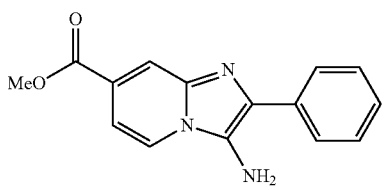 [SMILES: COC(=O)c1ccn2c(N)c(-c3ccccc3)nc2c1]

Methyl 3-amino-2-phenylimidazo[1,2-a]pyridine-7-carboxylate

Step A: Methyl 2-phenyl-3-((2,4,4-trimethylpentan-2-yl)amino)imidazo[1,2-a]pyridine-7-carboxylate To a solution of methyl 2-aminoisonicotinate (2.0 g, 13 mmol) and benzaldehyde (1.3 mL, 13 mmol) in MeOH (49 mL) was added tosic acid (0.50 g, 2.6 mmol) and 2-isocyano-2,4,4-trimethylpentane (2.3 mL, 13 mmol). The resulting mixture was heated at 50° C. for 12 h, then cooled and concentrated. The residue was purified by column chromatography on silica gel (0 to 20% EtOAc in DCM) to afford the title compound. MS: m/z=380.0 (M+1). $^1$H NMR (400 MHz, CDCl$_3$) δ 8.20 (m, 2H), 7.80-7.85 (m, 2H), 7.40-7.45 (m, 2H), 7.35-7.40 (m, 2H), 3.95 (s, 3H), 1.07 (s, 9H), 0.9 (s, 6H), 0.8 (s, 2H).

Step B: Methyl 3-amino-2-phenylimidazo[1,2-a]pyridine-7-carboxylate

To a solution of methyl 2-phenyl-3-((2,4,4-trimethylpentan-2-yl)amino)imidazo[1,2-a]pyridine-7-carboxylate (2.5 g, 6.6 mmol) in DCM (20 mL) was added TFA (20 mL, 260 mmol), and the resulting mixture was stirred for 10 min at ambient temperature. The mixture was carefully basified with saturated aqueous sodium bicarbonate solution and concentrated. The residue was partitioned between water and a 4:1 mixture of chloroform and ethanol (3×). The combined organic layers were dried over magnesium sulfate and concentrated to afford a yellow powder. MS: m/z=268.0 (M+1). $^1$H NMR (400 MHz, CDCl$_3$) δ 8.35 (s, 1H), 7.90-8.0 (m, 3H), 7.30-7.55 (m, 4H), 3.95 (s, 3H).

Intermediate A3

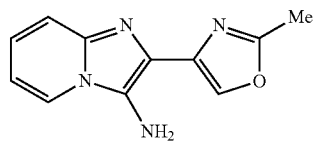 [SMILES: Cc1nc(-c2nc3ccccn3c2N)co1]

2-(2-Methyloxazol-4-yl)imidazo[1,2-a]pyridin-3-amine

A solution of pyridin-2-amine (0.15 g, 1.6 mmol), 2-methyloxazole-4-carbaldehyde (88 mg, 0.80 mmol), and p-toluenesulfonic acid monohydrate (30 mg, 0.16 mmol) in MeOH (2.0 mL) was treated with TMS-CN (100 μL, 0.80 mmol). The resulting mixture was heated at 60° C. for 18 h, then cooled and filtered, washing with MeOH (3×0.5 mL). The filtrate was purified by reverse-phase HPLC (5 to 50% acetonitrile+0.1% trifluoroacetic acid in water) to yield the title compound as a trifluoroacetate salt. MS: m/z=215.0 (M+1).

Reaction Scheme for Intermediate B1

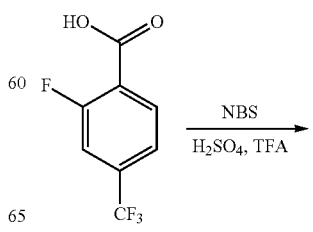

Step B: 2-Fluoro-5-(1-methyl-1H-pyrazol-3-yl)-4-(trifluoromethyl)benzoic acid

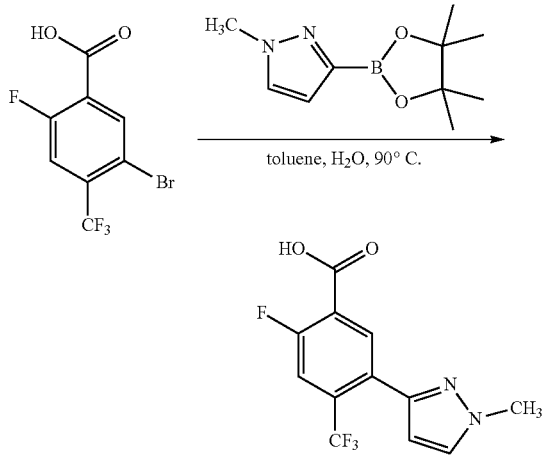

To a deoxygenated mixture of 5-bromo-2-fluoro-4-(trifluoromethyl)benzoic acid (5.0 g, 17 mmol), 1-(methyl)-3-(4,4,5,5-tetramethyl-1,3,2-dioxaborolan-2-yl)-1H-pyrazole (4.35 g, 20.9 mmol) and $K_3PO_4$ (11.1 g, 52.3 mmol) in toluene (55 mL) and $H_2O$ (7 mL) was added 1,1'-bis(di-tert-butylphosphino)ferrocene palladium dichloride (1.14 g, 1.74 mmol). The resulting mixture was heated at 90° C. for 2 h, and then stirred at 50° C. for 18 h. The mixture was cooled and filtered. The filtrate was concentrated and the residue was partitioned between water (200 mL) and EtOAc (300 mL). The aqueous layer was acidified to pH 5 with aqueous HCl solution (1 N) and the resulting precipitate was collected and dried to give the title compound. MS: m/z=289 (M+1). $^1$H NMR (400 MHz, DMSO-$d_6$) δ 13.85 (s, 1H), 8.11 (d, 1H), 7.82 (m, 2H), 6.45 (s, 1H), 3.92 (s, 3H).

The following intermediate was prepared in similar fashion to the procedure described above.

| Compound Number | Structure | Compound Name | LCMS (M + 1) |
|---|---|---|---|
| B2 | 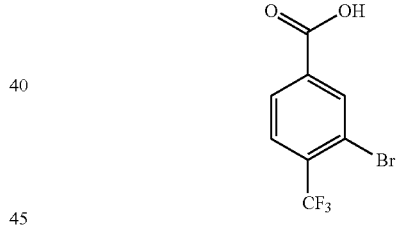 | 2-fluoro-5-(1H-pyrazol-3-yl)-4-(trifluoromethyl)benzoic acid | 275.5 |

Intermediate B1

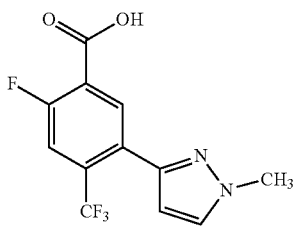 [SMILES: Cn1ccc(-c2cc(C(=O)O)c(F)cc2C(F)(F)F)n1]

2-Fluoro-5-(1-methyl-1H-pyrazol-3-yl)-4-(trifluoromethyl)benzoic acid

Step A: 5-Bromo-2-fluoro-4-(trifluoromethyl)benzoic acid

N-Bromosuccinimide (23.1 g, 130 mmol) was added portionwise to a mixture of 2-fluoro-4-(trifluoromethyl)benzoic acid (15.0 g, 72.1 mmol), sulfuric acid (9.0 mL, 170 mmol, 18 M), and TFA (50.0 mL, 650 mmol) at 50° C. and the resulting mixture was stirred at 50° C. for 18 h. Additional N-bromosuccinimide (3.0 g, 16 mmol) was added and the mixture was stirred at 50° C. for 4 h. The reaction mixture was cooled and water (150 mL) was added. The resulting precipitate was collected and dried to give the title compound. $^1$H NMR (400 MHz, CDCl$_3$) δ 9.90 (s, 1H), 8.35 (d, J=6.3 Hz, 1H), 7.55 (d, J=10.3 Hz, 1H).

Intermediate B3

3-Bromo-4-(trifluoromethyl)benzoic acid

Step A: Methyl 3-bromo-4-(trifluoromethyl)benzoate t-BuONO (79.0 g, 765 mmol) was added to a solution of methyl 3-amino-4-(trifluoromethyl)benzoate (67.0 g, 306 mmol) and CuBr (88.0 g, 612 mmol) in MeCN (1000 mL) at 0° C., and the resulting mixture was warmed to 25° C. and stirred for 12 h. The mixture was then poured into EtOAc (600 mL) and filtered. The filtrate was washed with an aqueous HCl solution (1 M, 200 mL×3), then brine (200 mL), dried over Na$_2$SO$_4$ and concentrated. The residue was purified by column chromatography on silica gel (PE: EA=200:1) to give the title compound. MS: m/z=283, 285 (M+1). $^1$H NMR (400 MHz, CDCl$_3$) δ 8.37 (s, 1H), 8.06 (d, J=8.0 Hz, 1H), 7.77 (d, J=8.0 Hz, 1H), 3.97 (s, 3H).

Step B: 3-Bromo-4-(trifluoromethyl)benzoic acid

A mixture of methyl 3-bromo-4-(trifluoromethyl)benzoate (5.0 g, 17.7 mmol) in aqueous NaOH solution (1 M, 100 mL) was stirred at 25° C. for 12 h. The mixture was acidified to pH 6 with aqueous HCl solution (1 M), and the resulting aqueous mixture was extracted with EtOAc (30 mL×3). The combined organic layers were dried over Na$_2$SO$_4$ and then concentrated to give the title compound. MS: m/z=270 (M+1). $^1$H NMR (400 MHz, CDCl$_3$) δ 8.44 (s, 1H), 8.14 (d, J=8.0 Hz, 1H), 7.83 (d, J=8.0 Hz, 1H).

Reaction Scheme for Intermediate B4

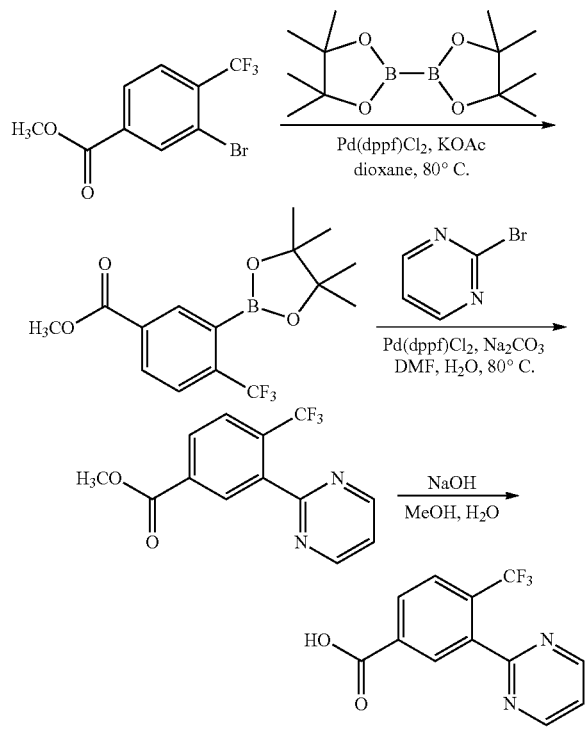

Intermediate B4

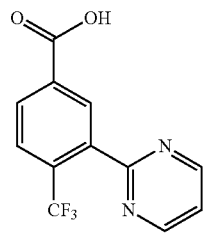 [SMILES: O=C(O)c1ccc(C(F)(F)F)c(-c2ncccn2)c1]

3-(Pyrimidin-2-yl)-4-(trifluoromethyl)benzoyl chloride

Step A: Methyl 3-(4,4,5,5-tetramethyl-1,3,2-dioxaborolan-2-yl)-4-(trifluoromethyl)benzoate To a deoxygenated mixture of methyl 3-bromo-4-(trifluoromethyl)benzoate (20.0 g, 70.7 mmol), 4,4,4',4',5,5,5',5'-octamethyl-2,2'-bi(1,3,2-dioxaborolane) (26.9 g, 106 mmol) and potassium acetate (20.8 g, 212 mmol) in dioxane (300 mL) was added PdCl$_2$(dppf) (2.59 g, 3.50 mmol), and the resulting mixture was heated at 80° C. for 5 h. The mixture was cooled and filtered. The filtrate was concentrated and the residue was partitioned between water (100 mL) and EtOAc (200 mL). The organic layer was washed with brine (100 mL), dried over Na$_2$SO$_4$ and concentrated. The residue was purified by column chromatography on silica gel (PE:EtOAc=15:1) to give the title compound. MS: m/z=331 (M+1).

Step B: Methyl 3-(pyrimidin-2-yl)-4-(trifluoromethyl)benzoate

To a deoxygenated mixture of methyl 3-(4,4,5,5-tetramethyl-1,3,2-dioxaborolan-2-yl)-4-(trifluoromethyl)benzoate (12.0 g, 36.4 mmol), 2-bromopyrimidine (8.67 g, 54.5 mmol) and sodium carbonate (11.6 g, 109 mmol) in DMF (450 mL) and water (60 mL) was added PdCl$_2$(dppf) (1.3 g, 1.8 mmol), and the resulting mixture was heated at 80° C. for 5 h. The mixture was cooled and filtered. The filtrate was concentrated and the residue was partitioned between water (100 mL) and EtOAc (200 mL). The combined organic layer was washed with brine (100 mL), dried over Na$_2$SO$_4$ and concentrated. The residue was purified by column chromatography on silica gel (PE:EtOAc=5:1) to give the title compound. MS: m/z=283 (M+1).

Step C: 3-(Pyrimidin-2-yl)-4-(trifluoromethyl)benzoic acid

A mixture of methyl 3-(pyrimidin-2-yl)-4-(trifluoromethyl)benzoate (7.0 g, 25 mmol) and NaOH (3.0 g, 74 mmol) in a 3:1 mixture of MeOH and H$_2$O (120 mL) was heated at 30° C. for 16 h. The reaction mixture was cooled and then partitioned between water (30 mL) and MTBE (2×60 mL). The aqueous layer was acidified to pH 4 with aqueous HCl solution (2 N). The precipitate was filtered, washed with water and dried to afford the title compound. MS: m/z=269 (M+1). $^1$H NMR (400 MHz, CD$_3$OD) δ 8.92 (d, J=5.0 Hz, 1H), 8.30 (m, 2H), 7.97 (d, J=8.0 Hz, 1H), 7.55 (t, J=4.9 Hz, 1H).

The following intermediates were prepared in similar fashion to the procedure described above.

| Compound Number | Structure | Compound Name | LCMS (M + 1) |
|---|---|---|---|
| B5 | ![structure] | 2-fluoro-5-(pyrimidin-2-yl)-4-(trifluoromethyl)benzoic acid | 301.1 |

-continued
| Compound Number | Structure | Compound Name | LCMS (M + 1) |
|---|---|---|---|
| B6 | 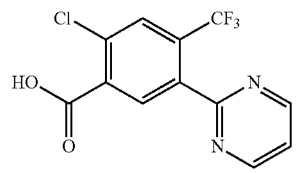 [SMILES: O=C(O)c1cc(-c2ncccn2)c(C(F)(F)F)cc1Cl] | 2-chloro-5-(pyrimidin-2-yl)-4-(trifluoromethyl)benzoic acid | 303.1 |
| B7 | 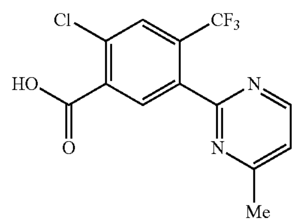 [SMILES: Cc1ccnc(-c2cc(C(=O)O)c(Cl)cc2C(F)(F)F)n1] | 2-chloro-5-(4-methylpyrimidin-2-yl)-4-(trifluoromethyl)benzoic acid | 317.1 |
Reaction Scheme for Intermediate B8
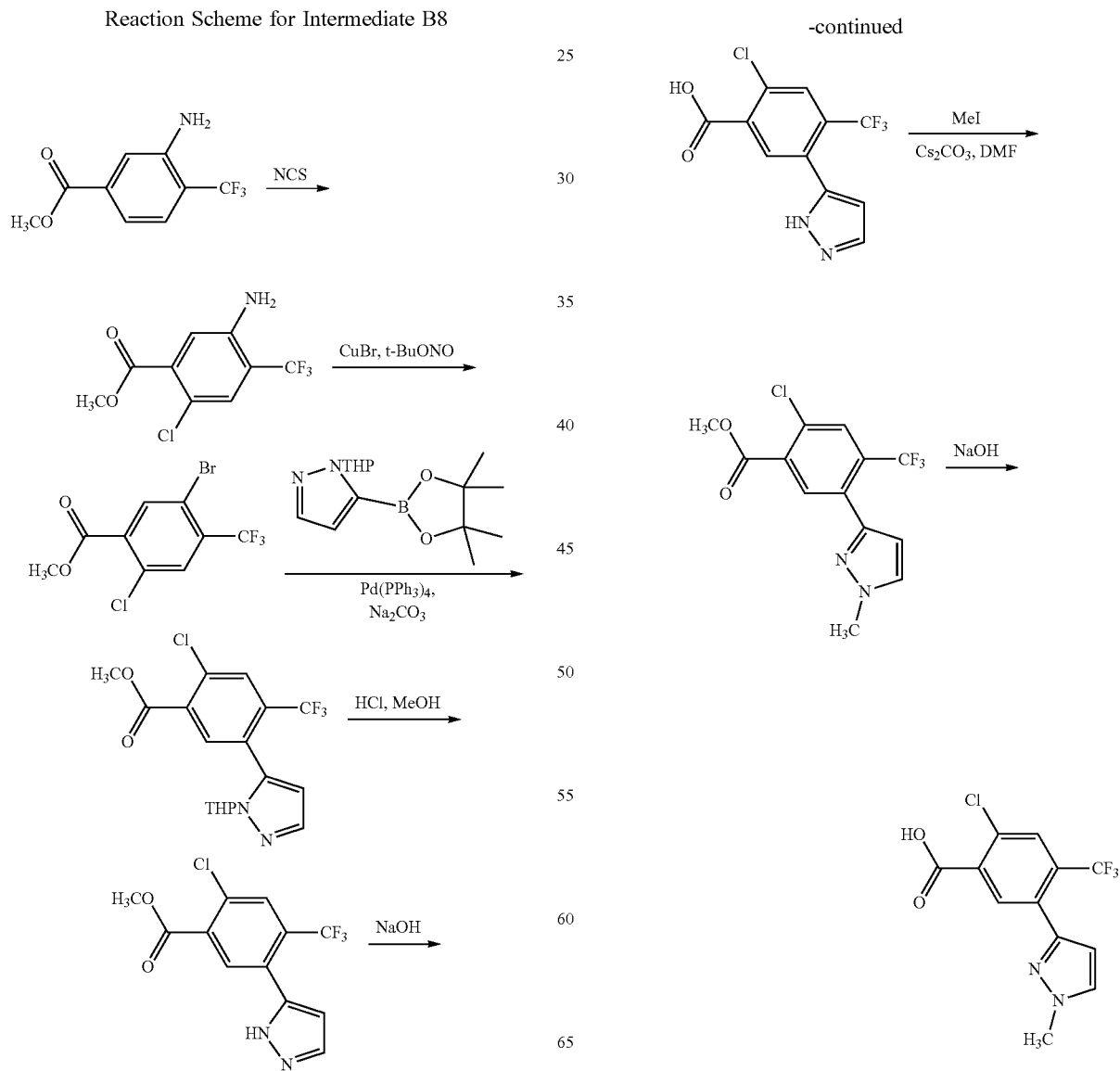

Intermediate B8

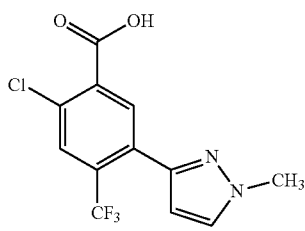 [SMILES: Cn1ccc(-c2cc(C(=O)O)c(Cl)cc2C(F)(F)F)n1]

2-Chloro-5-(1-methyl-1H-pyrazol-3-yl)-4-(trifluoromethyl)benzoic acid

Step A: Methyl 5-amino-2-chloro-4-(trifluoromethyl)benzoate

N-Chlorosuccinimide (8.2 g, 61 mmol) was added to a solution of methyl 3-amino-4-(trifluoromethyl)benzoate (13.2 g, 60.0 mmol) in acetonitrile (200 mL), and the resulting mixture was heated at 80° C. for 20 h. After cooling, the mixture was partitioned between water (500 mL) and EtOAc (2×300 mL). The combined organic layers were washed with brine (200 mL), dried over $Na_2SO_4$, and concentrated. The residue was purified by column chromatography on silica gel (PE:EtOAc=6:1) to afford the title compound. MS: m/z=254 (M+1). $^1$H NMR (400 MHz, $CDCl_3$) δ 7.49 (s, 1H), 7.17 (s, 1H), 3.92 (s, 3H).

Step B: Methyl 5-bromo-2-chloro-4-(trifluoromethyl)benzoate t-Butyl nitrite (4.60 g, 44.5 mmol) and methyl 5-amino-2-chloro-4-(trifluoromethyl)benzoate (4.50 g, 17.8 mmol) were added portionwise to a suspension of copper(I) bromide (5.10 g, 35.6 mmol) in DCM (100 mL). The resulting mixture was heated at 60° C. for 2 h. After cooling, the mixture was diluted with water (50 mL) and aqueous HCl solution (2 M, 50 mL) and then extracted with EtOAc (80 mL×2). The combined organic layers were washed with water (100 mL), then brine (80 mL), dried over $Na_2SO_4$ and concentrated. The residue was purified by flash column chromatography on silica (PE:EtOAc from 50:1 to 30:1) to afford the title compound. MS: m/z=319 (M+1). $^1$H NMR (400 MHz, $CDCl_3$) δ 8.15 (s, 1H), 7.77 (s, 1H), 3.97 (s, 3H).

Step C: Methyl-2-chloro-5-(1-(tetrahydro-2H-pyran-2-yl)-1H-pyrazol-5-yl)-4-(trifluoromethyl)benzoate To a deoxygenated mixture of methyl 5-bromo-2-chloro-4-(trifluoromethyl)benzoate (4.6 g, 14 mmol), 1-(tetrahydro-2H-pyran-2-yl)-5-(4,4,5,5-tetramethyl-1,3,2-dioxaborolan-2-yl)-1H-pyrazole (4.86 g, 17.5 mmol) and $Na_2CO_3$ (4.0 g, 44 mmol) in DMF (150 mL) and $H_2O$ (24 mL) was added $Pd(PPh_3)_4$ (686 mg, 0.58 mmol). The resulting mixture was heated at 80° C. for 5 h, then cooled and filtered. The filtrate was concentrated and the residue was partitioned between water (200 mL) and EtOAc (300 mL). The organic layer was washed with brine (100 mL), dried over $Na_2SO_4$ and concentrated. The residue was purified by column chromatography on silica gel (PE/EtOAc=10/1) to give the title compound. MS: m/z=389 (M+1).

Step D: Methyl 2-chloro-5-(1H-pyrazol-5-yl)-4-(trifluoromethyl)benzoate

A solution of methyl-2-chloro-5-(1-(tetrahydro-2H-pyran-2-yl)-1H-pyrazol-5-yl)-4-(trifluoromethyl)benzoate (2.5 g, 6.4 mmol) in a solution of HCl in MeOH (4 M, 50 mL) was stirred at 15° C. for 1 h and then concentrated to give the title compound. MS: m/z=305 (M+1).

Step E: 2-Chloro-5-(1H-pyrazol-5-yl)-4-(trifluoromethyl)benzoic acid

A solution of NaOH (1.2 g, 0.030 mol) in $H_2O$ (15 mL) was added to a solution of methyl 2-chloro-5-(1H-pyrazol-5-yl)-4-(trifluoromethyl)benzoate (2.3 g, 7.6 mmol) in MeOH (45 mL), and the resulting mixture was stirred at 15° C. for 16 h. The majority of the MeOH was removed under reduced pressure and the remaining aqueous mixture was partitioned between MTBE (50 mL) and water (50 mL). The aqueous layer was acidified to pH 5 with aqueous HCl solution (3 N). The precipitate was filtered, washed with water (50 mL×2) and dried to give the title compound. MS: m/z=291 (M+1).

Step F: Methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl)benzoate A mixture of 2-chloro-5-(1H-pyrazol-5-yl)-4-(trifluoromethyl)benzoic acid (500 mg, 1.72 mmol), $Cs_2CO_3$ (1.7 g, 5.2 mmol) and iodomethane (0.54 mL, 8.6 mmol) in DMF (15 mL) was heated at 80° C. for 2 h. The reaction mixture was cooled and filtered, and the filtrate was concentrated. The residue was partitioned between water (50 mL) and EtOAc (30 mL×3).

The combined organic layers were washed with $H_2O$ (50 mL×3), then brine (50 mL), dried over $Na_2SO_4$ and concentrated to give the title compound. MS: m/z=319 (M+1).

Step G: 2-Chloro-5-(1-methyl-1H-pyrazol-3-yl)-4-(trifluoromethyl)benzoic acid

A solution of NaOH (414 mg, 10.4 mmol) in $H_2O$ (5 mL) was added to a mixture of methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl)benzoate (550 mg, 3.5 mmol) in MeOH (15 mL). The resulting mixture was stirred at 15° C. for 16 h. The majority of the MeOH was removed under reduced pressure and the resulting aqueous solution was partitioned between MTBE (30 mL) and water (30 mL). The aqueous layer was acidified to pH 4 with an aqueous HCl solution (3 N). The resulting suspension was then extracted with EtOAc (50 mL×2). The combined organic layers were washed with brine (50 mL), dried over $Na_2SO_4$ and concentrated. The residue was re-crystallized from MeOH (1 g/5 mL) to give the title compound. MS: m/z=305 (M+1). $^1$H NMR (400 MHz, $CDCl_3$) δ 8.36 (s, 1H), 7.86 (s, 1H), 7.48 (d, J=2.3 Hz, 1H), 6.59 (s, 1H), 4.15 (s, 3H).

The following intermediates were prepared in similar fashion using the corresponding tributylstannane reagent in the palladium catalyzed cross-coupling reaction.

| Compound Number | Structure | Compound Name | LCMS (M + 1) |
|---|---|---|---|
| B9 | ![B9 structure] | 2-chloro-5-(pyridin-2-yl)-4-(trifluoromethyl)benzoic acid | 302 |
| B10 | ![B10 structure] | 2-fluoro-5-(pyridin-2-yl)-4-(trifluoromethyl)benzoic acid | 286.0 |

Intermediate B11

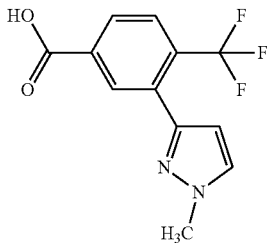 [SMILES: Cn1ccc(-c2cc(C(=O)O)ccc2C(F)(F)F)n1]

3-(1-Methyl-1H-pyrazol-3-yl)-4-(trifluoromethyl)benzoic acid

Step A: 4-Bromo-3-nitrobenzoic acid

4-Bromobenzoic acid (100 g, 0.5 mol) was added portionwise to aqueous $HNO_3$ solution (16 M, 200 mL), keeping the temperature between 0 and 25° C., followed by the dropwise addition of aqueous $H_2SO_4$ solution (18 M, 240 mL) at ambient temperature. The resulting mixture was stirred at ambient temperature for 4 h, and then carefully diluted with 1.5 L of water. The precipitate was filtered, washed with water, and dried to give the title compound. MS: m/z=246.0, 248.0 (M+1). $^1$H NMR (400 MHz, DMSO) δ 8.42 (s, 1H), 8.04 (s, 2H).

Step B: Methyl 4-bromo-3-nitrobenzoate

To a solution of 4-bromo-3-nitrobenzoic acid (115 g, 47.0 mmol) in MeOH (600 mL) was added aqueous $H_2SO_4$ solution (18 M, 200 mL) at ambient temperature. The mixture was heated at reflux for 2 h, and then cooled and filtered. The filtered solid was washed with water and dried to give the title compound. MS: m/z=260, 262 (M+1). $^1$H NMR (400 MHz, DMSO) δ 8.48 (s, 3H), 8.09 (s, 2H), 3.91 (s, 3H).

Step C: Methyl 3-nitro-4-(trifluoromethyl)benzoate

To a solution of methyl 4-bromo-3-nitrobenzoate (175 g, 0.670 mol) in anhydrous DMF (1.0 L) was added CuI (140 g, 0.73 mol) under $N_2$ atmosphere. After stirring at ambient temperature for 10 min, $FSO_2CF_2CO_2CH_3$ (185 mL, 0.730 mol) was added and the vented mixture was heated at 110° C. for 3 h until gas evolution ceased. The mixture was then cooled and filtered through Celite®, washing with EtOAc. The filtrate was concentrated and the residue was partitioned between water (400 mL) and MTBE. The organic layer was washed with water, then brine, dried over anhydrous $Na_2SO_4$ and concentrated. The residue was recrystallized from DCM/MeOH (5/1) to give the title compound. The mother liquor was concentrated and the residue purified by silica gel column chromatography (PE/EtOAc=20/1) to give additional title compound. MS: m/z=250.0 (M+1). $^1$H NMR (400 MHz, DMSO) δ 8.55 (br s, 1H), 8.39 (d, J=7.5 Hz, 1H), 8.19 (d, J=8.0 Hz, 1H), 3.88-3.99 (m, 3H).

Step D: Methyl 3-amino-4-(trifluoromethyl)benzoate

A solution of methyl 3-nitro-4-(trifluoromethyl)benzoate (102 g, 0.410 mol) and 10% Pd/C (10 g, 10 wt %) in MeOH (1.0 L) was stirred under $H_2$ (35 psi) at 30° C. for 12 h. The suspension was filtered through Celite®, washing with MeOH (30 mL×3). The filtrate was concentrated to give the title compound. MS: m/z=220.0 (M+1). $^1$H NMR (400 MHz, DMSO) δ 7.40-7.50 (m, 2H), 7.09-7.15 (m, 1H), 5.92 (s, 2H), 3.82 (s, 3H).

Step E: Methyl 3-bromo-4-(trifluoromethyl)benzoate

Methyl 3-amino-4-(trifluoromethyl)benzoate (40 g, 180 mmol) was added portionwise to a suspension of CuBr (53.0 g, 365 mmol) and t-BuONO (47 g, 460 mmol) in acetonitrile (600 mL) at 0° C. The resulting mixture was stirred at 0° C. for 2 h, and then warmed to 25° C. and stirred for 16 h. The mixture was partitioned between EtOAc and aqueous HCl solution (1 M, 200 mL×4). The organic layer was washed with brine (200 mL), dried over $Na_2SO_4$ and concentrated. The residue was purified by column chromatography on silica gel (PE/EtOAc=200/1) to afford the title compound. MS: m/z=283, 285 (M+1). $^1$H NMR (400 MHz, $CDCl_3$) δ 8.37 (s, 1H), 8.06 (d, J=8.0 Hz, 1H), 7.77 (d, J=8.0 Hz, 1H), 3.97 (s, 3H).

Step F: Methyl 3-(1-(tetrahydro-2H-pyran-2-yl)-1H-pyrazol-5-yl)-4-(trifluoromethyl)benzoate A deoxygenated mixture of methyl 3-bromo-4-(trifluoromethyl)benzoate (5.0 g, 17 mmol), 1-(tetrahydro-2H- pyran-2-yl)-5-(4,4,5,5-tetramethyl-1,3,2-dioxaborolan-2-yl)-1H-pyrazole (5.9 g, 21 mmol), Pd(PPh$_3$)$_4$ (0.80 g, 0.69 mmol), and aqueous Na$_2$CO$_3$ solution (2 M, 26 mL, 53 mmol) in DMF (150 mL) was heated at 70° C. under N$_2$ for 2 h. The mixture was concentrated and the residue was partitioned between EtOAc (200 mL) and water (100 mL). The organic layer was washed with brine (100 mL), then dried over Na$_2$SO$_4$ and concentrated. The residue was purified by column chromatography on silica gel (PE/EtOAc=10/1) to give the title compound. MS: m/z=355.0 (M+1). $^1$H NMR (400 MHz, DMSO) δ 8.37 (s, 1H), 8.06 (d, J=8.0 Hz, 1H), 7.77 (d, J=8.0 Hz, 1H), 3.97 (s, 3H).

Step G: Methyl 3-(1H-pyrazol-5-yl)-4-(trifluoromethyl)benzoate

To a solution of methyl 3-(1-(tetrahydro-2H-pyran-2-yl)-1H-pyrazol-5-yl)-4-(trifluoromethyl)benzoate (5.0 g, 14 mmol) in MeOH (100 mL) was added a solution of HCl in MeOH (40 mL, 4 M). The mixture was stirred at 10° C. for 0.5 h, then concentrated to give the title compound. MS: m/z=271.0 (M+1).

Step H: Methyl 3-(1-methyl-1H-pyrazol-3-yl)-4-(trifluoromethyl)benzoate and methyl 3-(1-methyl-1H-pyrazol-5-yl)-4-(trifluoromethyl)benzoate To a solution of methyl 3-(1H-pyrazol-5-yl)-4-(trifluoromethyl)benzoate (7.0 g, 26 mmol) in DMF (150 mL) was added Cs$_2$CO$_3$ (17 g, 52 mmol) and CH$_3$I (4.8 mL, 78 mmol). The reaction mixture was heated at 80° C. for 2 h, then cooled and concentrated. The residue was partitioned between water (150 mL) and EtOAc (100 mL×3). The combined organic layers were washed with brine (150 mL), dried over Na$_2$SO$_4$ and concentrated to give a mixture of methyl 3-(1-methyl-1H-pyrazol-3-yl)-4-(trifluoromethyl) benzoate and methyl 3-(1-methyl-1H-pyrazol-5-yl)-4-(trifluoromethyl)benzoate. MS: m/z=285.0 (M+1).

Step I: 3-(1-Methyl-1H-pyrazol-3-yl)-4-(trifluoromethyl)benzoic acid

To a solution of methyl 3-(1-methyl-1H-pyrazol-3-yl)-4-(trifluoromethyl)benzoate and methyl 3-(1-methyl-1H-pyrazol-5-yl)-4-(trifluoromethyl)benzoate (6.5 g, 23 mmol) in MeOH (100 mL) was added aqueous NaOH solution (35 mL, 2 M). The mixture was heated at 50° C. for 50 min, then cooled. The majority of the MeOH was removed under reduced pressure and the resulting aqueous solution was partitioned between EtOAc (100 mL) and water (150 mL). The aqueous layer was acidified to pH 5 with aqueous HCl solution (1 N) and then further extracted with EtOAc (150 mL×2). The combined organic layers were washed with brine (150 mL), dried over anhydrous Na$_2$SO$_4$ and concentrated. The residue was purified by recrystallization from MeOH (1 g/5 mL) to provide the title compound. MS: m/z=271.0 (M+1). $^1$H NMR (400 MHz, DMSO) δ 13.43-13.68 (m, 1H) 8.18-8.24 (m, 1H), 8.05-8.12 (m, 1H), 7.92-7.99 (m, 1H), 7.77-7.84 (m, 1H), 6.43-6.52 (m, 1H), 3.93 (s, 3H).

The following intermediate was prepared in similar fashion to the procedure described above.

| Compound Number | Structure | Compound Name | LCMS (M + 1) |
|---|---|---|---|
| B12 | 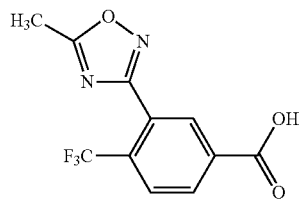 [SMILES: Cc1nc(-c2cc(C(=O)O)ccc2C(F)(F)F)no1] | 3-(1H-pyrazol-3-yl)-4-(trifluoromethyl)benzoic acid | 257.1 |

INTERMEDIATE B13

3-(5-Methyl-1,2,4-oxadiazol-3-yl)-4-(trifluoromethyl)benzoic acid

Step A: Methyl 3-cyano-4-(trifluoromethyl)benzoate

To a mixture of methyl 3-amino-4-(trifluoromethyl)benzoate (15 g, 0.073 mol) and aqueous HCl solution (12 M, 24 mL) in H$_2$O (100 mL) at 0° C. was added dropwise a solution of NaNO$_2$ (5.5 g, 0.080 mol) in H$_2$O (30 mL). The reaction was stirred at 0° C. for 30 min and then added dropwise to a slurry of CuCN (7.1 g, 0.080 mol) and KCN (8.4 g, 0.13 mol) in H$_2$O (200 mL), while maintaining the internal temperature between 5-10° C. After the addition was complete, the reaction was heated at 80° C. for 1 h. The mixture was cooled and the solution was extracted with EtOAc (200 mL×4). The combined organic layers were dried over anhydrous Na$_2$SO$_4$ and concentrated. The residue was purified by column chromatography on silica gel (2% EtOAc in PE) to afford the title compound. MS: m/z=230.0 (M+1). $^1$H NMR (400 MHz, CDCl$_3$) δ 8.46-8.53 (m, 1H), 8.33-8.42 (m, 1H), 7.87-7.95 (m, 1H), 4.01 (s, 3H).

Step B: Methyl 3-(N'-hydroxycarbamimidoyl)-4-(trifluoromethyl)benzoate

To a mixture of methyl 3-cyano-4-(trifluoromethyl)benzoate (1.6 g, 7.0 mmol) and hydroxylamine hydrochloride (0.98 g, 14 mmol) in MeOH (20 mL) was added NaHCO$_3$ (2.3 g, 28 mmol). The resulting mixture was heated at 85° C. for 5 h, then cooled and concentrated. The residue was purified by column chromatography on silica gel (40% EtOAc in PE) to afford the title compound. MS: m/z=263.0

(M+1). $^1$H NMR (400 MHz, CDCl$_3$) δ 8.26 (s, 1H), 8.18-8.21 (d, J=8.4 Hz, 1H), 7.80-7.83 (d, J=8.0 Hz, 1H), 7.52 (s, 1H), 4.89 (s, 2H), 3.96 (s, 3H).

Step C: Methyl 3-(N-acetyl-N'-hydroxycarbamimidoyl)-4-(trifluoromethyl)benzoate

To a solution of methyl 3-(N'-hydroxycarbamimidoyl)-4-(trifluoromethyl)benzoate (282 mg, 1.07 mmol) and TEA (0.30 mL, 2.14 mmol) in anhydrous DCM (20 mL) at 25° C. was added AcCl (0.083 mL, 1.18 mmol). The resulting mixture was heated at 30° C. for 20 min, then cooled and concentrated to give the title compound. MS: m/z=305.0 (M+1).

Step D: Methyl 3-(5-methyl-1,2,4-oxadiazol-3-yl)-4-(trifluoromethyl)benzoate

A solution of methyl 3-(N-acetyl-N'-hydroxycarbamimidoyl)-4-(trifluoromethyl)benzoate (0.28 g, 0.93 mmol) in toluene (10 mL) was heated at 110° C. for 2 h, then cooled and concentrated. The residue was purified by column chromatography on silica gel (30% EtOAc in PE) to afford the title compound. MS: m/z=287.0 (M+1). $^1$H NMR (400 MHz, CDCl$_3$) δ 8.37-8.49 (m, 1H), 8.22-8.32 (m, 1H), 7.87-7.99 (m, 1H), 3.96 (s, 3H), 2.70 (s, 3H).

Step E: 3-(5-Methyl-1,2,4-oxadiazol-3-yl)-4-(trifluoromethyl)benzoic acid

To a solution of methyl 3-(5-methyl-1,2,4-oxadiazol-3-yl)-4-(trifluoromethyl)benzoate (0.13 g, 0.45 mmol) in MeOH (2.0 mL) was added aqueous NaOH solution (2.0 mL, 1 M). The resulting mixture was heated at 50° C. for 1 h, and then cooled and acidified to pH 5 with aqueous HCl solution (1 M). The aqueous mixture was extracted with EtOAc (10 mL×3). The combined organic layers were dried over anhydrous Na$_2$SO$_4$ and concentrated to give the title compound. MS: m/z=273.0 (M+1). $^1$H NMR (400 MHz, CDCl$_3$) δ 8.47 (s, 1H), 8.27 (d, J=8.0 Hz, 1H), 7.91 (d, J=8.8 Hz, 1H), 2.69 (s, 3H).

Intermediate B14

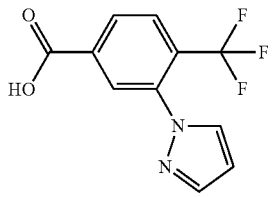 [SMILES: O=C(O)c1ccc(C(F)(F)F)c(-n2cccn2)c1]

3-(1H-Pyrazol-1-yl)-4-(trifluoromethyl)benzoic acid

Step A: Methyl 3-(1H-pyrazol-1-yl)-4-(trifluoromethyl)benzoate

A mixture of methyl 3-bromo-4-(trifluoromethyl)benzoate (0.50 g, 1.8 mmol), pyrazole (0.18 g, 2.6 mmol), Cs$_2$CO$_3$ (1.4 g, 4.4 mmol), CuI (670 mg, 3.52 mmol) and 1,10-phenanthroline (0.13 g, 0.70 mmol) in anhydrous toluene (15 mL) was heated at 140° C. for 1 h under microwave irradiation. After cooling, the reaction mixture was diluted with EtOAc (50 mL) and filtered. The filtrate was concentrated and the residue was purified by preparative TLC (PE/EA=5/1) to give the title compound. MS: m/z=271.0 (M+1).

Step B: 3-(1H-Pyrazol-1-yl)-4-(trifluoromethyl)benzoic acid

To a solution of methyl 3-(1H-pyrazol-1-yl)-4-(trifluoromethyl)benzoate (0.20 g, 0.74 mmol) in MeOH (15 mL) was added aqueous NaOH solution (3.0 mL, 2 M). The mixture was heated at 50° C. for 10 min. The majority of the MeOH was removed under reduced pressure and the resulting aqueous solution was partitioned between EtOAc (30 mL) and water (20 mL). The aqueous layer was acidified to pH 5 with aqueous HCl solution (1 M) and then extracted with EtOAc (30 mL×2). The combined organic layers were washed with brine (30 mL), dried over anhydrous Na$_2$SO$_4$ and concentrated to give the title compound. MS: m/z=257.0 (M+1). $^1$H NMR (400 MHz, DMSO) δ 8.19 (m, 1H), 8.13 (m, 1H), 8.07 (m, 1H), 7.97 (m, 1H), 7.78 (m, 1H), 6.55 (m, 1H).

Intermediate B15

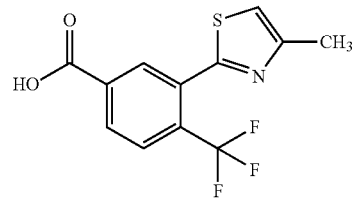 [SMILES: Cc1csc(-c2cc(C(=O)O)ccc2C(F)(F)F)n1]

3-(4-Methylthiazol-2-yl)-4-(trifluoromethyl)benzoic acid

Step A: 3-Amino-4-(trifluoromethyl)benzoic acid

A mixture of 3-nitro-4-(trifluoromethyl)benzoic acid (1.0 g, 4.3 mmol) and 10% Pd/C (0.20 g, 5% wt) in MeOH (20 mL) was stirred under H$_2$ atmosphere (15 psi) at ambient temperature for 12 h. The catalyst was filtered and the filtrate concentrated to afford the title compound. MS: m/z=206.0 (M+1). $^1$H NMR (400 MHz, DMSO) δ 7.46 (s, 1H), 7.38-7.45 (m, 1H), 7.13 (d, J=8.3 Hz, 1H), 5.84 (s, 2H).

Step B: Methyl 3-amino-4-(trifluoromethyl)benzoate

A mixture of 3-amino-4-(trifluoromethyl)benzoic acid (3.4 g, 16 mmol) and aqueous H$_2$SO$_4$ solution (18 M, 2.0 mL) in MeOH (20 mL) was heated at reflux until the starting material was consumed. The mixture was cooled, then neutralized to pH 7 by the addition of aqueous NaOH solution (1N). The aqueous mixture was extracted with EtOAc (10 mL×3), and the combined organic combined layers were washed with brine, dried over Na$_2$SO$_4$ and concentrated to afford the title compound. MS: m/z=220.0 (M+1). $^1$H NMR (400 MHz, CDCl$_3$) δ 7.46-7.52 (m, 1H), 7.42 (s, 2H), 4.30 (br s, 2H), 3.92 (s, 3H).

Step C: Methyl 3-cyano-4-(trifluoromethyl)benzoate

To a mixture of methyl 3-amino-4-(trifluoromethyl)benzoate (3.2 g, 15 mmol) and aqueous HCl solution (12 M, 3.5 mL) in water (20 mL) was added dropwise a solution of NaNO$_2$ (1.2 g, 17 mmol) in water (7.0 mL) at 5° C. The resulting mixture was stirred for 30 min at 5° C. and then added dropwise to a slurry of CuCN (1.3 g, 15 mmol) and KCN (1.6 g, 25 mmol) in water (4 mL), while maintaining the internal temperature between 5-10° C. The mixture was stirred at 10° C. for 30 min and then heated at 80° C. for 1 h. After cooling, the mixture was extracted with DCM (30 mL×3). The combined organic layers were washed with brine, dried over Na$_2$SO$_4$ and concentrated to afford the title compound. MS: m/z=230 (M+1). $^1$H NMR (400 MHz, CDCl$_3$) δ 8.45-8.53 (m, 1H), 8.33-8.40 (m, 1H), 7.91 (d, 1H, J=8.5 Hz), 4.01 (s, 3H).

Step D: Methyl 3-carbamothioyl-4-(trifluoromethyl)benzoate

H$_2$S gas was bubbled through a solution of methyl 3-cyano-4-(trifluoromethyl)benzoate (0.10 g, 0.61 mmol) and TEA (0.20 mL, 1.4 mmol) in pyridine (10 mL) at ambient temperature for 30 min. The mixture was concentrated, and the residue was partitioned between water and EtOAc (10 mL×3). The combined organic layers were washed with brine, dried over Na$_2$SO$_4$ and concentrated. The residue was purified by column chromatography on silica gel (PE:EtOAc=5:1) to afford the title compound. MS: m/z=264.0 (M+1). $^1$H NMR (400 MHz, CDCl$_3$) δ 8.25-8.31 (m, 1H), 8.09-8.17 (m, 1H), 7.75 (d, J=8.0 Hz, 1H), 4.45-4.68 (m, 2H), 3.96 (s, 3H).

Step E: Methyl 3-(4-hydroxy-4-methyl-4,5-dihydrothiazol-2-yl)-4-(trifluoromethyl)benzoate A mixture of methyl 3-carbamothioyl-4-(trifluoromethyl) benzoate (100 mg, 0.38 mmol), TEA (0.20 mL, 1.4 mmol) and 1-chloropropan-2-one (0.033 mL, 0.42 mmol) in DMF (3.0 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EA=3:1) to afford the title compound. MS: m/z=320.0 (M+1).

Step F: 3-(4-Methylthiazol-2-yl)-4-(trifluoromethyl) benzoic acid

A solution of methyl 3-(4-hydroxy-4-methyl-4,5-dihydrothiazol-2-yl)-4-(trifluoromethyl)-benzoate in aqueous NaOH solution (1 M, 10 mL) was stirred at ambient temperature for 8 h. The mixture was acidified to pH 5 with aqueous HCl solution (1 M), then extracted with EtOAc (10 mL×3). The combined organic layers were washed with brine, dried over Na$_2$SO$_4$ and then concentrated to afford the title compound. MS: m/z=288.0 (M+1). $^1$H NMR (400 MHz, CDCl$_3$) δ 8.23-8.34 (m, 1H), 8.06-8.17 (m, 1H), 7.68-7.83 (m, 1H), 6.97-7.10 (m, 1H), 2.50 (s, 3H).

Intermediate B16

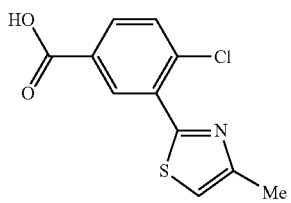 [SMILES: Cc1csc(-c2cc(C(=O)O)ccc2Cl)n1]

4-Chloro-3-(4-methylthiazol-2-yl)benzoic acid

Step A: Methyl 4-chloro-3-cyanobenzoate

To a mixture of methyl 3-amino-4-chlorobenzoate (10 g, 54 mmol) and aqueous HCl solution (12 M, 15 mL) in water (80 mL) at 0° C. was added dropwise a solution of NaNO$_2$ (4.5 g, 60 mmol) in water (18 mL) at 0° C. The reaction was stirred for 30 min at 0° C. and then added dropwise to a slurry of CuCN (4.9 g, 54 mmol) and KCN (6.0 g, 92 mmol) in water (40 mL), while maintaining the temperature between 5-10° C. The reaction mixture was stirred at 10° C. for 30 min and then heated at 80° C. for 1 h. After cooling, the mixture was extracted with DCM. The organic layer was washed with brine, dried over Na$_2$SO$_4$ and then concentrated to afford the title compound. MS: m/z=196.0 (M+1). $^1$H NMR (400 MHz, CDCl$_3$) δ 8.34 (d, J=2.0 Hz, 1H), 8.17-8.20 (m, 1H), 7.61 (d, J=8.4 Hz, 1H), 3.96 (s, 3H).

Step B: Methyl 3-carbamothioyl-4-chlorobenzoate

H$_2$S gas was bubbled through a solution of methyl 4-chloro-3-cyanobenzoate (3.0 g, 15 mmol) and TEA (2.13 mL, 15.3 mmol) in pyridine (15 mL) at ambient temperature for 1 h. The reaction mixture was concentrated and the residue was purified by column chromatography (PE:EtOAc=10:1) to give the title compound. MS: m/z=230.0 (M+1). $^1$H NMR (400 MHz, CDCl$_3$) δ 8.29 (d, J=1.6 Hz, 1H), 7.95-7.97 (m, 2H), 7.45 (d, J=8.4 Hz, 1H), 7.26 (s, 1H), 3.92 (s, 3H).

Step C: Methyl 4-chloro-3-(4-methylthiazol-2-yl)benzoate

A mixture of methyl 3-carbamothioyl-4-(trifluoromethyl) benzoate (1.0 g, 4.3 mmol), TEA (0.20 mL, 1.4 mmol) and 1-chloropropan-2-one (0.80 g, 8.6 mmol) in DMF (10 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EtOAc=3:1) to afford the title compound. MS: m/z=268.0 (M+1). $^1$H NMR (400 MHz, CDCl$_3$) δ 8.29 (d, J=2.0 Hz, 1H), 7.97-8.00 (m, 1H), 7.76 (d, J=8.0 Hz, 1H), 7.09 (s, 1H), 3.92 (s, 3H), 2.56 (s, 3H).

Step D: 4-Chloro-3-(4-methylthiazol-2-yl)benzoic acid

A mixture of methyl 4-chloro-3-(4-methylthiazol-2-yl) benzoate (0.40 g, 2.0 mmol) in aqueous NaOH solution (1 M, 10 mL) was stirred at ambient temperature for 8 h. The mixture was acidified to pH 5 with aqueous HCl solution (2 M) and then extracted with EtOAc (10 mL×3). The combined organic layers were washed with brine, dried over Na$_2$SO$_4$ and then concentrated to afford the title compound. MS: m/z=254.0 (M+1).

Intermediate B17

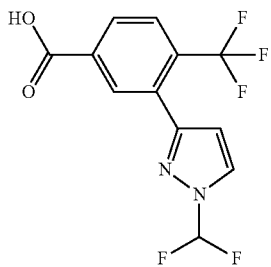 [SMILES: O=C(O)c1ccc(C(F)(F)F)c(-c2ccn(C(F)F)n2)c1]

3-(1-(Difluoromethyl)-1H-pyrazol-3-yl)-4-(trifluoromethyl)benzoic acid

A solution of methyl 3-(1H-pyrazol-5-yl)-4-(trifluoromethyl)benzoate (50 mg, 0.18 mmol), sodium chlorodifluoroacetate (34 mg, 0.22 mmol), and 18-crown-6 (9.8 mg, 0.037 mmol) in acetonitrile (1 mL) was heated at reflux for 40 h. Additional sodium chlorodifluoroacetate (34 mg, 0.22 mmol) was added after 18 and 22 h. The reaction mixture was cooled to ambient temperature and aqueous NaOH solution (10 M, 0.056 mL, 0.55 mmol) was added. The resulting mixture was heated at 50° C. for 2 h. The mixture was cooled and then filtered, washing with acetonitrile (1 mL) and DMF (1 mL). The filtrate was purified by reverse-phase HPLC (5-95% acetonitrile+0.1% trifluoroacetic acid in water) to provide the title compound. MS: m/z=307.0 (M+1).

Intermediate B18

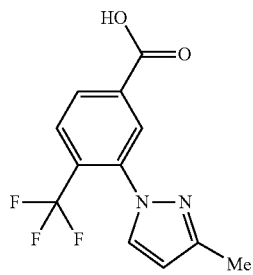 [SMILES: Cc1ccn(-c2cc(C(=O)O)ccc2C(F)(F)F)n1]

3-(3-Methyl-1H-pyrazol-1-yl)-4-(trifluoromethyl)benzoic acid

A deoxygenated solution of 3-methyl-1H-pyrazole (0.120 mL, 1.49 mmol), 3-bromo-4-(trifluoromethyl)benzoic acid (0.20 g, 0.74 mmol), copper(I) iodide (28 mg, 0.15 mmol), cesium carbonate (0.48 g, 1.5 mmol), and trans-N,N-dimethylcyclohexane-1,2-diamine (0.023 mL, 0.15 mmol) in dioxane (1.0 mL) was heated at reflux for 18 h. The mixture was cooled and filtered, washing with DMF (1.5 mL). The filtrate was purified by reverse-phase HPLC (5-95% acetonitrile+0.1% trifluoroacetic acid in water) to afford the title compound. MS: m/z=271.0 (M+1).

Intermediate B19

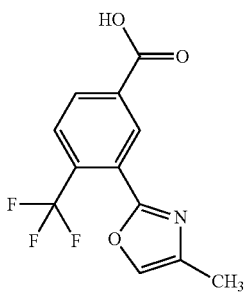 [SMILES: Cc1coc(-c2cc(C(=O)O)ccc2C(F)(F)F)n1]

3-(4-Methyloxazol-2-yl)-4-(trifluoromethyl)benzoic acid

A deoxygenated mixture of 3-bromo-4-(trifluoromethyl)benzoic acid (100 mg, 0.372 mmol), 4-methyloxazole (0.061 mL, 0.74 mmol), chloro(2-dicyclohexylphosphino-2',4',6'-tri-i-propyl-1,1'-biphenyl)[2-(2-aminoethyl)phenyl]palladium(II) methyl-t-butyl ether adduct (15.4 mg, 0.019 mmol), and sodium tert-butoxide (107 mg, 1.12 mmol) in DMA (1.5 mL) was heated under microwave irradiation at 110° C. for 18 h. The mixture was cooled and filtered, and the filtrate was purified by reverse-phase HPLC (C18 column, $H_2O$:$CH_3CN$:$CF_3CO_2H$=95:5:0.1 to 5:95:0.1) to give the title compound. MS: m/z=272.0 (M+1).

Intermediate B20

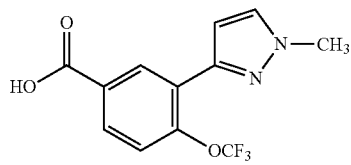 [SMILES: Cn1ccc(-c2cc(C(=O)O)ccc2OC(F)(F)F)n1]

3-(1-Methyl-1H-pyrazol-3-yl)-4-(trifluoromethoxy)benzoic acid

Step A: 3-Nitro-4-(trifluoromethoxy)benzoic acid 4-(Trifluoromethoxy)benzoic acid (37.4 g, 0.181 mol) was added portionwise to an aqueous $HNO_3$ solution (15 M, 75 mL) at 25° C. Aqueous $H_2SO_4$ solution (18 M, 90 mL) was added and the resulting mixture was stirred for 18 h. The reaction mixture was carefully diluted with water (300 mL) and the precipitate was filtered, washed with water, and dried to give the title compound. MS: m/z=252 (M+1). $^1$H NMR (400 MHz, DMSO-$d_6$) δ 8.54 (s, 1H), 8.32 (d, J=8.0 Hz, 1H), 7.82 (d, J=8.0 Hz, 1H).

Step B: Methyl 3-nitro-4-(trifluoromethoxy)benzoate

Aqueous $H_2SO_4$ solution (18 M, 60 mL) was added dropwise to a solution of 3-nitro-4-(trifluoromethoxy)benzoic acid (33.5 g, 0.135 mol) in MeOH (400 mL) at 0° C. The resulting mixture was heated at 80° C. for 2 h, then cooled and concentrated. The residue was diluted with EtOAc, and washed with water (100 mL×3), aqueous NaHCO$_3$ solution (100 mL×3), and brine. The organic layer was dried over Na$_2$SO$_4$ and concentrated to give the title compound. MS: m/z:266 (M+1). $^1$H NMR (400 MHz, DMSO-d$_6$) δ 8.54 (s, 1H), 8.32 (d, J=8.0 Hz, 1H), 7.82 (d, J=8.0 Hz, 1H), 3.90 (s, 3H).

Step C: Methyl 3-amino-4-(trifluoromethoxy)benzoate

A mixture of methyl 3-nitro-4-(trifluoromethoxy)benzoate (14 g, 0.053 mol) and 10% Pd/C (1.0 g, 10 wt %) in MeOH (200 mL) was stirred under H$_2$ (50 psi) at 15° C. for 24 h. The suspension was filtered and the filtrate was concentrated. The residue was purified by column chromatography on silica gel (PE:EtOAc=5:1) to give the title compound. MS: m/z=236 (M+1). $^1$H NMR (400 MHz, DMSO-d$_6$) δ 7.47 (d, J=2.0 Hz, 1H), 7.19-7.25 (m, 1H), 7.11-7.17 (m, 1H), 5.71 (s, 2H), 3.82 (s, 3H).

Step D: Methyl 3-bromo-4-(trifluoromethoxy)benzoate

A mixture of CuBr (5.0 g, 34 mmol) and t-BuONO (5.0 g, 43 mmol) in MeCN (60 mL) was stirred at 0° C. for 15 min, and then methyl 3-amino-4-(trifluoromethoxy)benzoate (4.0 g, 17 mmol) was added. The resulting mixture was stirred at 0° C. for 2 h, and then stirred at 15° C. for 16 h. The mixture was filtered and the filter cake was washed with EtOAc. The filtrate was washed with aqueous HCl solution (1N), water, and then brine. The organic layer was dried over Na$_2$SO$_4$ and concentrated. The residue was purified by column chromatography on silica gel (PE:EtOAc=20:1) to give the title compound. MS: m/z=298/300 (M+1). $^1$H NMR (400 MHz, DMSO-d$_6$) δ 8.14 (d, J=2.0 Hz, 1H), 7.96 (dd, J=8.7, 1.9 Hz, 1H), 7.55 (dd, J=8.7, 1.1 Hz, 1H), 3.84 (s, 3H).

Step E: Methyl 3-(1-(tetrahydro-2H-pyran-2-yl)-1H-pyrazol-5-yl)-4-(trifluoro-methoxy)benzoate A deoxygenated mixture of methyl 3-bromo-4-(trifluoromethoxy)benzoate (500 mg, 1.67 mmol), 1-(tetrahydro-2H-pyran-2-yl)-5-(4,4,5,5-tetramethyl-1,3,2-dioxaborolan-2-yl)-1H-pyrazole (510 mg, 1.84 mmol), Pd(PPh$_3$)$_4$ (50 mg, 0.05 mmol), and Na$_2$CO$_3$ (530 mg, 5.0 mmol) in DMF (5 mL) was heated at 100° C. under N$_2$ atmosphere for 16 h. The reaction mixture was cooled and then partitioned between water (15 mL) and EtOAc (15 mL×3). The combined organic layers were dried over Na$_2$SO$_4$ and concentrated. The residue was purified by preparative TLC (PE:EtOAc=3:1) to give the title compound. MS: m/z=371 (M+1).

Step F: Methyl 3-(1H-pyrazol-5-yl)-4-(trifluoromethoxy)benzoate

A solution of HCl in EtOAc (4 M, 10 mL, 40 mmol) was added to a solution of methyl 3-(1-(tetrahydro-2H-pyran-2-yl)-1H-pyrazol-5-yl)-4-(trifluoromethoxy)benzoate (300 mg, 1.1 mmol) in EtOAc (2 mL). The resulting mixture was stirred at 15° C. for 1 h and then concentrated to give the title compound. MS: m/z=287 (M+1).

Step G: Methyl 3-(1-methyl-1H-pyrazol-3-yl)-4-(trifluoromethoxy)benzoate

A mixture of methyl 3-(1H-pyrazol-5-yl)-4-(trifluoromethoxy)benzoate (220 mg, 0.81 mmol), CH$_3$I (0.292 mL, 4.00 mmol), and Cs$_2$CO$_3$ (780 mg, 2.4 mmol) in DMF (5 mL) was heated at 70° C. for 1 h. The mixture was cooled and then partitioned between water (10 mL) and EtOAc (10 mL×2). The combined organic layers were dried over Na$_2$SO$_4$ and concentrated. The residue was purified by preparative TLC (PE:EtOAc=2:1) to give the title compound. MS: m/z=301 (M+1).

Step H: 3-(1-Methyl-1H-pyrazol-3-yl)-4-(trifluoromethoxy)benzoic acid

A mixture of methyl 3-(1-methyl-1H-pyrazol-3-yl)-4-(trifluoromethoxy)benzoate (120 mg, 0.4 mmol) and aqueous NaOH solution (2 M, 10 mmol, 5 mL) was heated at 50° C. for 30 min. The reaction mixture was cooled, acidified to pH 5 with aqueous HCl solution (1 M), and then extracted with EtOAc (10 mL×2). The combined organic layers were dried over Na$_2$SO$_4$ and concentrated to give the title compound. MS: m/z=287 (M+1).

REACTION SCHEME FOR EXAMPLE 4

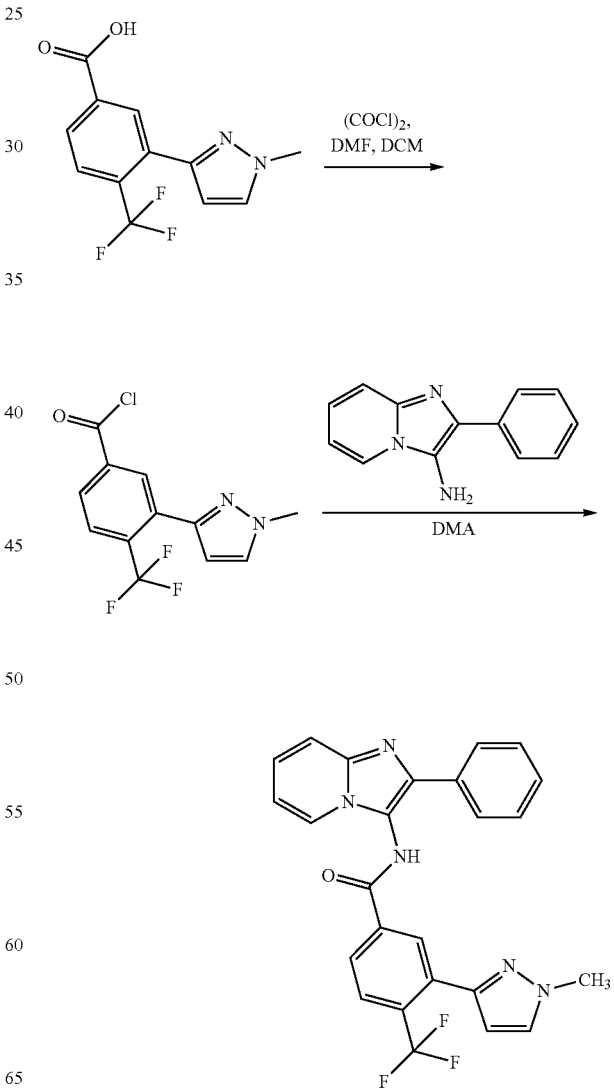

Example 4

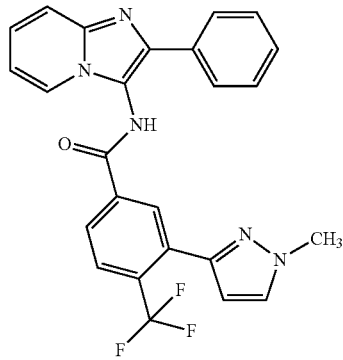 [SMILES: Cn1ccc(-c2cc(C(=O)Nc3c(-c4ccccc4)nc4ccccn34)ccc2C(F)(F)F)n1]

3-(1-Methyl-1H-pyrazol-3-yl)-N-(2-phenylimidazo[1,2-a]pyridin-3-yl)-4-(trifluoromethyl)benzamide (COCl)$_2$ (1.1 mL, 2.2 mmol) was added to a solution of 3-(1-methyl-1H-pyrazol-3-yl)-4-(trifluoromethyl)benzoic acid (0.50 g, 1.9 mmol) and DMF (0.014 mL, 0.19 mmol) in DCM (20 mL), and the resulting mixture was stirred at ambient temperature for 0.5 h. The mixture was concentrated and dried under vacuum. The residue was dissolved in DMA (4 mL) and 2-phenylimidazo[1,2-a]pyridin-3-amine (0.45 g, 2.1 mmol) was added. The resulting mixture was stirred at ambient temperature for 2 h and then concentrated. The residue was purified by column chromatography on silica gel (Hexanes:EtOAc=100:0 to 0:100) to give the title compound. MS: m/z=462.1 (M+1). $^1$H NMR (400 MHz, CDCl$_3$) δ 8.51 (s, 1H), 8.31 (s, 1H), 8.08 (d, J=8.1 Hz, 1H), 7.91-7.84 (m, 5H), 7.64 (d, J=9.1 Hz, 1H), 7.43-7.32 (m, 3H), 7.28-7.25 (m, 1H), 6.87-6.84 (m, 1H), 6.55 (s, 1H), 3.91 (s, 3H).

REACTION SCHEME FOR EXAMPLE 9

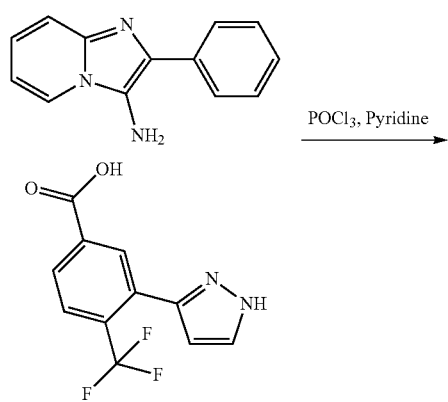 POCl$_3$, Pyridine

Example 9

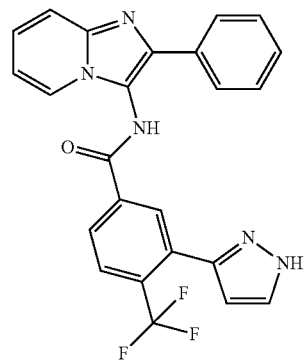 [SMILES: O=C(Nc1c(-c2ccccc2)nc2ccccn12)c1ccc(C(F)(F)F)c(-c2cc[nH]n2)c1]

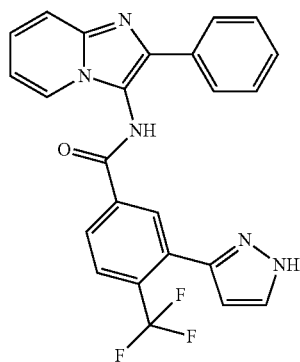

N-(2-Phenylimidazo[1,2-a]pyridin-3-yl)-3-(1H-pyrazol-3-yl)-4-(trifluoromethyl)benzamide POCl$_3$ (0.20 mL, 2.2 mmol) was added to a suspension of 2-phenylimidazo[1,2-a]pyridin-3-amine (0.23 g, 1.1 mmol) and 3-(1H-pyrazol-3-yl)-4-(trifluoromethyl)benzoic acid (0.28 g, 1.1 mmol) in pyridine (0.3 mL), and the resulting mixture was stirred at ambient temperature for 1.5 h. Water (0.3 mL) was added and stirring was continued for an additional 2 h. The product mixture was purified by reverse-phase HPLC (5-95% acetonitrile+0.1% trifluoroacetic acid in water) to provide the title compound as a trifluoroacetate salt. MS: m/z=448.0 (M+1). $^1$H NMR (400 MHz, DMSO) δ 11.10 (s, 1H), 8.42-8.32 (m, 2H), 8.23 (d, J=7.7 Hz, 1H), 8.06 (d, J=8.2 Hz, 1H), 7.93 (d, J=7.6 Hz, 2H), 7.83 (s, 1H), 7.78-7.70 (m, 1H), 7.58-7.32 (m, 4H), 7.15-7.08 (m, 1H), 6.53 (s, 1H).

Example 11

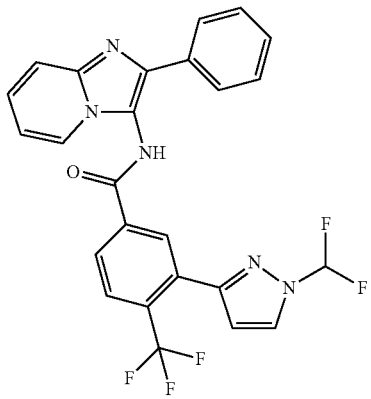 [SMILES: O=C(Nc1c(-c2ccccc2)nc2ccccn12)c1ccc(C(F)(F)F)c(-c2ccn(C(F)F)n2)c1]

3-(1-(Difluoromethyl)-1H-pyrazol-3-yl)-N-(2-phenylimidazo[1,2-a]pyridin-3-yl)-4-(trifluoromethyl)benzamide POCl$_3$ (0.019 mL, 0.201 mmol) was added to a suspension of 2-phenylimidazo[1,2-a]pyridin-3-amine (14 mg, 0.069 mmol) and 3-(1-(difluoromethyl)-1H-pyrazol-3-yl)-4-(trifluoromethyl)benzoic acid (21 mg, 0.069 mmol) in pyridine (0.3 mL), and the resulting mixture was stirred at ambient temperature for 72 h. The product mixture was diluted with DMF (1 mL) and purified by reverse-phase HPLC (5-95% acetonitrile+0.1% trifluoroacetic acid in water) to yield the title compound as a trifluoroacetate salt. MS: m/z=498.0 (M+1). $^1$H NMR (400 MHz, CDCl$_3$) δ 11.39 (s, 1H), 8.49-8.42 (m, 2H), 8.07 (d, J=6.8 Hz, 1H), 7.97 (d, J=8.2 Hz, 1H), 7.89 (d, J=2.7 Hz, 1H), 7.66-7.58 (m, 2H), 7.50 (d, J=8.6 Hz, 1H), 7.46-7.41 (m, 1H), 7.18-7.06 (m, 5H), 6.75 (d, J=2.1 Hz, 1H).

Example 12

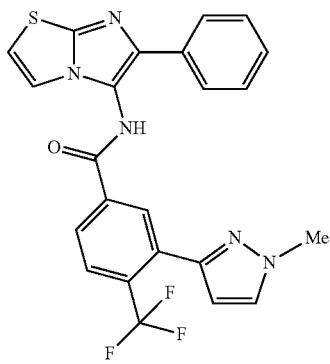 [SMILES: Cn1ccc(-c2cc(C(=O)Nc3c(-c4ccccc4)nc4sccn34)ccc2C(F)(F)F)n1]

3-(1-Methyl-1H-pyrazol-3-yl)-N-(6-phenylimidazo[2,1-b]thiazol-5-yl)-4-(trifluoromethyl)benzamide A solution of 3-(1-methyl-1H-pyrazol-3-yl)-4-(trifluoromethyl)benzoic acid (25 mg, 0.093 mmol), PYAOP (58 mg, 0.11 mmol), DIEA (0.049 mL, 0.28 mmol), and 6-phenylimidazo[2,1-b]thiazol-5-amine (20 mg, 0.093 mmol) in DMF (1 mL) was heated at 60° C. for 18 h. The product mixture was cooled and then purified by reverse-phase HPLC (5-95% acetonitrile+0.1% trifluoroacetic acid in water). The combined desired fractions were partitioned between aqueous NaOH solution (1 N, 10 mL) and DCM (3×10 mL). The combined organic layers were dried over Na$_2$SO$_4$ and concentrated to provide the title compound. MS: m/z=468.0 (M+1). $^1$H NMR (400 MHz, CDCl$_3$) δ 8.65 (s, 1H), 8.22 (s, 1H), 8.01 (d, J=8.2 Hz, 1H), 7.82-7.79 (m, 3H), 7.41-7.37 (m, 4H), 7.30 (t, J=7.3 Hz, 1H), 6.85 (d, J=4.5 Hz, 1H), 6.52 (s, 1H), 3.86 (s, 3H).

Example 14

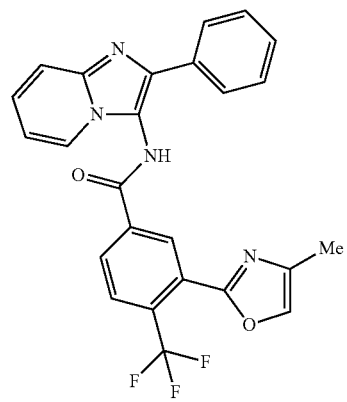 [SMILES: Cc1coc(-c2cc(C(=O)Nc3c(-c4ccccc4)nc4ccccn34)ccc2C(F)(F)F)n1]

3-(4-Methyloxazol-2-yl)-N-(2-phenylimidazo[1,2-a]pyridin-3-yl)-4-(trifluoromethyl)benzamide POCl$_3$ (1.5 µL, 0.016 mmol) was added to a suspension of 2-phenylimidazo[1,2-a]pyridin-3-amine (1.7 mg, 0.008 mmol) and 3-(4-methyloxazol-2-yl)-4-(trifluoromethyl)benzoic acid (2.2 mg, 0.008 mmol) in pyridine (0.1 mL), and the resulting mixture was stirred at ambient temperature for 18 h. The product mixture was diluted with DMF (1 mL) and purified by reverse-phase HPLC (5-95% acetonitrile+0.1% trifluoroacetic acid in water) to give the title compound as a trifluoroacetate salt. MS: m/z=463.0 (M+1). $^1$H NMR (400 MHz, CDCl$_3$) δ 11.19 (s, 1H), 8.82 (s, 1H), 8.45 (d, J=8.0 Hz, 1H), 8.19 (d, J=6.8 Hz, 1H), 8.00 (d, J=8.2 Hz, 1H), 7.65-7.60 (m, 3H), 7.58 (d, J=9.0 Hz, 1H), 7.49 (t, J=7.6 Hz, 1H), 7.20-7.08 (m, 4H), 2.30 (d, J=1.0 Hz, 3H).

Example 16

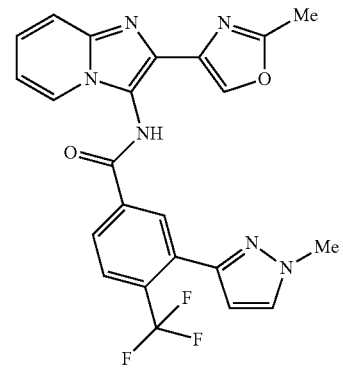 [SMILES: Cc1nc(-c2nc3ccccn3c2NC(=O)c2ccc(C(F)(F)F)c(-c3ccn(C)n3)c2)co1]

3-(1-Methyl-1H-pyrazol-3-yl)-N-(2-(2-methyloxazol-4-yl)imidazo[1,2-a]pyridin-3-yl)-4-(trifluoromethyl)benzamide A solution of 2-(2-methyloxazol-4-yl)imidazo[1,2-a]pyridin-3-amine (40 mg, 0.12 mmol), 3-(1-methyl-1H-pyrazol-3-yl)-4-(trifluoromethyl)benzoic acid (33 mg, 0.12 mmol), 7-azabenzotriazol-1-yloxytris(dimethylamino)phosphonium hexafluorophosphate (65 mg, 0.15 mmol), DMAP (1.5 mg, 0.012 mmol), and DIEA (0.064 mL, 0.37 mmol) in DMF (1.0 mL) was heated at 60° C. for 21 h. The product mixture was cooled and then purified by reverse-phase HPLC (5-95% acetonitrile+0.1% trifluoroacetic acid in water) to yield the title compound as a trifluoroacetate salt. MS: m/z=467 (M+1). $^1$H NMR (400 MHz, CDCl$_3$) δ 10.19 (s, 1H), 8.45 (s, 1H), 8.38 (s, 1H), 8.21 (t, J=7.2 Hz, 2H), 8.06 (d, J=9.0 Hz, 1H), 7.93 (d, J=8.2 Hz, 1H), 7.66 (t, J=8.1 Hz, 1H), 7.45 (d, J=2.3 Hz, 1H), 7.23 (t, J=6.9 Hz, 1H), 6.55 (d, J=1.2 Hz, 1H), 3.99 (s, 3H), 2.38 (s, 3H).

REACTION SCHEME FOR EXAMPLE 27

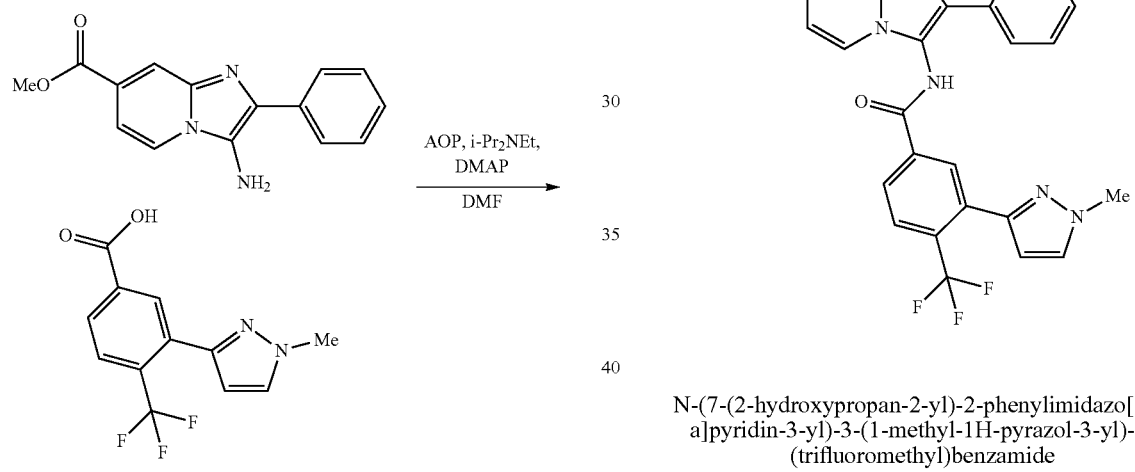

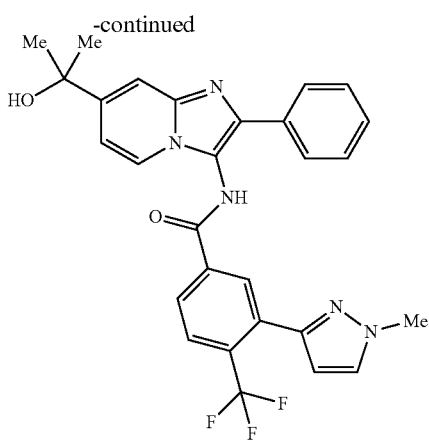

Example 27

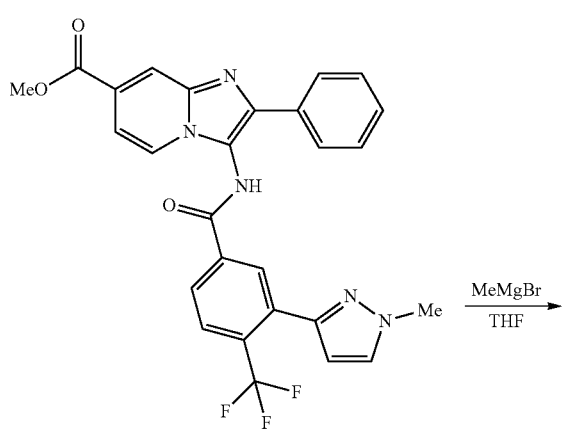

N-(7-(2-hydroxypropan-2-yl)-2-phenylimidazo[1,2-a]pyridin-3-yl)-3-(1-methyl-1H-pyrazol-3-yl)-4-(trifluoromethyl)benzamide Step A: Methyl 3-(3-(1-methyl-1H-pyrazol-3-yl)-4-(trifluoromethyl)benzamido)-2-phenylimidazo[1,2-a]pyridine-7-carboxylate Methyl 3-amino-2-phenylimidazo[1,2-a]pyridine-7-carboxylate (400 mg, 1.50 mmol) and 3-(1-methyl-1H-pyrazol-3-yl)-4-(trifluoromethyl)benzoic acid (404 mg, 1.50 mmol) were dissolved in DMF (3.3 mL). AOP (1.33 g, 2.99 mmol), diisopropylethylamine (0.78 mL, 4.49 mmol), and DMAP (18.3 mg, 0.15 mmol) were added, and the mixture was stirred at 30° C. for 16 h. The mixture was extracted with EtOAc (2×20 mL). The combined organic layers were washed with water (20 mL), dried over MgSO$_4$, and concentrated. The crude product was purified by SiO$_2$ flash column chromatography, eluting with 0-10% MeOH/EtOAc to give the title compound. MS: m/z=520.5 (M+1).

Step B: N-(7-(2-Hydroxypropan-2-yl)-2-phenylimidazo[1,2-a]pyridin-3-yl)-3-(1-methyl-1H-pyrazol-3-yl)-4-(trifluoromethyl)benzamide To a solution of methyl 3-(3-(1-methyl-1H-pyrazol-3-yl)-4-(trifluoromethyl)benzamido)-2-phenylimidazo[1,2-a]

pyridine-7-carboxylate (25 mg, 0.048 mmol) in tetrahydrofuran (0.96 mL) at room temperature under a N₂ atmosphere was added a 3.0 M solution of methylmagnesium bromide in Et₂O (64.2 µL, 0.193 mmol), and the mixture was stirred at 0° C. for 1 h. The reaction was quenched with ice (2 mL), and extracted with EtOAc (2×5 mL). Combined organic layers were washed with saturated aqueous NH₄Cl solution (5 mL), dried, and concentrated. The crude product was purified by SiO₂ flash column chromatography, eluting with 0-10% MeOH/EtOAc to give the title compound. MS: m/z=520.4 (M+1). $^1$H NMR (400 MHz, CD₃OD): δ 8.33 (s, 1H), 8.23 (d, J=8.0 Hz, 1H), 8.09 (d, J=7.2 Hz, 1H), 8.01 (d, J=8.3 Hz, 1H), 7.88-7.90 (m, 2H), 7.67-7.70 (m, 2H), 7.44 (t, J=7.6 Hz, 2H), 7.35 (t, J=7.5 Hz, 1H), 7.16 (dd, J=7.2, 1.8 Hz, 1H), 6.53 (s, 1H), 3.98 (s, 3H), 1.29 (s, 6H).

REACTION SCHEME FOR EXAMPLE 42

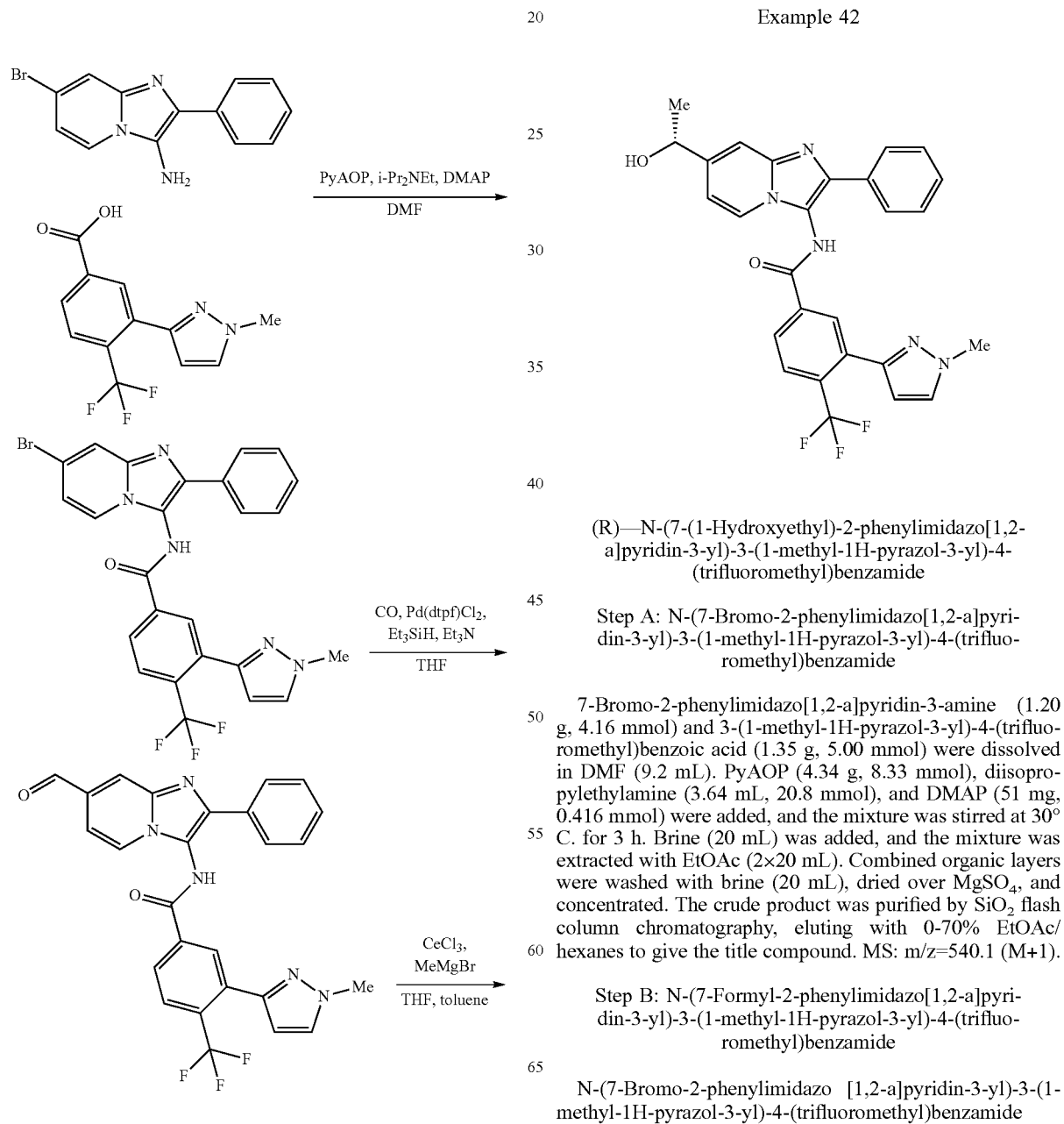

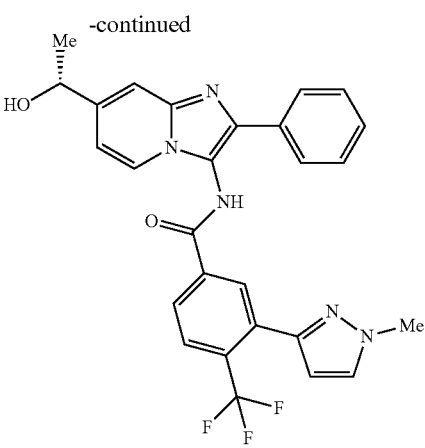

Example 42

(R)—N-(7-(1-Hydroxyethyl)-2-phenylimidazo[1,2-a]pyridin-3-yl)-3-(1-methyl-1H-pyrazol-3-yl)-4-(trifluoromethyl)benzamide Step A: N-(7-Bromo-2-phenylimidazo[1,2-a]pyridin-3-yl)-3-(1-methyl-1H-pyrazol-3-yl)-4-(trifluoromethyl)benzamide 7-Bromo-2-phenylimidazo[1,2-a]pyridin-3-amine (1.20 g, 4.16 mmol) and 3-(1-methyl-1H-pyrazol-3-yl)-4-(trifluoromethyl)benzoic acid (1.35 g, 5.00 mmol) were dissolved in DMF (9.2 mL). PyAOP (4.34 g, 8.33 mmol), diisopropylethylamine (3.64 mL, 20.8 mmol), and DMAP (51 mg, 0.416 mmol) were added, and the mixture was stirred at 30° C. for 3 h. Brine (20 mL) was added, and the mixture was extracted with EtOAc (2×20 mL). Combined organic layers were washed with brine (20 mL), dried over MgSO₄, and concentrated. The crude product was purified by SiO₂ flash column chromatography, eluting with 0-70% EtOAc/hexanes to give the title compound. MS: m/z=540.1 (M+1).

Step B: N-(7-Formyl-2-phenylimidazo[1,2-a]pyridin-3-yl)-3-(1-methyl-1H-pyrazol-3-yl)-4-(trifluoromethyl)benzamide N-(7-Bromo-2-phenylimidazo [1,2-a]pyridin-3-yl)-3-(1-methyl-1H-pyrazol-3-yl)-4-(trifluoromethyl)benzamide (550 mg, 1.02 mmol), Pd(dtpf)Cl$_2$ (66.3 mg, 0.102 mmol), triethylsilane (325 μL, 2.04 mmol), and triethylamine (142 μL, 1.02 mmol) were dissolved in THF (22.6 mL), and the solution was distributed across three 20-mL capacity vessels, which were placed under a 3-bar atmosphere of CO gas at 90° C. for 18 h. The contents of the vessels were then combined, water (20 mL) was added, and the mixture was extracted with EtOAc (2×30 mL). Combined organic layers were washed with brine (30 mL), dried over MgSO$_4$, and concentrated. The crude material was purified by SiO$_2$ flash column chromatography, eluting with 0-70% EtOAc/hexanes to give the title compound. MS: m/z=490.2 (M+1).

Step C: (R)—N-(7-(1-Hydroxyethyl)-2-phenylimidazo[1,2-a]pyridin-3-yl)-3-(1-methyl-1H-pyrazol-3-yl)-4-(trifluoromethyl)benzamide A suspension of CeCl$_3$ (10.1 mg, 0.041 mmol) in THF (817 μL) was cooled to 0° C. and treated with a 1.4 M solution (THF/toluene) of methylmagnesium bromide (117 μL, 0.163 mmol). After 1 h, a suspension of N-(7-formyl-2-phenylimidazo[1,2-a]pyridin-3-yl)-3-(1-methyl-1H-pyrazol-3-yl)-4-(trifluoromethyl)benzamide in toluene (817 μL) was added, and the mixture was allowed to warm to room temperature. After an additional 1 h, the reaction was cooled to 0° C. and quenched with a solution of saturated aqueous NH$_4$Cl. The mixture was diluted with water (2 mL) and extracted EtOAc (2×5 mL). Combined organic layers were washed with brine (5 mL), dried over MgSO$_4$, filtered, concentrated. The crude material was purified by SiO$_2$ flash column chromatography, eluting with 0-100% EtOAc/hexanes to give the purified racemate. The racemate was purified by SFC (AD-H column), eluting with 20% EtOH (0.1% NH$_4$OH)/CO$_2$ at 100 bar to give the title compound as the second-eluting enantiomer. MS: m/z=506.2 (M+1). $^1$H NMR (400 MHz, CD$_3$OD): δ 8.33 (s, 1H), 8.23 (d, J=8.3 Hz, 1H), 8.11 (d, J=7.1 Hz, 1H), 8.01 (d, J=8.3 Hz, 1H), 7.89 (d, J=7.7 Hz, 2H), 7.69 (d, J=2.3 Hz, 1H), 7.61 (s, 1H), 7.44 (t, J=7.6 Hz, 2H), 7.36 (t, J=7.4 Hz, 1H), 7.07 (dd, J=7.1, 1.6 Hz, 1H), 6.53 (s, 1H), 4.93 (q, J=6.6 Hz, 1H), 3.98 (s, 3H), 1.51 (d, J=6.6 Hz, 3H).

REACTION SCHEME FOR EXAMPLE 50

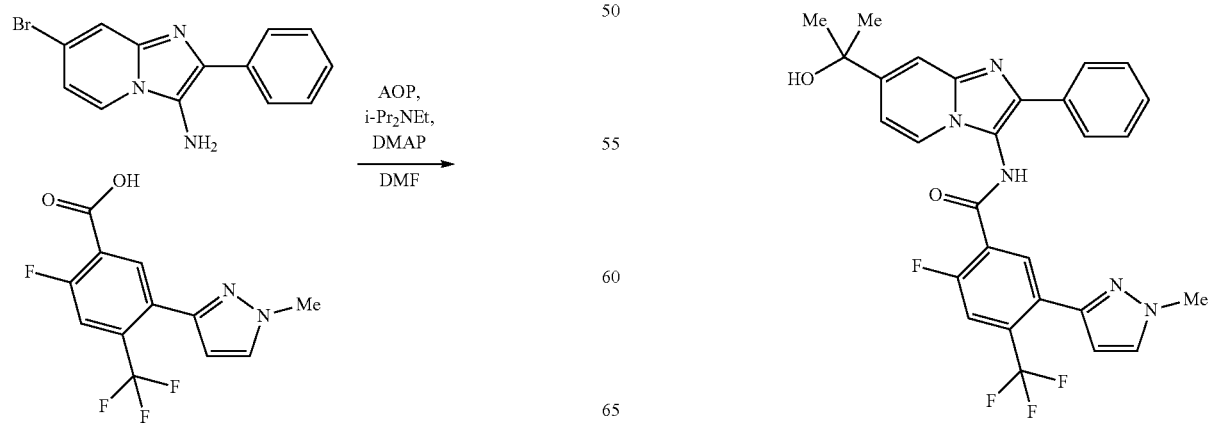

Example 50

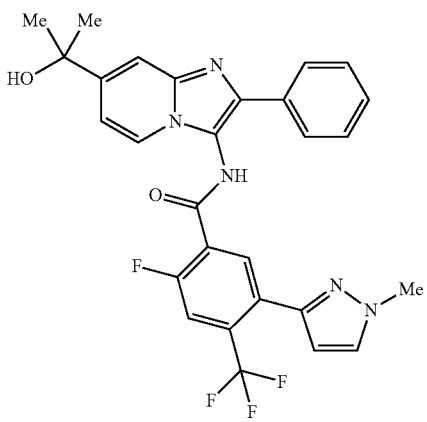 [SMILES: Cn1ccc(-c2cc(C(=O)Nc3c(-c4ccccc4)nc4cc(C(C)(C)O)ccn34)c(F)cc2C(F)(F)F)n1]

Step A: N-(7-bromo-2-phenylimidazo[1,2-a]pyridin-3-yl)-2-fluoro-5-(1-methyl-1H-pyrazol-3-yl)-4-(trifluoromethyl)benzamide 7-bromo-2-phenylimidazo[1,2-a]pyridin-3-amine (900 mg, 2.50 mmol) and 2-fluoro-5-(1-methyl-1H-pyrazol-3-yl)-4-(trifluoromethyl)benzoic acid (720 mg, 2.50 mmol) were suspended in DMF (6.25 mL). Diisopropylethylamine (2.18 mL, 12.5 mmol) and DMAP (30.5 mg, 0.25 mmol) were added, followed by AOP (3.88 g, 8.75 mmol), and the mixture was stirred at room temperature for 3 days. The mixture was then poured into brine (100 mL) and extracted with EtOAc (3×100 mL). Combined organic layers were washed with brine, dried over MgSO₄, filtered, and concentrated. The crude material was purified by SiO₂ gel flash column chromatography, eluting with 0-40% EtOAc/hexanes to give the title compound. MS: m/z=558.3 (M+1).

Step B: N-(7-Acetyl-2-phenylimidazo[1,2-a]pyridin-3-yl)-2-fluoro-5-(1-methyl-1H-pyrazol-3-yl)-4-(trifluoromethyl)benzamide DMF (8 mL) and H₂O (1 mL) were placed in a flask and sparged with N₂ gas for 45 min. A 20-mL vessel was charged with palladium acetate (11.6 mg, 0.052 mmol), potassium carbonate (171 mg, 1.24 mmol), and 1,3-bis(diphenylphosphino)propane (46.8 mg, 0.113 mmol). 1-(vinyloxy)butane (334 μL, 2.58 mmol) was added, followed by N-(7-bromo-2-phenylimidazo[1,2-a]pyridin-3-yl)-2-fluoro-5-(1-methyl-1H-pyrazol-3-yl)-4-(trifluoromethyl)benzamide (576 mg, 1.03 mmol). The DMF/H₂O (8:1) mixture (2.95 mL) was added to the reaction, and the vial was sealed. The vessel was evacuated and then purged with N₂ gas (5×), then heated at 80° C. for 16 h. The reaction was concentrated to dryness under a stream of N₂ gas. The crude material was purified by SiO₂ flash column chromatography, eluting with 0-80% EtOAc/hexanes to give 146 mg of the title compound and 243 mg of an enol ether intermediate. The enol ether was dissolved in MeOH (2.8 mL) and CH₂Cl₂ (2.8 mL), treated with 1 N aq. HCl, and allowed to stir for 22 h. Solvent was removed under a stream of N₂ gas, and the residue was neutralized with saturated aqueous NaHCO₃ (5 mL). The mixture was extracted with EtOAc (3×5 mL), and combined organic layers were dried over MgSO₄, filtered, and concentrated to give an additional 215 mg of the title compound. MS: m/z=522.4 (M+1).

Step C: 2-fluoro-N-(7-(2-hydroxypropan-2-yl)-2-phenylimidazo[1,2-a]pyridin-3-yl)-5-(1-methyl-1H-pyrazol-3-yl)-4-(trifluoromethyl)benzamide A suspension of CeCl₃ (3.54 mg, 0.014 mmol) in THF (0.29 mL) was cooled at 0° C. and treated with a 3 M solution (Et₂O) solution of methylmagnesium bromide (33.6 μL, 0.101 mmol). After 1 h, a solution of N-(7-acetyl-2-phenylimidazo[1,2-a]pyridin-3-yl)-2-fluoro-5-(1-methyl-1H-pyrazol-3-yl)-4-(trifluoromethyl)benzamide (15 mg, 0.029 mmol) in 1:1 THF/toluene (2.0 mL) was added. The reaction was allowed to warm to room temperature and stirred for 3 h, then cooled to 0° C. and quenched with a solution of saturated aqueous NH₄Cl (2 mL). The mixture was diluted with H₂O (2 mL) and extracted with EtOAc (2×5 mL). The combined organic layers were washed with brine, dried over MgSO₄, filtered, concentrated to give the title compound. MS: m/z=538.1 (M+1). ¹H NMR (400 MHz, CD₃OD): δ 8.11 (dd, J=15.0, 7.1 Hz, 2H), 7.94 (d, J=7.7 Hz, 2H), 7.82 (d, J=10.5 Hz, 1H), 7.67-7.70 (m, 2H), 7.47 (t, J=7.6 Hz, 2H), 7.37 (t, J=7.3 Hz, 1H), 7.19 (d, J=7.3 Hz, 1H), 6.51 (s, 1H), 3.98 (s, 3H), 1.61 (s, 6H).

Example 53

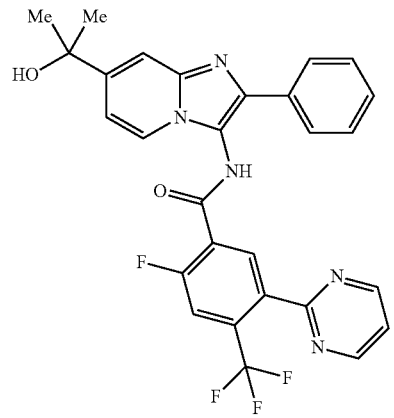 [SMILES: CC(C)(O)c1ccn2c(NC(=O)c3cc(-c4ncccn4)c(C(F)(F)F)cc3F)c(-c3ccccc3)nc2c1]

2-Fluoro-N-(7-(2-hydroxypropan-2-yl)-2-phenylimidazo[1,2-a]pyridin-3-yl)-5-(pyrimidin-2-yl)-4-(trifluoromethyl)benzamide

Step A: N-(7-Bromo-2-phenylimidazo[1,2-a]pyridin-3-yl)-2-fluoro-5-(pyrimidin-2-yl)-4-(trifluoromethyl)benzamide To a solution of 7-bromo-2-phenylimidazo[1,2-a]pyridin-3-amine (0.15 g, 0.52 mmol) and 2-fluoro-5-(pyrimidin-2-yl)-4-(trifluoromethyl)benzoic acid (0.15 g, 0.52 mmol) in DMF (1.1 mL) was added AOP (7-azabenzotriazol-1-yloxytris(dimethylamino)phosphonium hexafluorophosphate) (0.46 g, 1.0 mmol), DMAP (6.0 mg, 0.052 mmol) and DIEA (0.45 mL, 2.6 mmol). The resulting mixture was stirred at ambient temperature for 12 h and then partitioned between EtOAc and brine. The organic layer was dried over magnesium sulfate and concentrated. The residue was purified by column chromatography on silica gel (0 to 50% EtOAc in hexanes) to afford the title compound. MS: m/z=558.0 (M+1).

Step B: N-(7-(1-Ethoxyvinyl)-2-phenylimidazo[1,2-a]pyridin-3-yl)-2-fluoro-5-(pyrimidin-2-yl)-4-(trifluoromethyl)benzamide Bis(tri-t-butylphosphine)palladium (39 mg, 0.076 mmol) and tributyl(1-ethoxyvinyl)tin (0.26 mL, 0.76 mmol) were added to a solution of N-(7-bromo-2-phenylimidazo[1,2-a]pyridin-3-yl)-2-fluoro-5-(pyrimidin-2-yl)-4-(trifluoromethyl)benzamide (0.21 g, 0.379 mmol) in dioxane (1.9 mL). The resulting mixture was heated at 80° C. for 1 h, then cooled and partitioned between EtOAc and water. The organic layer was washed with brine, dried over magnesium sulfate, and concentrated afford the title compound. MS: m/z=548.0 (M+1).

Step C: N-(7-Acetyl-2-phenylimidazo[1,2-a]pyridin-3-yl)-2-fluoro-5-(pyrimidin-2-yl)-4-(trifluoromethyl)benzamide An aqueous HCl solution (1 N, 1.9 mL, 1.9 mmol) was added to a solution of N-(7-(1-ethoxyvinyl)-2-phenylimidazo[1,2-a]pyridin-3-yl)-2-fluoro-5-(pyrimidin-2-yl)-4-(trifluoromethyl)benzamide (0.21 g, 0.38 mmol) in MeOH (2.5 mL), and the resulting mixture was stirred at ambient temperature for 12 h. The mixture was concentrated and the residue was partitioned between a saturated aqueous sodium bicarbonate solution and EtOAc. The organic layer was washed with brine, dried over magnesium sulfate, and concentrated. The residue was purified by column chromatography on silica gel (0 to 100% EtOAc in hexanes) to afford the title compound as a yellow solid. MS: m/z=520.0 (M+1).

Step D: 2-Fluoro-N-(7-(2-hydroxypropan-2-yl)-2-phenylimidazo[1,2-a]pyridin-3-yl)-5-(pyrimidin-2-yl)-4-(trifluoromethyl)benzamide A solution of methylmagnesium bromide in diethyl ether (3.0 M, 0.15 mL, 0.45 mmol) was added to a suspension of ultra-dry cerium chloride (0.016 g, 0.064 mmol) in THF (1.3 mL) at 0° C. The resulting mixture was stirred at 0° C. for 1 h before a solution of N-(7-acetyl-2-phenylimidazo[1,2-a]pyridin-3-yl)-2-fluoro-5-(pyrimidin-2-yl)-4-(trifluoromethyl)benzamide (0.067 g, 0.13 mmol) in 1:1 toluene/THF (2 mL) was added dropwise. The mixture was warmed to ambient temperature and stirred for 3 h. The mixture was then cooled to 0° C., and excess MeMgBr was quenched with aqueous ammonium chloride solution. The mixture was partitioned between water and EtOAc. The organic layer was washed with brine, dried over magnesium sulfate, and concentrated to afford the title compound. MS: m/z=536.0 (M+1). $^1$H NMR (400 MHz, CD$_3$OD) δ 8.95-8.93 (d, J=8.0 Hz, 1H) 8.30-8.28 (d, J=8.0 Hz, 1H) 8.11-8.09 (d, J=7.2 Hz, 1H) 7.95-7.88 (m, 3H) 7.71 (s, 1H) 7.56-7.35 (m, 5H) 7.19-7.17 (d, J=8.0 Hz, 1H) 1.60 (s, 6H).

Example 54

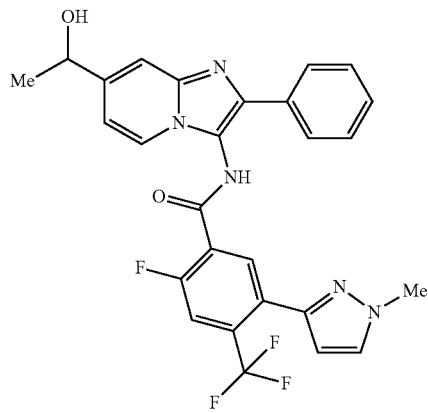 [SMILES: CC(O)c1ccn2c(NC(=O)c3cc(-c4ccn(C)n4)c(C(F)(F)F)cc3F)c(-c3ccccc3)nc2c1]

2-(R or S)-Fluoro-N-(7-(1-hydroxyethyl)-2-phenylimidazo[1,2-a]pyridin-3-yl)-5-(1-methyl-1H-pyrazol-3-yl)-4-(trifluoromethyl)benzamide

Step A: N-(7-Bromo-2-phenylimidazo[1,2-a]pyridin-3-yl)-2-fluoro-5-(1-methyl-1H-pyrazol-3-yl)-4-(trifluoromethyl)benzamide To a solution of 7-bromo-2-phenylimidazo[1,2-a]pyridin-3-amine (0.10 g, 0.35 mmol) and 2-fluoro-5-(1-methyl-1H-pyrazol-3-yl)-4-(trifluoromethyl)benzoic acid (0.10 g, 0.35 mmol) in DMF (0.76 mL) was added AOP (7-azabenzotriazol-1-yloxytris (dimethylamino)phosphoniumhexafluorophosphate) (0.30 g, 0.69 mmol), DMAP (4.0 mg, 0.035 mmol) and DIEA (0.30 mL, 1.7 mmol). The resulting mixture was stirred at ambient temperature for 12 h and then partitioned between EtOAc and brine. The organic layer was dried over magnesium sulfate and concentrated. The residue was purified by column chromatography on silica gel (0 to 40% EtOAc in hexanes) to afford the title compound. MS: m/z=560.0 (M+1).

Step B: N-(7-(1-Ethoxyvinyl)-2-phenylimidazo[1,2-a]pyridin-3-yl)-2-fluoro-5-(1-methyl-1H-pyrazol-3-yl)-4-(trifluoromethyl)benzamide To a deoxygenated solution of N-(7-bromo-2-phenylimidazo[1,2-a]pyridin-3-yl)-2-fluoro-5-(1-methyl-1H-pyrazol-3-yl)-4-(trifluoromethyl)benzamide (0.14 g, 0.25 mmol) in dioxane (1.2 mL) was added bis(tri-t-butylphosphine)palladium (25 mg, 0.049 mmol) followed by tributyl(1-ethoxyvinyl)tin (0.17 mL, 0.49 mmol). The resulting mixture was heated at 80° C. for 1 h, then cooled and partitioned between EtOAc and water. The organic layer was washed with brine, dried over magnesium sulfate, and concentrated to afford the title compound. MS: m/z=530.0 (M+1).

Step C: N-(7-Acetyl-2-phenylimidazo[1,2-a]pyridin-3-yl)-2-fluoro-5-(1-methyl-1H-pyrazol-3-yl)-4-(trifluoromethyl)benzamide To a solution of N-(7-(1-ethoxyvinyl)-2-phenylimidazo[1,2-a]pyridin-3-yl)-2-fluoro-5-(1-methyl-1H-pyrazol-3-yl)-4-(trifluoromethyl)benzamide (0.13 g, 0.25 mmol) in MeOH (1.6 mL) was added aqueous HCl solution (1 N, 1.2 mL, 1.2 mmol), and the resulting mixture was stirred at ambient temperature for 12 h. The mixture was concentrated and residue was partitioned between a saturated aqueous sodium bicarbonate solution and EtOAc. The organic layer was washed with brine, dried over magnesium sulfate, and concentrated. The residue was purified by column chromatography on silica gel (0 to 100% EtOAc in hexanes) to afford the title compound. MS: m/z=522.0 (M+1).

Step D: 2-(R or S)-Fluoro-N-(7-(1-hydroxyethyl)-2-phenylimidazo[1,2-a]pyridin-3-yl)-5-(1-methyl-1H-pyrazol-3-yl)-4-(trifluoromethyl)benzamide Sodium borohydride (0.020 g, 0.038 mmol) was added to a solution of N-(7-acetyl-2-phenylimidazo[1,2-a]pyridin-3-yl)-2-fluoro-5-(1-methyl-1H-pyrazol-3-yl)-4-(trifluoromethyl)benzamide (0.020 g, 0.038 mmol) in EtOH (1 mL) at 0° C. and the resulting mixture was stirred at 0° C. for 0.5 h. The mixture was concentrated and the residue was partitioned between water and EtOAc. The organic layer was dried over magnesium sulfate and concentrated to afford the mixture of enantiomers. The enantiomers were separated using supercritical fluid chromatography (SFC) (2 cm×25 cm IC column) eluting with 25% MeOH (0.1% DEA), 75% CO$_2$ at 50 mL/min to afford the title compound. MS: m/z=524.0 (M+1). $^1$H NMR (400 MHz, CD$_3$OD) δ 8.13-8.10 (m, 2H) 7.95-7.93 (d, J=8.0 Hz, 1H) 7.83-7.80 (d, J=8.0 Hz, 1H) 7.68 (s, 1H) 7.60 (s, 1H) 7.48-7.44 (m, 2H) 7.39-7.37 (m, 2H) 7.09-7.07 (d, J=8.0 Hz, 1H) 6.50 (s, 1H) 4.95-4.90 (q, J=6.8 Hz, 1H) 3.97 (s, 3H) 1.52-1.50 (d, J=6.8 Hz, 3H).

Example 85

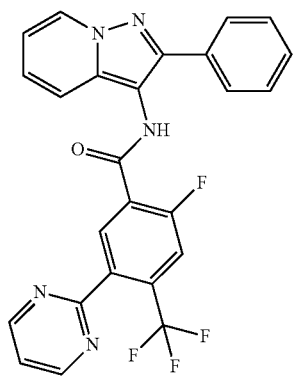 [SMILES: O=C(Nc1c(-c2ccccc2)nn2ccccc12)c1cc(-c2ncccn2)c(C(F)(F)F)cc1F]

Example 86

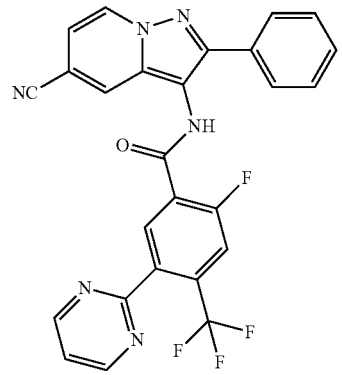 [SMILES: N#Cc1ccn2nc(-c3ccccc3)c(NC(=O)c3cc(-c4ncccn4)c(C(F)(F)F)cc3F)c2c1]

Example 91

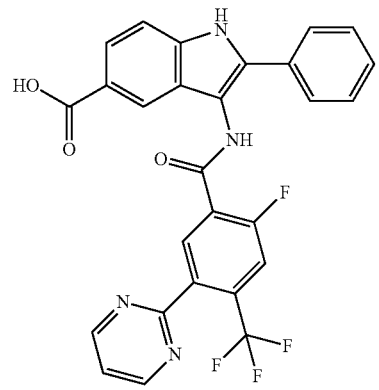 [SMILES: O=C(O)c1ccc2[nH]c(-c3ccccc3)c(NC(=O)c3cc(-c4ncccn4)c(C(F)(F)F)cc3F)c2c1]

Example 92

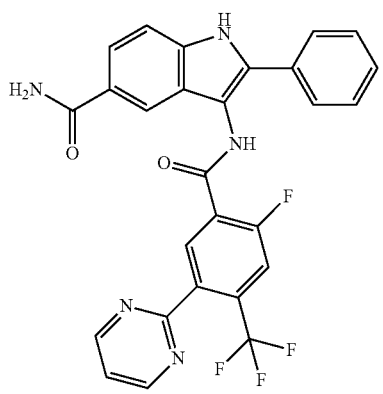 [SMILES: NC(=O)c1ccc2[nH]c(-c3ccccc3)c(NC(=O)c3cc(-c4ncccn4)c(C(F)(F)F)cc3F)c2c1]

Example 93 and 94

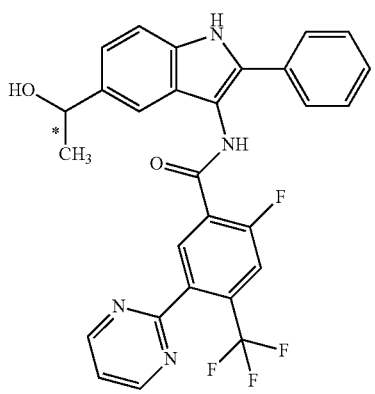 [SMILES: CC(O)c1ccc2[nH]c(-c3ccccc3)c(NC(=O)c3cc(-c4ncccn4)c(C(F)(F)F)cc3F)c2c1]

Example 96

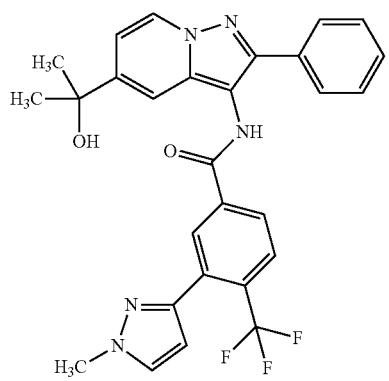 [SMILES: Cn1ccc(-c2cc(C(=O)Nc3c(-c4ccccc4)nn4ccc(C(C)(C)O)cc34)ccc2C(F)(F)F)n1]

Example 97 and 98

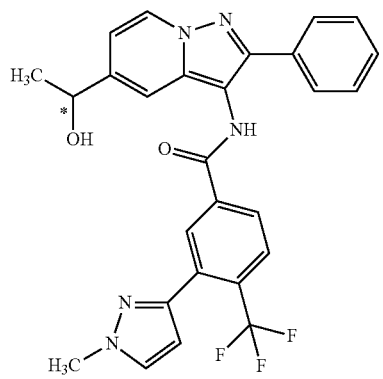 [SMILES: CC(O)c1ccn2nc(-c3ccccc3)c(NC(=O)c3ccc(C(F)(F)F)c(-c4ccn(C)n4)c3)c2c1]

REACTION SCHEME FOR EXAMPLE 104

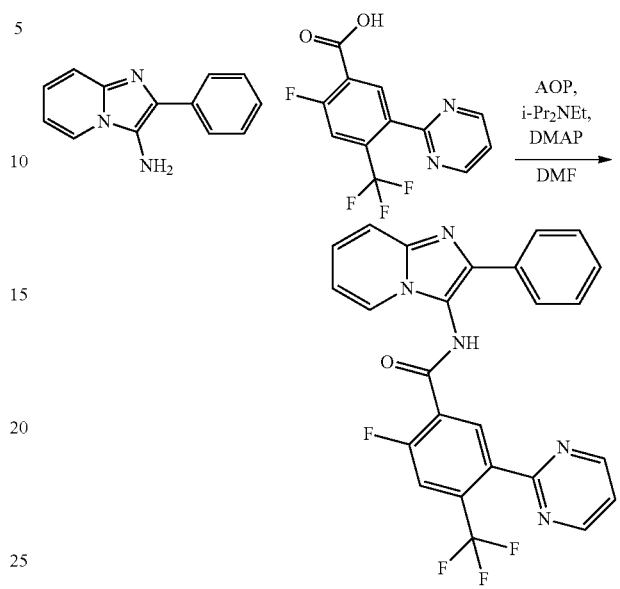

Example 104

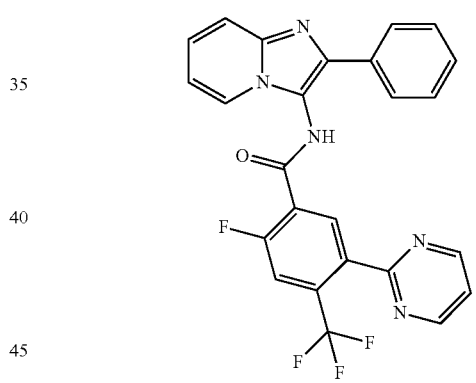

2-fluoro-N-(2-phenylimidazo[1,2-a]pyridin-3-yl)-5-(pyrimidin-2-yl)-4-(trifluoromethyl)benzamide To 2-phenylimidazo[1,2-a]pyridin-3-amine (100 mg, 0.478 mmol) and 2-fluoro-5-(pyrimidin-2-yl)-4-(trifluoromethyl)benzoic acid (137 mg, 0.478 mmol) in pyridine (2.4 mL) at 0° C. was added phosphoryl trichloride in a dropwise manner (53.5 μL, 0.573 mmol). The mixture was maintained at 0° C. with stirring for 20 min. The reaction was carefully quenched with saturated aqueous NaHCO₃ solution (3 mL), and the resulting mixture was partitioned between brine (5 mL) and 3:1 EtOAc/hexane (10 mL). The organic layer was dried over MgSO₄, filtered, and concentrated. The crude material was purified by SiO₂ column chromatography, eluting with 0-70% EtOAc/hexanes to give the title compound. MS: m/z=478.3 (M+1). $^1$H NMR (500 MHz, CDCl₃): δ 8.92 (m, 2H), 7.97 (d, J=7.5 Hz, 2H), 7.87 (s, 1H), 7.76 (d, J=11.3 Hz, 1H), 7.71 (d, J=8.7 Hz, 1H), 7.48 (m, 2H), 7.40 (m, 2H), 7.30 (m, 2H), 6.92 (m, 1H).

Biological Utility

TrkA functional activity was measured using a DiscoverX PathHunter assay. In this assay, U2OS cells express the human TrkA receptor as a fusion with the weakly complementing fragment of B-galactosidase, which DiscoverX calls "Prolink (PK)"; additionally, Shc1 is fused with a larger fragment, which is called "Enzyme Acceptor (EA)". Activation of the TrkA receptor, upon NGF addition, results in the kinase domain being phosphorylated, resulting in subsequent recruitment of Shc1-EA protein. That recruitment results in an active B-galactosidase enzyme that is detected by addition of a chemiluminescent substrate. The human p75$^{NTR}$ protein was also expressed as a co-receptor for NGF.

All reagents were purchased from DiscoverX, except for the receptor agonists (NGF, BDNF, NT3) which were purchased from Peprotech. Cells were expanded and frozen into cryovials, and stored in the vapor phase of liquid nitrogen, and thawed immediately before use. Thawed cells were added to a 384-well plate at 7500 cells/well, and allowed to incubate overnight. Compound at various concentrations was added the following morning and allowed to incubate on cells for 1 h. Then, NGF was added at a concentration sufficient to elicit ~80% of a maximal response and allowed to incubate for 3 h at ambient temperature. DiscoverX PathHunter detection reagent was then added and the plate was further incubated for 1 h in the dark. The plate was then read via luminescence on the Perkin Elmer Envision.

The percent inhibition was calculated for each compound concentration, and the $IC_{50}$ was determined using Equation 1 below.

$$\% \text{ Inhibition} = \left( \text{Max} + \frac{(\text{Max} - \text{Min})}{1 + \left(\frac{Conc}{IC_{50}}\right)^{Hill}} \right) \quad \text{Equation 1}$$

$IC_{50}$ values from the aforementioned assay for the compounds of this invention range between 20 nM to 10000 nM. $IC_{50}$ values for particular compounds of this invention are provided below in Table 2 below:

TABLE 2

| L-Number | Compound # | IUPAC Name | $IC_{50}$ (nM) |
|---|---|---|---|
| L-005152633-000R | 1 | N-(2-phenylimidazo[1,2-a]pyridin-3-yl)-4-(trifluoromethoxy)benzamide | 550 |
| L-005164982-001D | 2 | 2-fluoro-N-(6-phenylimidazo[2,1-b][1,3]thiazol-5-yl)-4-(trifluoromethyl)benzamide | 139 |
| L-005214502-002K | 3 | 3-(1-methyl-1H-pyrazol-3-yl)-N-(2-phenylimidazo[1,2-a]pyrimidin-3-yl)-4-(trifluoromethyl)benzamide | 5.9 |
| L-005215108-000N | 4 | 3-(1-methyl-1H-pyrazol-3-yl)-N-(2-phenylimidazo[1,2-a]pyridin-3-yl)-4-(trifluoromethyl)benzamide | 1.4 |
| L-005220405-002M | 5 | 3-(1-methyl-1H-pyrazol-3-yl)-N-(2-pyridin-2-ylimidazo[1,2-a]pyridin-3-yl)-4-(trifluoromethyl)benzamide | 12 |
| L-005221437-000X | 6 | 3-(1-methyl-1H-pyrazol-3-yl)-N-(2-phenylimidazo[1,2-b]pyridazin-3-yl)-4-(trifluoromethyl)benzamide | 3.9 |
| L-005231335-000J | 7 | 2-fluoro-N-[5-(1-methylethyl)-2-phenylimidazo[1,2-a]pyridin-3-yl]-4-(trifluoromethyl)benzamide | 264 |
| L-005235311-000T | 8 | 3-(1-methyl-1H-pyrazol-3-yl)-N-(2-pyrimidin-4-ylimidazo[1,2-a]pyridin-3-yl)-4-(trifluoromethyl)benzamide | 568 |
| L-005269032-001E | 9 | N-(2-phenylimidazo[1,2-a]pyridin-3-yl)-3-(1H-pyrazol-3-yl)-4-(trifluoromethyl)benzamide | 8.8 |
| L-005288517-001W | 10 | 2-fluoro-N-(2-isoxazol-5-ylimidazo[1,2-a]pyridin-3-yl)-4-(trifluoromethyl)benzamide | 1920 |
| L-005288524-001M | 11 | 3-[1-(difluoromethyl)-1H-pyrazol-3-yl]-N-(2-phenylimidazo[1,2-a]pyridin-3-yl)-4-(trifluoromethyl)benzamide | 3.2 |
| L-005289793-000M | 12 | 3-(1-methyl-1H-pyrazol-3-yl)-N-(6-phenylimidazo[2,1-b][1,3]thiazol-5-yl)-4-(trifluoromethyl)benzamide | 1.9 |

TABLE 2-continued

| L-Number | Compound # | IUPAC Name | IC$_{50}$ (nM) |
|---|---|---|---|
| L-005290498-001S | 13 | 3-(1-methyl-1H-pyrazol-3-yl)-N-[2-(4-methyl-1H-pyrazol-1-yl)imidazo[1,2-a]pyridin-3-yl]-4-(trifluoromethyl)benzamide | 17 |
| L-005292653-001M | 14 | 3-(4-methyl-1,3-oxazol-2-yl)-N-(2-phenylimidazo[1,2-a]pyridin-3-yl)-4-(trifluoromethyl)benzamide | 3.3 |
| L-005292671-000C | 15 | 4-methyl-3-(1-methyl-1H-pyrazol-3-yl)-N-(2-phenylimidazo[1,2-a]pyridin-3-yl)benzamide | 26 |
| L-005294197-001G | 16 | N-[2-(2-methyl-1,3-oxazol-4-yl)imidazo[1,2-a]pyridin-3-yl]-3-(1-methyl-1H-pyrazol-3-yl)-4-(trifluoromethyl)benzamide | 556 |
| L-005302529-000B | 17 | 3-(1-methyl-1H-pyrazol-3-yl)-N-(6-phenylimidazo[2,1-b][1,3,4]thiadiazol-5-yl)-4-(trifluoromethyl)benzamide | 9.2 |
| L-005303372-001E | 18 | N-(8-fluoro-2-phenylimidazo[1,2-a]pyridin-3-yl)-3-(1H-pyrazol-3-yl)-4-(trifluoromethyl)benzamide | 11 |
| L-005305186-001B | 19 | 3-(1-methyl-1H-pyrazol-3-yl)-N-[2-(2-methyl-1,3-thiazol-4-yl)imidazo[1,2-a]pyridin-3-yl]-4-(trifluoromethyl)benzamide | 14 |
| L-005306645-001S | 20 | 2-chloro-5-(1-methyl-1H-pyrazol-3-yl)-N-(2-phenylimidazo[1,2-a]pyridin-3-yl)-4-(trifluoromethyl)benzamide | 0.73 |
| L-005306687-000B | 21 | N-(6-fluoro-2-phenylimidazo[1,2-a]pyridin-3-yl)-3-(1-methyl-1H-pyrazol-3-yl)-4-(trifluoromethyl)benzamide | 3.8 |
| L-005306688-000K | 22 | N-(8-fluoro-2-phenylimidazo[1,2-a]pyridin-3-yl)-3-(1-methyl-1H-pyrazol-3-yl)-4-(trifluoromethyl)benzamide | 1.9 |
| L-005307555-001U | 23 | 2-chloro-5-(1-methyl-1H-pyrazol-3-yl)-N-(2-pyridin-4-ylimidazo[1,2-a]pyridin-3-yl)-4-(trifluoromethyl)benzamide | 2 |
| L-005310764-001Z | 24 | 2-chloro-5-(1-methyl-1H-pyrazol-3-yl)-N-(2-phenylimidazo[1,2-a]pyrimidin-3-yl)-4-(trifluoromethyl)benzamide | 2.8 |
| L-005310786-000Z | 25 | N-methyl-3-({[3-(1-methyl-1H-pyrazol-3-yl)-4-(trifluoromethyl)phenyl]carbonyl}amino)-2-phenylimidazo[1,2-a]pyridine-7-carboxamide | 1.4 |
| L-005320496-000B | 26 | N-[7-(hydroxymethyl)-2-phenylimidazo[1,2-a]pyridin-3-yl]-3-(1-methyl-1H-pyrazol-3-yl)-4-(trifluoromethyl)benzamide | 1.4 |
| L-005320497-000K | 27 | N-[7-(1-hydroxy-1-methylethyl)-2-phenylimidazo[1,2-a]pyridin-3-yl]-3-(1-methyl-1H-pyrazol-3-yl)-4-(trifluoromethyl)benzamide | 1.8 |
| L-005321022-001C | 28 | N,N-dimethyl-3-({[3-(1-methyl-1H-pyrazol-3-yl)-4-(trifluoromethyl)phenyl]carbonyl}amino)-2- | 1.3 |

TABLE 2-continued

| L-Number | Compound # | IUPAC Name | IC$_{50}$ (nM) |
|---|---|---|---|
| | | phenylimidazo[1,2-a]pyridine-7-carboxamide | |
| L-005321025-001D | 29 | N-[7-(azetidin-1-ylcarbonyl)-2-phenylimidazo[1,2-a]pyridin-3-yl]-3-(1-methyl-1H-pyrazol-3-yl)-4-(trifluoromethyl)benzamide | 1.4 |
| L-005322846-001V | 30 | 4-chloro-2-fluoro-N-(2-phenylimidazo[1,2-a]pyridin-3-yl)-5-pyrimidin-2-ylbenzamide | 40 |
| L-005327597-000G | 31 | 3-(1-methyl-1H-pyrazol-3-yl)-N-(3-phenylquinoxalin-2-yl)-4-(trifluoromethyl)benzamide | 27 |
| L-005327807-001G | 32 | 2-hydroxy-5-(1-methyl-1H-pyrazol-3-yl)-N-(2-phenylimidazo[1,2-a]pyridin-3-yl)-4-(trifluoromethyl)benzamide | 477 |
| L-005329808-000C | 33 | 2-cyano-5-(1-methyl-1H-pyrazol-3-yl)-N-(2-phenylimidazo[1,2-a]pyridin-3-yl)-4-(trifluoromethyl)benzamide | 532 |
| L-005336645-001J | 34 | N-(2-phenylimidazo[1,2-a]pyridin-3-yl)-3-(1H-1,2,4-triazol-3-yl)-4-(trifluoromethyl)benzamide | 58 |
| L-005336887-000N | 35 | 2-fluoro-5-(1-methyl-1H-pyrazol-3-yl)-N-(2-phenylimidazo[1,2-a]pyridin-3-yl)-4-(trifluoromethyl)benzamide | 0.49 |
| L-005337092-000D | 36 | N-[6-(1-hydroxy-1-methylethyl)-2-phenylimidazo[1,2-a]pyridin-3-yl]-3-(1-methyl-1H-pyrazol-3-yl)-4-(trifluoromethyl)benzamide | 0.34 |
| L-005337150-000B | 37 | N-[6-(hydroxymethyl)-2-phenylimidazo[1,2-a]pyridin-3-yl]-3-(1-methyl-1H-pyrazol-3-yl)-4-(trifluoromethyl)benzamide | 1.8 |
| L-005341120-000W | 38 | N-[8-(hydroxymethyl)-2-phenylimidazo[1,2-a]pyridin-3-yl]-3-(1-methyl-1H-pyrazol-3-yl)-4-(trifluoromethyl)benzamide | 2.4 |
| L-005344313-000H | 39 | N-(7-bromo-2-phenylimidazo[1,2-a]pyridin-3-yl)-3-(1-methyl-1H-pyrazol-3-yl)-4-(trifluoromethyl)benzamide | 2.7 |
| L-005350292-000P | 40 | 2-fluoro-N-(2-phenylimidazo[1,2-a]pyridin-3-yl)-5-(1H-pyrazol-3-yl)-4-(trifluoromethyl)benzamide | 2.7 |
| L-005357752-000F | 41 | N-{7-[(1S)-1-hydroxyethyl]-2-phenylimidazo[1,2-a]pyridin-3-yl}-3-(1-methyl-1H-pyrazol-3-yl)-4-(trifluoromethyl)benzamide | 0.96 |
| L-005357753-000P | 42 | N-{7-[(1R)-1-hydroxyethyl]-2-phenylimidazo[1,2-a]pyridin-3-yl}-3-(1-methyl-1H-pyrazol-3-yl)-4-(trifluoromethyl)benzamide | 0.79 |
| L-005358083-001V | 43 | N-[7-(1-hydroxy-1-methylethyl)-2-phenylimidazo[1,2-a]pyridin-3-yl]-3-pyrimidin-2-yl-4-(trifluoromethyl)benzamide | 7.9 |
| L-005358086-000U | 44 | N-[6-(1-hydroxy-1-methylethyl)-2-phenylimidazo[1,2-a]pyridin- | 1.4 |

TABLE 2-continued

| L-Number | Compound # | IUPAC Name | IC$_{50}$ (nM) |
|---|---|---|---|
| | | 3-yl]-3-pyrimidin-2-yl-4-(trifluoromethyl)benzamide | |
| L-005359377-001L | 45 | N-{7-[(3-methoxyazetidin-1-yl)methyl]-2-phenylimidazo[1,2-a]pyridin-3-yl}-3-(1-methyl-1H-pyrazol-3-yl)-4-(trifluoromethyl)benzamide | 5.0 |
| L-005359382-000H | 46 | N-[7-(1-hydroxy-1-methylethyl)-2-phenylimidazo[1,2-a]pyridin-3-yl]-3-(4-methyl-1,3-oxazol-2-yl)-4-(trifluoromethyl)benzamide | 0.44 |
| L-005370472-001E | 47 | N-{6-[(3-fluoroazetidin-1-yl)methyl]-2-phenylimidazo[1,2-a]pyridin-3-yl}-3-(1-methyl-1H-pyrazol-3-yl)-4-(trifluoromethyl)benzamide | 8.8 |
| L-005372841-000V | 48 | N-[6-(1-hydroxyethyl)-2-phenylimidazo[1,2-a]pyridin-3-yl]-3-(1-methyl-1H-pyrazol-3-yl)-4-(trifluoromethyl)benzamide | 1.9 |
| L-005372843-000M | 49 | N-[7-(1,2-dihydroxyethyl)-2-phenylimidazo[1,2-a]pyridin-3-yl]-3-(1-methyl-1H-pyrazol-3-yl)-4-(trifluoromethyl)benzamide | 0.51 |
| L-005378000-000F | 50 | 2-fluoro-N-[7-(1-hydroxy-1-methylethyl)-2-phenylimidazo[1,2-a]pyridin-3-yl]-5-(1-methyl-1H-pyrazol-3-yl)-4-(trifluoromethyl)benzamide | 0.45 |
| L-005381910-000N | 51 | N-{7-[1-(dimethylamino)ethyl]-2-phenylimidazo[1,2-a]pyridin-3-yl}-2-fluoro-5-(1-methyl-1H-pyrazol-3-yl)-4-(trifluoromethyl)benzamide | 3.5 |
| L-005381915-000G | 52 | N-[6-(1,2-dihydroxyethyl)-2-phenylimidazo[1,2-a]pyridin-3-yl]-3-(1-methyl-1H-pyrazol-3-yl)-4-(trifluoromethyl)benzamide | 4.9 |
| L-005381923-000G | 53 | 2-fluoro-N-[7-(1-hydroxy-1-methylethyl)-2-phenylimidazo[1,2-a]pyridin-3-yl]-5-pyrimidin-2-yl-4-(trifluoromethyl)benzamide | 1.1 |
| L-005381928-000A | 54 | 2-fluoro-N-[7-(1-hydroxyethyl)-2-phenylimidazo[1,2-a]pyridin-3-yl]-5-(1-methyl-1H-pyrazol-3-yl)-4-(trifluoromethyl)benzamide | 0.40 |
| L-005381929-000J | 55 | 2-fluoro-N-[7-(1-hydroxyethyl)-2-phenylimidazo[1,2-a]pyridin-3-yl]-5-(1-methyl-1H-pyrazol-3-yl)-4-(trifluoromethyl)benzamide | 0.37 |
| L-005381932-000R | 56 | N-{7-[1-(dimethylamino)ethyl]-2-phenylimidazo[1,2-a]pyridin-3-yl}-3-(1-methyl-1H-pyrazol-3-yl)-4-(trifluoromethyl)benzamide | 1.0 |
| L-005384941-000H | 57 | 2-fluoro-N-[7-(1-hydroxyethyl)-2-phenylimidazo[1,2-a]pyridin-3-yl]-5-pyrimidin-2-yl-4-(trifluoromethyl)benzamide | 1.1 |
| L-005384942- | 58 | 2-fluoro-N-[7-(1-hydroxyethyl)-2- | 0.92 |

TABLE 2-continued

| L-Number | Compound # | IUPAC Name | IC$_{50}$ (nM) |
|---|---|---|---|
| 000S | | phenylimidazo[1,2-a]pyridin-3-yl]-5-pyrimidin-2-yl-4-(trifluoromethyl)benzamide | |
| L-005398411-001B | 59 | 2-fluoro-N-(7-methoxy-2-phenylimidazo[1,2-a]pyridin-3-yl]-5-pyrimidin-2-yl-4-(trifluoromethyl)benzamide | 1.7 |
| L-005410146-000Z | 60 | N-[7-(1-hydroxy-1-methylethyl)-2-phenylimidazo[1,2-a]pyridin-3-yl]-3-(3-methyl-1H-pyrazol-1-yl)-4-(trifluoromethyl)benzamide | 14 |
| L-005415724-000D | 61 | N-[7-(1-hydroxyethyl)-2-phenylimidazo[1,2-a]pyridin-3-yl]-3-(4-methyl-1,3-oxazol-2-yl)-4-(trifluoromethyl)benzamide | 2.4 |
| L-005415725-000M | 62 | N-[7-(1-hydroxyethyl)-2-phenylimidazo[1,2-a]pyridin-3-yl]-3-(4-methyl-1,3-oxazol-2-yl)-4-(trifluoromethyl)benzamide | 1.5 |
| L-005423837-000G | 63 | 3-(1-methyl-1H-pyrazol-3-yl)-N-[2-phenyl-7-(2,2,2-trifluoro-1-hydroxyethyl)imidazo[1,2-a]pyridin-3-yl]-4-(trifluoromethyl)benzamide | 1.6 |
| L-005423838-000R | 64 | 3-(1-methyl-1H-pyrazol-3-yl)-N-[2-phenyl-7-(2,2,2-trifluoro-1-hydroxyethyl)imidazo[1,2-a]pyridin-3-yl]-4-(trifluoromethyl)benzamide | 1.1 |
| L-005423839-000Z | 65 | 3-(1-methyl-1H-pyrazol-3-yl)-N-[2-phenyl-6-(2,2,2-trifluoro-1-hydroxyethyl)imidazo[1,2-a]pyridin-3-yl]-4-(trifluoromethyl)benzamide | 12 |
| L-005423840-000N | 66 | 3-(1-methyl-1H-pyrazol-3-yl)-N-[2-phenyl-6-(2,2,2-trifluoro-1-hydroxyethyl)imidazo[1,2-a]pyridin-3-yl]-4-(trifluoromethyl)benzamide | 4.5 |
| L-005423841-000X | 67 | N-[7-(1-hydroxyethyl)-2-phenylimidazo[1,2-a]pyridin-3-yl]-3-pyrimidin-2-yl-4-(trifluoromethyl)benzamide | 5.1 |
| L-005423842-000F | 68 | N-[7-(1-hydroxyethyl)-2-phenylimidazo[1,2-a]pyridin-3-yl]-3-pyrimidin-2-yl-4-(trifluoromethyl)benzamide | 4.6 |
| L-005428481-000A | 69 | N-[7-(1-hydroxycyclopropyl)-2-phenylimidazo[1,2-a]pyridin-3-yl]-3-(1-methyl-1H-pyrazol-3-yl)-4-(trifluoromethyl)benzamide | 3.4 |
| L-005429094-000Z | 70 | 2-chloro-N-[7-(1-hydroxy-1-methylethyl)-2-phenylimidazo[1,2-a]pyridin-3-yl]-5-(1-methyl-1H-pyrazol-3-yl)-4-(trifluoromethyl)benzamide | 1.2 |
| L-005430619-000A | 71 | 2-chloro-N-[7-(1-hydroxy-1-methylethyl)-2-phenylimidazo[1,2-a]pyridin-3-yl]-5-(4-methylpyrimidin-2-yl)-4-(trifluoromethyl)benzamide | 7.6 |
| L-005431083-001H | 72 | 2-fluoro-5-(1-methyl-1H-pyrazol-3-yl)-N-(2-phenyl-1H-indol-3-yl)-4-(trifluoromethyl)benzamide | 4.1 |

TABLE 2-continued

| L-Number | Compound # | IUPAC Name | IC$_{50}$ (nM) |
|---|---|---|---|
| L-005431563-000V | 73 | 2-fluoro-N-[7-(1-hydroxyethyl)-2-phenylimidazo[1,2-a]pyridin-3-yl]-5-(1H-pyrazol-3-yl)-4-(trifluoromethyl)benzamide | 1.4 |
| L-005431564-000D | 74 | 2-fluoro-N-[7-(1-hydroxyethyl)-2-phenylimidazo[1,2-a]pyridin-3-yl]-5-(1H-pyrazol-3-yl)-4-(trifluoromethyl)benzamide | 1.8 |
| L-005432497-000S | 75 | N-[7-(1-hydroxy-1-methylethyl)-2-phenylimidazo[1,2-a]pyridin-3-yl]-2-methyl-5-(1-methyl-1H-pyrazol-3-yl)-4-(trifluoromethyl)benzamide | 4.5 |
| L-005433853-000W | 76 | 2-fluoro-N-(2-phenyl-1H-indol-3-yl)-5-pyrimidin-2-yl-4-(trifluoromethyl)benzamide | 8.2 |
| L-005434120-000U | 77 | 3-[1-(difluoromethyl)-1H-pyrazol-3-yl]-N-[7-(1-hydroxyethyl)-2-phenylimidazo[1,2-a]pyridin-3-yl]-4-(trifluoromethyl)benzamide | 4.0 |
| L-005434122-000L | 78 | 3-[1-(difluoromethyl)-1H-pyrazol-3-yl]-N-[7-(1-hydroxyethyl)-2-phenylimidazo[1,2-a]pyridin-3-yl]-4-(trifluoromethyl)benzamide | 4.8 |
| L-005434123-001X | 79 | N-{7-[(acetylamino)methyl]-2-phenylimidazo[1,2-a]pyridin-3-yl}-3-(1-methyl-1H-pyrazol-3-yl)-4-(trifluoromethyl)benzamide | 8.2 |
| L-005434126-000W | 80 | N-(7-{[(hydroxyacetyl)amino]methyl}-2-phenylimidazo[1,2-a]pyridin-3-yl)-3-(1-methyl-1H-pyrazol-3-yl)-4-(trifluoromethyl)benzamide | 20 |
| L-005438853-000U | 81 | N-(7-{[(methylcarbamoyl)amino]methyl}-2-phenylimidazo[1,2-a]pyridin-3-yl)-3-(1-methyl-1H-pyrazol-3-yl)-4-(trifluoromethyl)benzamide | 15 |
| L-005442661-001Y | 82 | N-[7-({[(1-hydroxycyclopropyl)carbonyl]amino}methyl)-2-phenylimidazo[1,2-a]pyridin-3-yl]-3-(1-methyl-1H-pyrazol-3-yl)-4-(trifluoromethyl)benzamide | 4.6 |
| L-005442662-001G | 83 | methyl {[3-({[3-(1-methyl-1H-pyrazol-3-yl)-4-(trifluoromethyl)phenyl]carbonyl}amino)-2-phenylimidazo[1,2-a]pyridin-7-yl]methyl}carbamate | 0.77 |
| L-005442663-001R | 84 | 3-(1-methyl-1H-pyrazol-3-yl)-N-(7-{[(methylsulfonyl)amino]methyl}-2-phenylimidazo[1,2-a]pyridin-3-yl)-4-(trifluoromethyl)benzamide | 3.1 |
| L-005443020-001F | 85 | 2-fluoro-N-(2-phenylpyrazolo[1,5-a]pyridin-3-yl)-5-pyrimidin-2-yl-4-(trifluoromethyl)benzamide | 5.0 |
| L-005443904-000S | 86 | N-(5-cyano-2-phenyl-1H-indol-3-yl)-2-fluoro-5-pyrimidin-2-yl-4-(trifluoromethyl)benzamide | 2.6 |
| L-005444788- | 87 | 3-(1-methyl-1H-pyrazol-3-yl)-N-[7-(4-methyl-1,3- | 0.68 |

TABLE 2-continued

| L-Number | Compound # | IUPAC Name | IC$_{50}$ (nM) |
|---|---|---|---|
| 001T | | thiazol-2-yl)-2-phenylimidazo[1,2-a]pyridin-3-yl]-4-(trifluoromethyl)benzamide | |
| L-005447847-001H | 88 | 3-(1-methyl-1H-pyrazol-3-yl)-N-(7-morpholin-4-yl-2-phenylimidazo[1,2-a]pyridin-3-yl)-4-(trifluoromethyl)benzamide | 1.2 |
| L-005447848-001S | 89 | 3-(1-methyl-1H-pyrazol-3-yl)-N-(2-phenyl-7-pyrrolidin-1-ylimidazo[1,2-a]pyridin-3-yl)-4-(trifluoromethyl)benzamide | 5.0 |
| L-005447863-001H | 90 | 3-(1-methyl-1H-pyrazol-3-yl)-N-(2-phenyl-7-piperazin-1-ylimidazo[1,2-a]pyridin-3-yl)-4-(trifluoromethyl)benzamide | 3.8 |
| L-005451037-000G | 91 | 3-({[2-fluoro-5-pyrimidin-2-yl-4-(trifluoromethyl)phenyl]carbonyl}amino)-2-phenyl-1H-indole-5-carboxylic acid | 11 |
| L-005453178-000J | 92 | 3-({[2-fluoro-5-pyrimidin-2-yl-4-(trifluoromethyl)phenyl]carbonyl}amino)-2-phenyl-1H-indole-5-carboxamide | 8.7 |
| L-005453997-000N | 93 | N-{7-[(1R)-1-hydroxyethyl]-2-phenylimidazo[1,2-a]pyridin-3-yl}-2-methyl-5-(1-methyl-1H-pyrazol-3-yl)-4-(trifluoromethyl)benzamide | 4.7 |
| L-005459169-000T | 94 | 2-fluoro-N-[5-(1-hydroxyethyl)-2-phenyl-1H-indol-3-yl]-5-pyrimidin-2-yl-4-(trifluoromethyl)benzamide | 6.5 |
| L-005459170-000G | 95 | 2-fluoro-N-[5-(1-hydroxyethyl)-2-phenyl-1H-indol-3-yl]-5-pyrimidin-2-yl-4-(trifluoromethyl)benzamide | 4.9 |
| L-005459174-000S | 96 | N-[5-(1-hydroxy-1-methylethyl)-2-phenylpyrazolo[1,5-a]pyridin-3-yl]-3-(1-methyl-1H-pyrazol-3-yl)-4-(trifluoromethyl)benzamide | 6.7 |
| L-005460460-000G | 97 | N-[5-(1-hydroxyethyl)-2-phenylpyrazolo[1,5-a]pyridin-3-yl]-3-(1-methyl-1H-pyrazol-3-yl)-4-(trifluoromethyl)benzamide | 1.9 |
| L-005460463-000H | 98 | N-[5-(1-hydroxyethyl)-2-phenylpyrazolo[1,5-a]pyridin-3-yl]-3-(1-methyl-1H-pyrazol-3-yl)-4-(trifluoromethyl)benzamide | 3.3 |
| L-005460846-000N | 99 | N-[7-(2-hydroxyethyl)-2-phenylimidazo[1,2-a]pyridin-3-yl]-3-(1-methyl-1H-pyrazol-3-yl)-4-(trifluoromethyl)benzamide | 2.1 |
| L-005461429-000K | 100 | N-[7-(2-aminoethyl)-2-phenylimidazo[1,2-a]pyridin-3-yl]-3-(1-methyl-1H-pyrazol-3-yl)-4-(trifluoromethyl)benzamide | 13 |
| L-005461431-000H | 101 | N-{7-[2-(acetylamino)ethyl]-2-phenylimidazo[1,2-a]pyridin-3-yl}-3-(1-methyl-1H-pyrazol-3-yl)-4-(trifluoromethyl)benzamide | 10 |
| L-005461432-000S | 102 | 3-(1-methyl-1H-pyrazol-3-yl)-N-(7-{2-[(methylsulfonyl)amino]ethyl}-2-phenylimidazo[1,2- | 4.3 |

TABLE 2-continued

| L-Number | Compound # | IUPAC Name | IC$_{50}$ (nM) |
|---|---|---|---|
| | | a]pyridin-3-yl)-4-(trifluoromethyl)benzamide | |
| L-005461630-000U | 103 | 2-fluoro-N-[5-(1-hydroxy-1-methylethyl)-2-phenylpyrazolo[1,5-a]pyridin-3-yl]-5-(1-methyl-1H-pyrazol-3-yl)-4-(trifluoromethyl)benzamide | 0.94 |
| L-005463798-000S | 104 | methyl {2-[3-({[3-(1-methyl-1H-pyrazol-3-yl)-4-(trifluoromethyl)phenyl]carbonyl}amino)-2-phenylimidazo[1,2-a]pyridin-7-yl]ethyl}carbamate | 1.7 |
| L-005464464-000V | 105 | 2-fluoro-N-(2-phenylimidazo[1,2-a]pyridin-3-yl)-5-pyrimidin-2-yl-4-(trifluoromethyl)benzamide | 1.4 |
| L-005465564-000Z | 106 | 2-fluoro-N-[5-(1-hydroxyethyl)-2-phenylpyrazolo[1,5-a]pyridin-3-yl]-5-(1-methyl-1H-pyrazol-3-yl)-4-(trifluoromethyl)benzamide | 1.7 |
| L-005465565-000H | 107 | 2-fluoro-N-[5-(1-hydroxyethyl)-2-phenylpyrazolo[1,5-a]pyridin-3-yl]-5-(1-methyl-1H-pyrazol-3-yl)-4-(trifluoromethyl)benzamide | 0.85 |
| L-005465566-000S | 108 | N-(5-cyano-2-phenyl-1H-indol-3-yl)-2-fluoro-5-(1-methyl-1H-pyrazol-3-yl)-4-(trifluoromethyl)benzamide | 1.0 |
| L-005465700-000E | 109 | N-{7-[2-(methylamino)ethyl]-2-phenylimidazo[1,2-a]pyridin-3-yl}-3-(1-methyl-1H-pyrazol-3-yl)-4-(trifluoromethyl)benzamide | 169 |
| L-005466358-000S | 110 | 3-({[2-fluoro-5-(1-methyl-1H-pyrazol-3-yl)-4-(trifluoromethyl)phenyl]carbonyl}amino)-2-phenyl-1H-indole-5-carboxylic acid | 3.6 |
| L-005469349-000S | 111 | N-(6-cyano-2-phenylpyrazolo[1,5-a]pyridin-3-yl)-2-fluoro-5-(1-methyl-1H-pyrazol-3-yl)-4-(trifluoromethyl)benzamide | 1000 |
| L-005469595-000N | 112 | 2-fluoro-N-[5-(1-hydroxyethyl)-2-phenyl-1H-indol-3-yl]-5-(1-methyl-1H-pyrazol-3-yl)-4-(trifluoromethyl)benzamide | 1.4 |
| L-005469611-000Z | 113 | 2-fluoro-N-[5-(1-hydroxyethyl)-2-phenyl-1H-indol-3-yl]-5-(1-methyl-1H-pyrazol-3-yl)-4-(trifluoromethyl)benzamide | 1.7 |
| L-005475796-000C | 114 | 3-(1-methyl-1H-pyrazol-3-yl)-N-(2-phenyl-7-pyrrolidin-2-ylimidazo[1,2-a]pyridin-3-yl)-4-(trifluoromethyl)benzamide | 15 |
| L-005481696-000D | 115 | 2-fluoro-N-{7-[(1R)-1-hydroxyethyl]-2-phenylimidazo[1,2-a]pyridin-3-yl}-5-(1-methyl-1H-pyrazol-3-yl)-4-(1,1,2-trifluoroethyl)benzamide | 3.7 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula I:

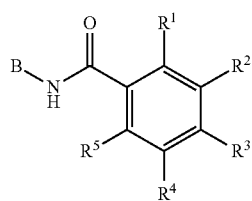

I or a pharmaceutically acceptable salt thereof, wherein

B is selected from the group consisting of unsubstituted or substituted imidazopyridinyl, imidazothiazolyl, imidazopyrimidinyl, imidazopyridazinyl, imidazothiadiazolyl, quinoxalinyl;

R is selected from the group consisting of hydrogen, OH, or —$C_{1-6}$ alkyl;

$R^1$ and $R^5$ are independently selected from the group consisting of hydrogen, CN, OH, $C_{1-6}$alkyl, and halogen;

$R^2$ and $R^4$ is hydrogen and the other is $(CHR)_nC_{5-10}$ heterocycle, said heterocycle optionally substituted with 1 to 3 groups of $R^a$;

$R^3$ is selected from the group consisting of $C_{2-6}$ alkyl, $C_{1-4}$ haloalkyl, —$OC_{1-4}$haloalkyl, and halogen;

$R^a$ is selected from the group consisting of —CN, $NO_2$, —$C_{1-4}$haloalkyl, —$OC_{1-4}$ haloalkyl, —$C_{1-6}$alkyl, —$C_{1-6}$alkenyl, —$C_{1-6}$alkynyl, —$(CHR)_nC_{6-10}$aryl, —$(CHR)_nC_{4-10}$aryl, heterocycle, —$(CHR)_nC(O)(CHR)_nC_{4-10}$ heterocycle, —O—$(CH_2)_nC_{6-10}$aryl, —O—$(CH_2)_nC_{4-10}$heterocycle-0-, —$(CH_2)_nN(R^d)_2$, —$(CH_2)_nC(O)NH(CH_2)_nC_{4-10}$ heterocycle, $SO_2R^d$, —$SO_2N(R^d)_2$, —$C(O)CF_3$, COR, —$(CH_2)_n$halo, —$(CH_2)_nNHC(O)R^d$, —$(CH_2)_nNHC(O)NHR^d$, —$(CH_2)_nNHC(O)OR^d$, —$(CHR)_nC(O)N(R^d)_2$, -0-$C_{1-6}$ alkyl, and —OH, said alkyl, aryl and heterocycle optionally substituted with 1 to 3 groups of $R^b$, wherein when two $R^d$ groups are attached to a nitrogen atom they may combine with that nitrogen to from a 4-8 membered heterocycle that is optionally substituted with 1 to 3 groups of $R^f$;

$R^b$ is selected from the group consisting of —$C_{1-6}$alkyl, —$C_{1-6}$alkylOR, —$C_{1-4}$haloalkyl, —$(CH_2)_nC_{3-6}$cycloalkyl, —$(CH_2)_nN(R^d)_2$, —$(CH_2)_nOR^c$, -0-, halogen, —CN, $S(O)(NH)R^g$, —$SO_2R$, —$SO_2N(R^d)_2$, —O—$(CH_2)_nC_{4-10}$ heterocycle, —$(CH_2)_nC(O)N(R^d)_2$, —$(CH_2)_nNHC(O)R^d$, —$C_{1-6}$alkylN$(R^d)_2$, and halo, said cycloalkyl optionally substituted with 1 to 3 groups of $R^f$, and wherein when two $R^d$ groups are attached to a nitrogen atom they may combine with that nitrogen to from a 4-8 membered heterocycle that is optionally substituted with 1 to 3 groups of $R^f$;

$R^c$ is selected from the group consisting of hydrogen, —$C_{1-6}$alkylOR$^g$, and —$C_{1-6}$alkyl;

$R^d$ is independently selected from the group consisting of hydrogen, —$C_{1-4}$haloalkyl-$C_{1-6}$alkyl, —$(CH_2)_n$NR$^f$C$_{4-10}$ heterocycle, —$(CH_2)_nC_{3-6}$cycloalkyl, and —$(CH_2)_n$ $C_{4-10}$heterocycle said alkyl, cycloalkyl and heterocycle optionally substituted with 1 to 3 groups of $R^f$;

$R^f$ is selected from the group consisting of hydrogen, OR$^c$, CN, —N(R$^c$)$_2$, C(O)N(R$^g$)$_2$, C(O)C$_{1-6}$alkyl, —SO$_2$R$^g$,-0-, —$C_{1-6}$alkylSO$_2$R$^g$, —$C_{1-6}$alkyl$_n$(R$^g$)$_2$, $R^g$ is selected from the group consisting of hydrogen, and —$C_{1-6}$alkyl; and n represents 0-6.

2. The compound according to claim 1 wherein B is unsubstituted or substituted imidazopyridinyl or imidazopyrimidinyl.

3. The compound according to claim 1 wherein the optionally substituted heterocycle of $R^2$ and $R^4$ is a five or six membered ring containing one or more heteroatoms at least one of which is nitrogen.

4. The compound according to claim 1 wherein one of $R^2$ and $R^4$ is hydrogen and the other is selected from the group consisting of optionally substituted pyrazolyl, pyridyl, thiazolyl, oxazolyl, pyrimidinyl, pyridazinyl, pyrazinyl, thiadiazolyl, oxadiazolyl and triazolyl.

5. The compound according to claim 4 wherein the heterocycle is optionally substituted pyrazolyl.

6. The compound according to claim 1 wherein $R^3$ is selected from the group consisting of hydrogen, $CF_3$, $OCF_3$, chlorine, and fluorine.

7. The compound according to claim 1 of formula I wherein B is represented by structural formulas (a), (b), (c), (d), (e), (f), (g), (h), or (i):

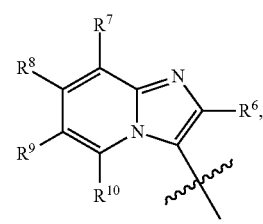

(a)

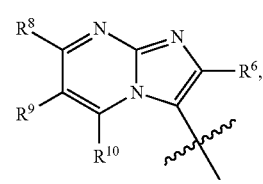

(b)

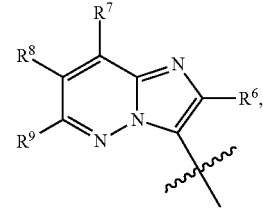

(c)

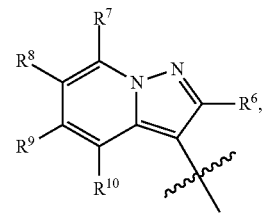

(d)

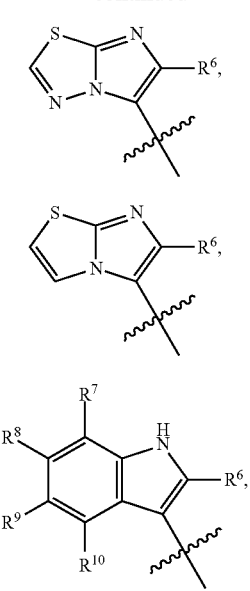

(e), (f), (g)

wherein:
R⁶ represents (CH₂)$_n$C$_{6-10}$aryl, or (CH₂)$_n$C$_{5-10}$heterocycle, said aryl, and heterocycle optionally substituted with 1 to 3 groups of R$^a$; and R⁷, R⁸, R⁹ and R¹⁰ independently represent hydrogen, halogen, CN, C$_{1-6}$alkyl, C(O)N(R)₂, C(O)(CH₂)$_n$C$_{5-10}$heterocycle, (CH₂)$_n$C$_{6-10}$°aryl, or (CH₂)$_n$C$_{5-10}$heterocycle, said alkyl, aryl, and heterocycle optionally substituted with 1 to 3 groups of R$^a$.

8. The compound according to claim 7 wherein B is imidazopyridinyl or indazolyl represented by structural formula (a) or (b), respectively.

9. The compound according to claim 8 wherein B is imidazopyridinyl or indazolyl represented by structural formula (a) or (b), respectively, R⁶ is unsubstituted or substituted phenyl, thiazolyl, pyrazolyl, pyridyl, isoxazolyl, oxazoly, or pyrimidinyl, R⁸ and R⁹ are independently selected from hydrogen, halogen, CN, CH₂OH, C(O)N(R)₂, and optionally substituted C$_{1-6}$alkyl, phenyl, pyrazolyl, isoxazolyl, oxazolyl, (CH₂)$_n$azetidinyl, and C(O)NHazetidinyl and R⁷ and R¹⁰ are independently selected from hydrogen, C$_{1-6}$alkyl, and halogen, said alkyl optionally substituted with 1 to 3 groups of R$^b$.

10. The compound of formula II according to claim 1:

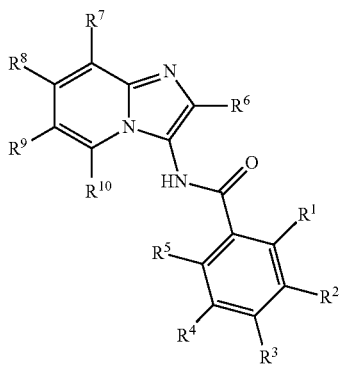

II wherein:
R⁶ is unsubstituted or substituted phenyl, thiazolyl, pyrazolyl, pyridyl, isoxazolyl, oxazolyl or pyrimidinyl, R⁸ and R⁹ are independently selected from hydrogen, halogen, CN, CH₂OH, C(O)N(R)₂, and optionally substituted C$_{1-6}$alkyl, phenyl, pyrazolyl, isoxazolyl, oxazolyl, (CH₂)$_n$azetidinyl, and C(O)NHazetidinyl, R⁷ and R¹⁰ are independently selected from hydrogen, C$_{1-6}$alkyl, and halogen, said alkyl optionally substituted with 1 to 3 groups of R$^b$, R³ is selected from the group consisting of hydrogen, CF₃, OCF₃, CH₃, chlorine and fluorine, and one of R² and R⁴ is hydrogen and the other is (CHR)$_n$C$_{5-10}$ heterocycle, said heterocycle optionally substituted with 1 to 3 groups of R$^a$.

11. The compound according to claim 10 wherein R¹ and R⁵ are both hydrogen or one is hydrogen and the other halogen, R³ is OCF₃, or CF₃, one of R² and R⁴ is hydrogen and the other is an optionally substituted (CHR)$_n$C$_{5-10}$ heterocycle that is a five or six membered ring containing one or more heteroatoms at least one of which is nitrogen.

12. The compound according to claim 11 wherein the optionally substituted heterocycle of R² and R⁴ is selected from the group consisting of pyrazolyl, pyridyl, thiazolyl, oxazolyl, pyrimidinyl, pyridazinyl, pyrazinyl, thiadiazolyl, oxadiazolyl and triazolyl.

13. The compound according to claim 10 wherein one of R² and R⁴ is hydrogen and the other is is pyrazolyl, R⁶ is optionally substituted phenyl and R³ is CF₃.

14. A compound which is selected from the group consisting of
N-(2-phenylimidazo[1,2-a]pyridin-3-yl)-4-(trifluoromethoxy)benzamide;
2-fluoro-N-(6-phenylimidazo[2,1-b][1,3]thiazol-5-yl)-4-(trifluoromethyl)benzamide;
3-(1-methyl-1H-pyrazol-3-yl)-N-(2-phenylimidazo[1,2-a]pyrimidin-3-yl)-4-(trifluoromethyl)benzamide;
3-(1-methyl-1H-pyrazol-3-yl)-N-(2-pyridin-2-ylimidazo[1,2-a]pyridin-3-yl)-4-(trifluoromethyl)benzamide;
3-(1-methyl-1H-pyrazol-3-yl)-N-(2-phenylimidazo[1,2-b]pyridazin-3-yl)-4-(trifluoromethyl)benzamide;
2-fluoro-N-[5-(1-methylethyl)-2-phenylimidazo[1,2-a]pyridin-3-yl]-4-(trifluoromethyl)benzamide;
3-(1-methyl-1H-pyrazol-3-yl)-N-(2-pyrimidin-4-ylimidazo[1,2-a]pyridin-3-yl)-4-(trifluoromethyl)benzamide;
N-(2-phenylimidazo[1,2-a]pyridin-3-yl)-3-(1H-pyrazol-3-yl)-4-(trifluoromethyl)benzamide;
2-fluoro-N-(2-isoxazol-5-ylimidazo[1,2-a]pyridin-3-yl)-4-(trifluoromethyl)benzamide;
3-[1-(difluoromethyl)-1H-pyrazol-3-yl]-N-(2-phenylimidazo[1,2-a]pyridin-3-yl)-4-(trifluoromethyl)benzamide;
3-(1-methyl-1H-pyrazol-3-yl)-N-(6-phenylimidazo[2,1-b][1,3]thiazol-5-yl)-4-(trifluoromethyl)benzamide;
3-(1-methyl-1H-pyrazol-3-yl)-N-[2-(4-methyl-1H-pyrazol-1-yl)imidazo[1,2-a]pyridin-3-yl]-4-(trifluoromethyl)benzamide;
3-(4-methyl-1,3-oxazol-2-yl)-N-(2-phenylimidazo[1,2-a]pyridin-3-yl)-4-(trifluoromethyl)benzamide;
N-[2-(2-methyl-1,3-oxazol-4-yl)imidazo[1,2-a]pyridin-3-yl]-3-(1-methyl-1H-pyrazol-3-yl)-4-(trifluoromethyl)benzamide;
3-(1-methyl-1H-pyrazol-3-yl)-N-(6-phenylimidazo[2,1-b)][1,3,4]thiadiazol-5-yl)-4-(trifluoromethyl)benzamide;
N-(8-fluoro-2-phenylimidazo[1,2-a]pyridin-3-yl)-3-(1H-pyrazol-3-yl)-4-(trifluoromethyl)benzamide;

3-(1-methyl-1H-pyrazol-3-yl)-N-[2-(2-methyl-1,3-thiazol-4-yl)imidazo[1,2-a]pyridin-3-yl]-4-(trifluoromethyl)benzamide;
N-(6-fluoro-2-phenylimidazo[1,2-a]pyridin-3-yl)-3-(1-methyl-1H-pyrazol-3-yl)-4-(trifluoromethyl)benzamide;
2-chloro-5-(1-methyl-1H-pyrazol-3-yl)-N-(2-pyridin-4-ylimidazo[1,2-a]pyridin-3-yl)-4-(trifluoromethyl)benzamide;
2-chloro-5-(1-methyl-1H-pyrazol-3-yl)-N-(2-phenylimidazo[1,2-a]pyrimidin-3-yl)-4-(trifluoromethyl)benzamide;
N-methyl-3-({[3-(1-methyl-1H-pyrazol-3-yl)-4-(trifluoromethyl)phenyl]carbonyl}amino)-2-phenylimidazo[1,2-a]pyridine-7-carboxamide;
N-[7-(azetidin-1-ylcarbonyl)-2-phenylimidazo[1,2-a]pyridin-3-yl]-3-(1-methyl-1H-pyrazol-3-yl)-4-(trifluoromethyl)benzamide;
4-chloro-2-fluoro-N-(2-phenylimidazo[1,2-a]pyridin-3-yl)-5-pyrimidin-2-ylbenzamide;
3-(1-methyl-1H-pyrazol-3-yl)-N-(3-phenylquinoxalin-2-yl)-4-(trifluoromethyl)benzamide;
2-cyano-5-(1-methyl-1H-pyrazol-3-yl)-N-(2-phenylimidazo[1,2-a]pyridin-3-yl)-4-(trifluoromethyl)benzamide;
N-(2-phenylimidazo[1,2-a]pyridin-3-yl)-3-(1H-1,2,4-triazol-3-yl)-4-(trifluoromethyl)benzamide;
N-[6-(1-hydroxy-1-methylethyl)-2-phenylimidazo[1,2-a]pyridin-3-yl]-3-(1-methyl-1H-pyrazol-3-yl)-4-(trifluoromethyl)benzamide;
N-[8-(hydroxymethyl)-2-phenylimidazo[1,2-a]pyridin-3-yl]-3-(1-methyl-1H-pyrazol-3-yl)-4-(trifluoromethyl)benzamide;
N-(7-bromo-2-phenylimidazo[1,2-a]pyridin-3-yl)-3-(1-methyl-1H-pyrazol-3-yl)-4-(trifluoromethyl)benzamide;
N-{7-[(3-methoxyazetidin-1-yl)methyl]-2-phenylimidazo[1,2-a]pyridin-3-yl}-3-(1-methyl-1H-pyrazol-3-yl)-4-(trifluoromethyl)benzamide;
N-{6-[(3-fluoroazetidin-1-yl)methyl]-2-phenylimidazo[1,2-a]pyridin-3-yl}-3-(1-methyl-1H-pyrazol-3-yl)-4-(trifluoromethyl)benzamide;
N-{7-[1-(dimethylamino)ethyl]-2-phenylimidazo[1,2-a]pyridin-3-yl}-2-fluoro-5-(1-methyl-1H-pyrazol-3-yl)-4-(trifluoromethyl)benzamide;
2-fluoro-N-[7-(1-hydroxy-1-methylethyl)-2-phenylimidazo[1,2-a]pyridin-3-yl]-5-pyrimidin-2-yl-4-(trifluoromethyl)benzamide;
2-fluoro-N-[7-(1-hydroxyethyl)-2-phenylimidazo[1,2-a]pyridin-3-yl]-5-(1-methyl-1H-pyrazol-3-yl)-4-(trifluoromethyl)benzamide;
2-fluoro-N-(2-phenylimidazo[1,2-a]pyridin-3-yl)-4-(trifluoromethyl)benzamide;
3-(1-methyl-1H-pyrazol-3-yl)-N-(2-phenylimidazo[1,2-a]pyridin-3-yl)-4-(trifluoromethyl)benzamide or a pharmaceutically acceptable salt thereof.

15. A pharmaceutical composition comprising a therapeutically effective amount of a compound of claim 1 or a pharmaceutically acceptable salt thereof, and a pharmaceutically acceptable carrier.

16. A method of treating a disease or disorder mediated by the TrK receptors, wherein said disease or disorder is selected from the group consisting of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA in a patient in need thereof, comprising administering to the patient a therapeutically effective amount of a compound of claim 1 or a pharmaceutically acceptable salt thereof, and a pharmaceutically acceptable carrier.

* * * * *